United States Patent
Kawasumi et al.

(10) Patent No.: US 10,991,974 B2
(45) Date of Patent: Apr. 27, 2021

(54) ELECTROLYTIC SOLUTION FOR SECONDARY BATTERY, SECONDARY BATTERY, BATTERY PACK, ELECTRICALLY DRIVEN VEHICLE AND ELECTRONIC EQUIPMENT

(71) Applicant: MURATA MANUFACTURING CO., LTD., Kyoto (JP)

(72) Inventors: Katsuaki Kawasumi, Kyoto (JP); Toru Odani, Kyoto (JP); Kazumasa Takeshi, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 44 days.

(21) Appl. No.: 16/378,021

(22) Filed: Apr. 8, 2019

(65) Prior Publication Data
US 2019/0237799 A1   Aug. 1, 2019

Related U.S. Application Data

(63) Continuation of application No. PCT/JP2017/036065, filed on Oct. 4, 2017.

(51) Int. Cl.
*H01M 10/0525*  (2010.01)
*H01M 10/0567*  (2010.01)
(Continued)

(52) U.S. Cl.
CPC ......... *H01M 10/0525* (2013.01); *B60L 50/64* (2019.02); *C07C 317/24* (2013.01);
(Continued)

(58) Field of Classification Search
CPC ......... H01M 10/0525; H01M 10/0567; H01M 10/44; H01M 2220/20; H01M 2300/0028; H01M 2/263; H01M 4/1315
See application file for complete search history.

(56) References Cited

U.S. PATENT DOCUMENTS

| | | | |
|---|---|---|---|
| 6,015,639 A | 1/2000 | Gao et al. | |
| 2008/0138714 A1 | 6/2008 | Ihara et al. | |
| 2015/0004501 A1 | 1/2015 | Koh et al. | |

FOREIGN PATENT DOCUMENTS

| | | |
|---|---|---|
| FR | 2903691 | 1/2008 |
| JP | 2008146983 A | 6/2008 |

(Continued)

OTHER PUBLICATIONS

International Search Report for Application No. PCT/JP2017/036065, dated Nov. 7, 2017.
(Continued)

*Primary Examiner* — Carlos Barcena
(74) *Attorney, Agent, or Firm* — K&L Gates LLP

(57) ABSTRACT

A secondary battery includes a positive electrode, a negative electrode, and an electrolytic solution including at least one kind of sulfonyl compounds that are represented by a chemical formula $R1(-O-C(=O)-R2-S(=O)_2-Rf1)_{n1}$ or the like. In the chemical formula, R1 represents of an n1-valent hydrocarbon group, an n1-valent oxygen-containing hydrocarbon group, an n1-valent halogenated hydrocarbon group and an n1-valent halogenated oxygen-containing hydrocarbon group. R2 represents one of a divalent hydrocarbon group and a divalent halogenated hydrocarbon group. Rf1 represents one of a halogen group and a monovalent halogenated hydrocarbon group. n1 is an integer of 2 or more.

31 Claims, 6 Drawing Sheets

(51) Int. Cl.
*C07C 317/24* (2006.01)
*H01M 10/44* (2006.01)
*B60L 50/64* (2019.01)
H01M 4/1315 (2010.01)
H01M 50/538 (2021.01)

(52) U.S. Cl.
CPC ....... *H01M 10/0567* (2013.01); *H01M 10/44* (2013.01); *H01M 4/1315* (2013.01); *H01M 50/538* (2021.01); *H01M 2220/20* (2013.01); *H01M 2300/0028* (2013.01); *Y02E 60/10* (2013.01); *Y02T 10/70* (2013.01)

(56) References Cited

FOREIGN PATENT DOCUMENTS

| | | |
|---|---|---|
| JP | 2013093321 A | 5/2013 |
| JP | 2013-134859 | 7/2013 |
| JP | 2016-119212 | 6/2016 |
| WO | 2008009815 A1 | 1/2008 |

OTHER PUBLICATIONS

Japanese Office Action dated Aug. 20, 2019 in corresponding Japanese Application No. 2016-215159.

ELECTROLYTIC SOLUTION FOR SECONDARY BATTERY, SECONDARY BATTERY, BATTERY PACK, ELECTRICALLY DRIVEN VEHICLE AND ELECTRONIC EQUIPMENT

CROSS REFERENCE TO RELATED APPLICATIONS

The present application is a continuation of PCT patent application no. PCT/JP2017/036065, filed on Oct. 4, 2017, which claims priority to Japanese patent application no. JP2016-215159 filed on Nov. 2, 2016, the entire contents of which are being incorporated herein by reference.

BACKGROUND

The present technology generally relates to an electrolytic solution used in a secondary battery, a secondary battery using the electrolytic solution, as well as a battery pack, an electrically driven vehicle and electronic equipment using the secondary battery.

A variety of electronic equipment such as a cellular phone and a personal digital assistant (PDA) has been widely spread, and miniaturization, weight saving and lifetime prolongation of the electronic equipment are demanded. Then, development of a battery, particularly, a secondary battery that is small and lightweight, and can afford the high energy density, as an electric power source, is being advanced.

Application of the secondary battery is not limited to the above-mentioned electronic equipment, but application to other intended uses is also being reviewed. An example is a battery pack that is detachably mounted in electronic equipment or the like and an electrically driven vehicle such as an electric car.

This secondary battery is provided with an electrolytic solution together with a positive electrode and a negative electrode. Since the composition of the electrolytic solution greatly influences the battery property, the composition of the electrolytic solution is being variously reviewed.

SUMMARY

Electronic equipment and the like have been more and more increased in the performance and the function. For this reason, the frequency of use of electronic equipment or the like has been increased, and the use environment of the electronic equipment or the like has been expanded. Accordingly, regarding the battery property of the secondary battery, there remains room for improvement.

Therefore, it is desirable to provide an electrolytic solution for a secondary battery, a secondary battery, a battery pack, an electrically driven vehicle and electronic equipment, which can afford the excellent battery property.

According to an embodiment of the present technology, an electrolytic solution for a secondary battery is provided. The electrolytic solution includes at least one kind of sulfonyl compounds that are represented by each of chemical formula (1), chemical formula (2) and chemical formula (3).

[Chemical formula 1]

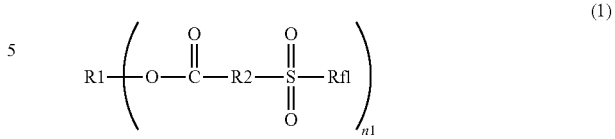

(R1 represents one of an n1-valent hydrocarbon group, an n1-valent oxygen-containing hydrocarbon group, an n1-valent halogenated hydrocarbon group and an n1-valent halogenated oxygen-containing hydrocarbon group. R2 represents one of a divalent hydrocarbon group and a divalent halogenated hydrocarbon group. Rf1 represents one of a halogen group and a monovalent halogenated hydrocarbon group. n1 is an integer of 2 or more.)

[Chemical formula 2]

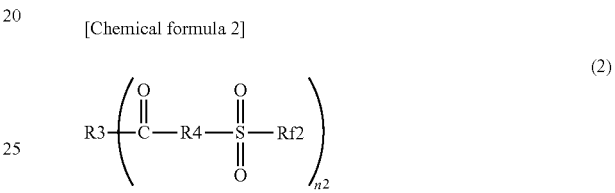

(R3 represents one of an n2-valent hydrocarbon group, an n2-valent oxygen-containing hydrocarbon group, an n2-valent halogenated hydrocarbon group and an n2-valent halogenated oxygen-containing hydrocarbon group. R4 represents one of a divalent hydrocarbon group and a divalent halogenated hydrocarbon group. Rf2 represents one of a halogen group and a monovalent halogenated hydrocarbon group. n2 is an integer of 1 or more.

[Chemical formula 3]

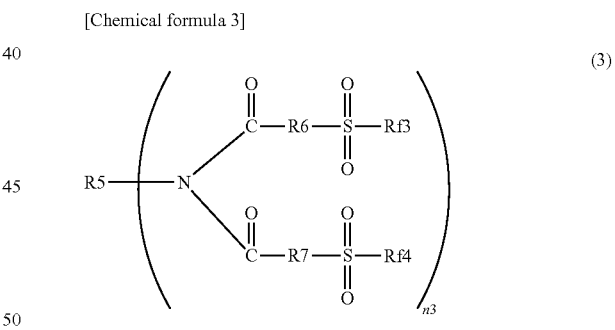

(R5 represents one of an n3-valent hydrocarbon group, an n3-valent oxygen-containing hydrocarbon group, an n3-valent halogenated hydrocarbon group and an n3-valent halogenated oxygen-containing hydrocarbon group. Each of R6 and R7 represents one of a divalent hydrocarbon group and a divalent halogenated hydrocarbon group. Each of Rf3 and Rf4 represents one of a halogen group and a monovalent halogenated hydrocarbon group. n3 is an integer of 1 or more.)

According to an embodiment of the present technology, a secondary battery is provided. The secondary battery includes a positive electrode, a negative electrode and an electrolytic solution, and the electrolytic solution has the same constitution as that of the electrolytic solution as described herein for a secondary battery of one embodiment of the present technology.

Each of a battery pack, an electrically driven vehicle and electronic equipment of an embodiment of the present technology is provided with a secondary battery, and the secondary battery has the same constitution as that of the secondary battery according to the embodiment as described herein.

Herein, the "n1-valent hydrocarbon group" is a generic name of a monovalent group that is formed of carbon (C) and hydrogen (H). This n1-valent hydrocarbon group may be a linear chain, may be a branched chain having one or two or more branch portions, may be cyclic, or may be in the state where two or more of them are mutually bound. Furthermore, the n1-valnet hydrocarbon group may comprise one or two or more intercarbon unsaturated bonds (one or both of an intercarbon double bond and an intercarbon triple bond), or need not comprise the intercarbon unsaturated bond.

The "n1-valent oxygen-containing hydrocarbon group" is a group in which one or two or more ether bonds (—O—) are introduced in the middle of the above-mentioned n1-valent hydrocarbon group. The "n1-valent halogenated hydrocarbon group" is a group in which at least one hydrogen group (—H) of the above-mentioned n1-valent hydrocarbon group is substituted with a halogen group. The "n1-valent halogenated oxygen-containing hydrocarbon group" is a group in which at least one hydrogen group of the above-mentioned n1-valent oxygen-containing hydrocarbon group is substituted with a halogen group.

Details regarding each of the "n2-valent hydrocarbon group, the n2-valent oxygen-containing hydrocarbon group, the n2-valent halogenated hydrocarbon group and the n2-valnet halogenated oxygen-containing hydrocarbon group" are the same as the above-mentioned details regarding each of the n1-valent hydrocarbon group, the n1-valent oxygen-containing hydrocarbon group, the n1-valent halogenated hydrocarbon group and the n1-valent halogenated oxygen-containing hydrocarbon group, except that the valence is different.

Details regarding each of the "n3-valent hydrocarbon group, the n3-valent oxygen-containing hydrocarbon group, the n3-valent halogenated hydrocarbon group and the n3-valent halogenated oxygen-containing hydrocarbon group" are the same as the above-mentioned details regarding each of the n1-valent hydrocarbon group, the n1-valent oxygen-containing hydrocarbon group, the n1-valent halogenated hydrocarbon group and the n1-valent halogenated oxygen-containing hydrocarbon group, except that the valence is different.

The "divalent hydrocarbon group" is a generic name of a divalent group that is formed of carbon and hydrogen. This divalent hydrocarbon group may be a linear chain, may be a branched chain having one or two or more branch portions, may be cyclic, or may be in the state where those two or more kinds are mutually bound. Furthermore, the divalent hydrocarbon group may comprise one or two or more intercarbon unsaturated bonds, or not comprise the intercarbon unsaturated bond. The "divalent halogenated hydrocarbon group" is a group in which at least one hydrogen group of the above-mentioned divalent hydrocarbon group is substituted with a halogen group.

The "monovalent halogenated hydrocarbon group" is a group in which at least one hydrogen group of a monovalent hydrocarbon group is substituted with a halogen group, and the "monovalent hydrocarbon group" is a generic name of a monovalent group that is formed of carbon and hydrogen. This monovalent hydrocarbon group may be a linear chain, may be a branched chain having one or two or more branch portions, may be cyclic, or may be in the state where those two or more kinds are mutually bound. Furthermore, the monovalent hydrocarbon group may comprise one or two or more intercarbon unsaturated bonds, or not comprise the intercarbon unsaturated bond.

According to the electrolytic solution for a secondary battery or the secondary battery of one embodiment of the present technology, since the electrolytic solution contains the above-mentioned sulfonyl compound, the excellent battery property can be obtained.

Furthermore, also in the battery pack, the electrically driven vehicle or the electronic equipment of one embodiment of the present technology, the same effect can be obtained.

In addition, the effect described herein is not necessarily limited, but may be any effect described in the present technology.

DETAILED DESCRIPTION

Figure 1:
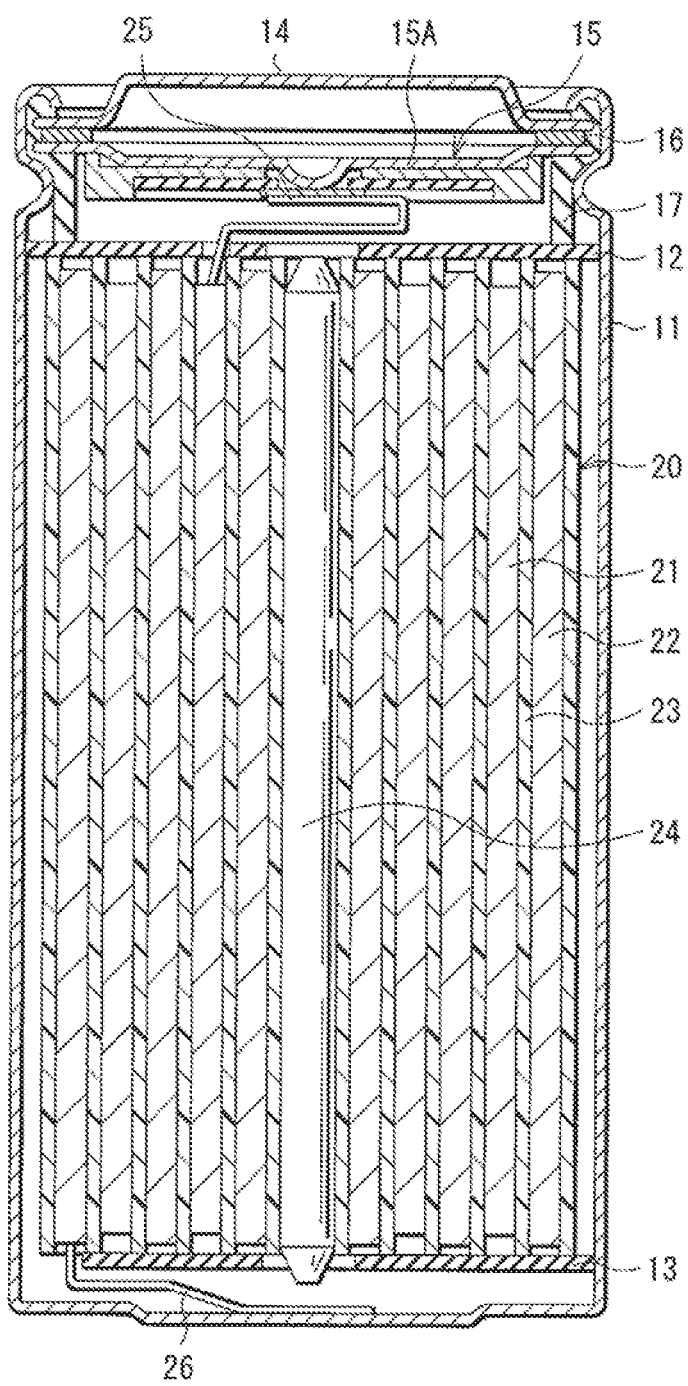
FIG. 1 is a cross-sectional view representing constituent features of a secondary battery (cylindrical type) of an embodiment of the present technology.

As described herein, the present disclosure will be described based on examples with reference to the drawings, but the present disclosure is not to be considered limited to the examples, and various numerical values and materials in the examples are considered by way of example.

First, an electrolytic solution for a secondary battery of one embodiment of the present technology will be illustrated.

An electrolytic solution for a secondary battery illustrated herein (hereinafter, simply referred to as "electrolytic solution") is used, for example, in a secondary battery such as a lithium ion secondary battery. However, a kind of the secondary battery in which the electrolytic solution is used is not limited to a lithium ion secondary battery.

The electrolytic solution contains any one or two or more kinds of sulfonyl compounds. That is, a kind of the sulfonyl compound may be only one kind, or may be two or more kinds.

Specifically, the sulfonyl compound includes any one or two or more kinds of compounds that are represented by each of the following chemical formula (1), chemical formula (2) and chemical formula (3).

[Chemical formula 1]

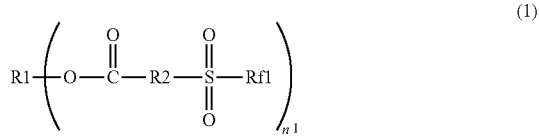
(1)

(R1 is any of an n1-valent hydrocarbon group, an n1-valent oxygen-containing hydrocarbon group, an n1-valent halogenated hydrocarbon group and an n1-valent halogenated oxygen-containing hydrocarbon group. R2 is any of a divalent hydrocarbon group and a divalent halogenated hydrocarbon group. Rf1 is any of a halogen group and a monovalent halogenated hydrocarbon group. n1 is an integer of 2 or more.)

[Chemical formula 2]

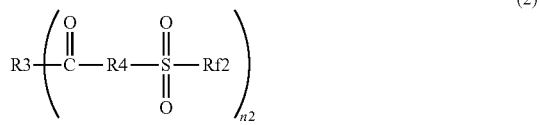
(2)

(R3 is any of an n2-valent hydrocarbon group, an n2-valent oxygen-containing hydrocarbon group, an n2-valent halogenated hydrocarbon group and an n2-valent halogenated oxygen-containing hydrocarbon group. R4 is any of a divalent hydrocarbon group and a divalent halogenated hydrocarbon group. Rf2 is any of a halogen group and a monovalent halogenated hydrocarbon group. n2 is an integer of 1 or more.)

[Chemical formula 3]

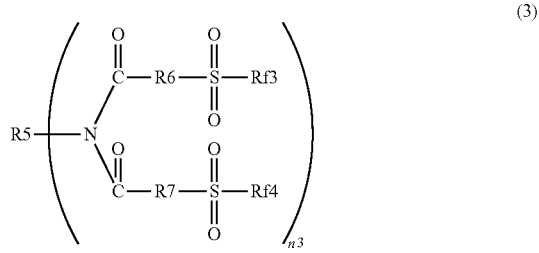
(3)

(R5 is any of an n3-valent hydrocarbon group, an n3-valent oxygen-containing hydrocarbon group, an n3-valent halogenated hydrocarbon group and an n3-valent halogenated oxygen-containing hydrocarbon group. Each of R6 and R7 is any of a divalent hydrocarbon group and a divalent halogenated hydrocarbon group. Each of Rf3 and Rf4 is any of a halogen group and a monovalent halogenated hydrocarbon group. n3 is an integer of 1 or more.)

In the following illustration, in order to discriminate the above-mentioned three kinds of compounds, the compound shown in the formula (1) is referred to as "first sulfonyl compound", the compound shown in the formula (2) is referred to as "second sulfonyl compound", and the compound shown in the formula (3) is referred to as "third sulfonyl compound".

Besides this, the first sulfonyl compound, the second sulfonyl compound and the third sulfonyl compound are collectively named generically as "sulfonyl compound".

The electrolytic solution contains the sulfonyl compound because the chemical stability of the electrolytic solution is improved. Since a decomposition reaction of the electrolytic solution is thereby suppressed and, at the same time, generation of the gas due to the decomposition reaction of the electrolytic solution is suppressed, the battery property of a secondary battery using the electrolytic solution is improved. In this case, particularly, even when the secondary battery is used (charged and discharged) in the severe environment such as the high temperature environment and the low temperature environment and, at the same time, the secondary battery is preserved in those environments, since the decomposition reaction of the electrolytic solution is sufficiently suppressed and, at the same time, generation of the gas is also sufficiently suppressed, the battery property is considerably improved.

The content of the sulfonyl compound in the electrolytic solution is not particularly limited, but is, for example, 0.01% by weight to 5% by weight, preferably 0.5% by weight to 5% by weight. This is because the chemical stability of the electrolytic solution is sufficiently improved while the solubility and the compatibility of the sulfonyl compound are ensured.

In addition, when the electrolytic solution contains two or more kinds of the sulfonyl compounds, the above-mentioned "content of the sulfonyl compound" is the sum of the contents of respective sulfonyl compounds.

In the first sulfonyl compound, as shown in the formula (1), two or more branch portions comprising a sulfonyl group (—O—C(=O)—R2-S(=O)$_2$—Rf1) are bound to a stem portion (R1). A kind of the first sulfonyl compound may be only one kind, or may be two or more kinds.

R1 is any of an n1-valent hydrocarbon group, an n1-valent oxygen-containing hydrocarbon group, an n1-valent halogenated hydrocarbon group and an n1-valent halogenated oxygen-containing hydrocarbon group, as described above.

The "n1-valent hydrocarbon group" is a generic name of a monovalent group that is formed of carbon and hydrogen, as described above. This n1-valent hydrocarbon group may be a linear chain, may be a branched chain having one or two or more branch portions, may be cyclic, or may be in the state where two or more kinds of them are mutually bound. Furthermore, the n1-valent hydrocarbon group may comprise one or two or more intercarbon unsaturated bonds (one or both of an intercarbon double bond and an intercarbon triple bond), or not comprise the intercarbon unsaturated bond.

The "n1-valent oxygen-containing hydrocarbon group" is a group in which one or two or more ether bonds are introduced in the middle of the n1-valent hydrocarbon group. The "n1-valent halogenated hydrocarbon group" is a group in which one or two or more hydrogen groups of the n1-valent hydrocarbon group are substituted with a halogen group. The "n1-valent halogenated oxygen-containing hydrocarbon group" is a group in which one or two or more hydrogen group of the n1-valent oxygen-containing hydrocarbon group are substituted with a halogen group.

As clear from the chemical formula (1), the valence of a stem portion (an n1-valent hydrocarbon group, an n1-valent oxygen-containing hydrocarbon group, an n1-valent halogenated hydrocarbon group and an n1-valent halogenated oxygen-containing hydrocarbon group, which are R1) is determined depending on the number (value of n1) of a branch portion (—O—C(=O)—R2-S(=O)$_2$—Rf1).

In this regard, since n1 is an integer of 2 or more as described above, the valence of a stem portion is 2 or more. That is, the n1-valent hydrocarbon group, the n1-valent oxygen-containing hydrocarbon group, the n1-valent halogenated hydrocarbon group and the n1-valent halogenated oxygen-containing hydrocarbon group are a di- or more valent hydrocarbon group, a di- or more valent oxygen-containing hydrocarbon group, a di- or more valent halogenated hydrocarbon group and a di- or more valent halogenated oxygen-containing hydrocarbon group.

As one example, when the number of branch portions is 2 (n1=2), the valence of a stem portion is 2. When the number of branch portions is 3 (n1=3), the valence of a stem portion is 3. When the number of branch portions is 4 (n1=4), the valence of a stem portion is 4. Of course, the valence of a stem portion can be 5 or more depending on the number of branch portions.

The n1-valent hydrocarbon group is, for example, a group in which n1 hydrogen groups are eliminated from a hydrocarbon, and the hydrocarbon is, for example, an alkane, an alkene, an alkyne, an alicyclic hydrocarbon, an aromatic hydrocarbon and a compound in which two or more kinds of them are mutually bound (hereinafter, referred to as "bound compound").

A kind of the alkane is not particularly limited, but is, for example, methane, ethane, propane, butane, pentane, hexane, heptane, octane, nonane and decane.

A kind of the alkene is not particularly limited, but is, for example, ethylene (ethene), propene (propylene), butene, pentene, hexene, heptene, octene, nonene and decene.

A kind of the alkyne is not particularly limited, but is, for example, ethyne (acetylene), propyne, butyne, pentyne, hexyne, heptyne, octyne, nonyne and decyne.

A kind of the alicyclic hydrocarbon is not particularly limited, but is, for example, cyclopropane, cyclobutane, cyclopentane, cyclohexane, cycloheptane, cyclooctane, cyclononane and cyclodecane.

A kind of the aromatic hydrocarbon is not particularly limited, but is, for example, benzene, naphthalene, anthracene, biphenyl and terphenyl.

A kind of the bound compound is not particularly limited, but is, for example, a compound in which an alkane and an alkene are mutually bound, a compound in which an alkane and an alkyne are mutually bound, a compound in which an alkene and an alkyne are mutually bound, a compound in which one or more kinds of an alkane, an alkene and an alkyne and an alicyclic hydrocarbon are mutually bound, a compound in which one or more kinds of an alkane, an alkene and an alkyne and an aromatic hydrocarbon are mutually bound, as well as a compound in which one or more kinds of an alkane, an alkene and an alkyne, an alicyclic hydrocarbon and an aromatic hydrocarbon are mutually bound.

In the case of n1=2, the n1-valent hydrocarbon group is a divalent hydrocarbon group, as described above. This divalent hydrocarbon group is, for example, a group in which two hydrogen groups are eliminated from each of an alkane, an alkene, an alkyne, an alicyclic hydrocarbon, an aromatic hydrocarbon and a bound compound. In this regard, a position at which a hydrogen atom is eliminated is not particularly limited. A position of elimination of a hydrogen group is not limited like this, and this also applies hereinafter.

The group in which two hydrogen groups are eliminated from an alkane is a so-called alkylene group. A kind of the alkylene group is not particularly limited, but is, for example, a methylene group, an ethylene group, a propylene group, a butylene group, a pentylene group, a hexylene group, a heptylene group, an octylene group, a nonylene group and a decylene group.

The group in which two hydrogen groups are eliminated from an alkene is a so-called alkenylene group. A kind of the alkenylene group is not particularly limited, but is, for example, an ethenylene group, a propenylene group, a butenylene group, a pentenylene group, a hexenylene group, a heptenylene group, an octenylene group, a nonenylene group and a decynylene group.

The group in which two hydrogen groups are eliminated from an alkyne is a so-called alkynylene group. A kind of the alkynylene group is not particularly limited, but is, for example, an ethynylene group, a propynylene group, a butynylene group, a pentynylene group, a hexynylene group, a heptynylene group, an octynylene group, a nonylylene group and a decynylene group.

The group in which two hydrogen groups are eliminated from an alicyclic hydrocarbon is a so-called cycloalkylene group. A kind of the cycloalkylene group is not particularly limited, but is, for example, a cyclopropylene group, a cyclobutylene group, a cyclopentylene group, a cyclohexylene group, a cycloheptylene group, a cyclooctylene group, a cyclononylene group and a cyclodecylene group. Besides this, the group in which two hydrogen groups are eliminated from an alicyclic hydrocarbon may be, for example, a cycloalkenylene group and a cycloalkynylene group. A kind of the cycloalkenylene group is not particularly limited, but is, for example, a cyclopropenylene group, and a kind of the cycloalkynylene group is not particularly limited, but is, for example, a cyclopropynylene group.

The group in which two hydrogen groups are eliminated from an aromatic hydrocarbon is a so-called arylene group. A kind of the arylene group is not particularly limited, but is, for example, a phenylene group and a naphthylene group.

In the case of n1=3, the n1-valent hydrocarbon group is a trivalent hydrocarbon group, as described above. This trivalent hydrocarbon group is, for example, a group in which three hydrogen groups are eliminated from each of an alkane, an alkene, an alkyne, an alicyclic hydrocarbon, an aromatic hydrocarbon and a bound compound.

Of course, when n1 is 4 or more, the n1-valent hydrocarbon group can be a tetra- or more valent hydrocarbon group.

The carbon number of the n1-valent hydrocarbon group is not particularly limited. Inter alia, when the n1-valent hydrocarbon group is a group in which n1 hydrogen groups are eliminated from each of an alkane, an alkene and an alkyne, it is preferable that the carbon number of the n1-valent hydrocarbon group is 1 to 12. This is because the chemical stability of the electrolytic solution is sufficiently improved while the solubility and the compatibility of the first sulfonyl compound are ensured.

The n1-valent oxygen-containing hydrocarbon group is a group in which one or two or more ether bonds are introduced into an n1-valent hydrocarbon group so as to divide the n1-valent hydrocarbon chain once or two or more times in the middle thereof.

Specific examples of the n1-valent oxygen-containing hydrocarbon group are as follows: Herein, the case where the n1-valent hydrocarbon group is a butylene group ($-CH_2-CH_2-CH_2-CH_2-$) that is an example of an alkylene group is given as an example.

When one ether bond is introduced into a butylene group, the n1-valent oxygen-containing hydrocarbon group may be, for example, $-CH_2-CH_2-O-CH_2-CH_2-$, or $-CH_2-O-CH_2-CH_2-CH_2-$.

When two ether bonds are introduced into a butylene group, the n1-valent oxygen-containing hydrocarbon group may be, for example, $-CH_2-O-CH_2-CH_2-O-CH_2-$, $-CH_2-O-CH_2-O-CH_2-CH_2-$, or $-CH_2-CH_2-O-CH_2-CH_2-$.

Of course, since the above-mentioned specific examples of the n1-valent oxygen-containing hydrocarbon group are just merely an example, the n1-valent oxygen-containing hydrocarbon group may be a group other than the above-mentioned series of groups.

Provided that when two or more ether bonds are contained in the n1-valent oxygen-containing hydrocarbon group, it is preferable that two ether bonds are not mutually bound directly like $-O-O-$, but are mutually bound indirectly like $-O-CH_2-O-$. This is because the first sulfonyl compound becomes easily producible, and at the same time, the first sulfonyl compound becomes chemically easily stabilizable.

The n1-valent halogenated hydrocarbon group is a group in which one or two or more hydrogen groups of the n1-valent hydrocarbon group are substituted with a halogen group, as described above.

A kind of the halogen group is not particularly limited, but is, for example, a fluorine group, a chlorine group, a bromine group and an iodine group, or may be a group other than them. When two or more halogen groups are contained in the n1-valent halogenated hydrocarbon group, a kind of the two or more halogen groups may be only one kind, or may be two or more kinds.

Inter alia, the halogen group is preferably a fluorine group. This is because the chemical stability of the electrolytic solution is sufficiently improved while the solubility and the compatibility of the first sulfonyl group are ensured.

When the n1-valent hydrocarbon group is a divalent hydrocarbon group, specific examples of the divalent halogenated hydrocarbon group are as follows:

When the divalent hydrocarbon group is an alkylene group, the divalent halogenated hydrocarbon group is, for example, a fluoromethylene group, a perfluoromethylene group, a perfluoroethylene group, a perfluoropropylene group, a perfluorobutylene group and a perfluorodecylene group.

When the divalent hydrocarbon group is an alkenylene group, the divalent halogenated hydrocarbon group is, for example, a perfluoroethylene group, a perfluoropropenylene group, a perfluorobutenylene group and a perfluorodecynylene group.

When the divalent hydrocarbon group is an alkynylene group, the divalent halogenated hydrocarbon group is, for example, a perfluoroethynylene group, a perfluoropropynylene group, a perfluorobutynylene group and a perfluorodecynylene group.

When the divalent hydrocarbon group is a cycloalkylene group, the divalent halogenated hydrocarbon group is, for example, a perfluorocyclopropylene group, a perfluorocyclobutylene group and a perfluorocyclodecylene group.

When the divalent hydrocarbon group is an aromatic hydrocarbon, the divalent halogenated hydrocarbon group is, for example, a perfluorophenylene group and a perfluoronaphthylene group.

When the n1-valent hydrocarbon group is a trivalent hydrocarbon group, specific examples of the trivalent halogenated hydrocarbon group are a group in which one hydrogen group or one fluorine group is eliminated from the above-mentioned specific examples of the divalent halogenated hydrocarbon group.

Of course, since the above-mentioned specific examples of the n1-valent halogenated hydrocarbon group are just merely an example, the n1-valent halogenated hydrocarbon group may be a group other than the above-mentioned series of groups.

The n1-valent halogenated oxygen-containing hydrocarbon group is a group in which one or two or more hydrogen groups of the n1-valent oxygen-containing hydrocarbon group are substituted with a halogen group, as described above. Details regarding the halogen group are, for example, as described above.

When the n1-valent oxygen-containing hydrocarbon group is a divalent oxygen-containing hydrocarbon group, specific examples of the divalent halogenated oxygen-containing hydrocarbon group are $-CH_2-CF_2-O-CH_2-CF_2-$, $-CF_2-CF_2-O-CF_2-CF_2-$, $-CF_2-O-CF_2-CF_2-CF_2-$, $-CF_2-O-CF_2-CF_2-O-CF_2-$ and $-CF_2-O-CF_2-O-CF_2-CF_2-$.

When the n1-valent oxygen-containing hydrocarbon group is a trivalent oxygen-containing hydrocarbon group, specific examples of the trivalent halogenated oxygen-containing hydrocarbon group are a group in which one hydrogen group or two fluorine groups is (are) eliminated from the above-mentioned specific examples of the divalent halogenated oxygen-containing hydrocarbon group.

Of course, since the above-mentioned specific examples of the n1-valent halogenated oxygen-containing hydrocarbon group are just merely an example, the n1-valent halogenated oxygen-containing hydrocarbon group may be a group other than the above-mentioned series of groups.

R2 is any of a divalent hydrocarbon group and a divalent halogenated hydrocarbon group, as described above.

The "divalent hydrocarbon group" is a generic name of a divalent group that is formed of carbon and hydrogen, as described above. This divalent hydrocarbon group may be a linear chain, may be a branched chain having one or two or more branch portions, may be cyclic, or may be in the state where two or more kinds of them are mutually bound. Furthermore, the divalent hydrocarbon group may comprise one or two or more intercarbon unsaturated bonds, or need not comprise the intercarbon unsaturated bond.

A kind of the divalent hydrocarbon group is not particularly limited, but is, for example, an alkylene group, an alkenylene group, an alkynylene group, a cycloalkylene group, an arylene group and a divalent group in which two or more kinds of them are bound (hereinafter, referred to as "divalent bound group").

Details regarding each of the alkylene group, the alkenylene group, the alkynylene group, the cycloalkylene group and the arylene group are, for example, as described above.

A kind of the divalent bound group is not particularly limited, but is, for example, a divalent group in which an alkylene group and an alkenylene group are mutually bound, a divalent group in which an alkylene group and an alkynylene group are mutually bound, a divalent group in which an alkenylene group and an alkynylene group are mutually bound, a divalent group in which a cycloalkylene group and an arylene group are mutually bound, a divalent group in which one or more kinds of an alkylene group, an alkenylene group and an alkynylene group and a cycloalkylene group are mutually bound, a divalent group in which one or more kinds of an alkylene group, an alkenylene group and an alkynylene group and an arylene group are mutually bound, as well as a divalent group in which one or more kinds of an alkylene group, an alkenylene group and an alkynylene group, a cycloalkylene group and an arylene group are mutually bound.

Inter alia, the divalent hydrocarbon group is preferably an alkylene group. This is because the chemical stability of the electrolytic solution is sufficiently improved while the solubility and the compatibility of the first sulfonyl compound are ensured.

The carbon number of the divalent hydrocarbon group is not particularly limited. Specifically, the carbon number of the alkylene group is, for example, 1 to 10. The carbon number of each of the alkenylene group and the alkynylene group is, for example, 2 to 10. The carbon number of each of the cycloalkylene group and the arylene group is, for example, 6 to 18. This is because the chemical stability of the electrolytic solution is sufficiently improved while the solubility and the compatibility of the first sulfonyl compound are ensured.

Inter alia, the carbon number of each of the alkylene group, the alkenylene group and the alkynylene group is more preferably 1 to 4. This is because the solubility and the compatibility of the first sulfonyl compound are more improved.

The "divalent halogenated hydrocarbon group" is a group in which one or two or more hydrogen groups of the divalent hydrocarbon group are substituted with a halogen group, as described above. Details regarding the halogen group are, for example, as described above. That is, a kind of the halogen group is, for example, a fluorine group, a chlorine group, a bromine group and an iodine group, and inter alia, the halogen group is preferably a fluorine group.

Specific examples of the divalent halogenated hydrocarbon group are as follows:

When the divalent hydrocarbon group is an alkylene group, the divalent halogenated hydrocarbon group is, for example, a fluoromethylene group, a perfluoromethylene group, a perfluoroethylene group, a perfluoropropylene group, a perfluorobutylene group and a perfluorodecylene group.

When the divalent hydrocarbon group is an alkenylene group, the divalent halogenated hydrocarbon group is, for example, a perfluoroethylene group, a perfluoropropenylene group, a perfluorobutenylene group and a perfluorodecynylene group.

When the divalent hydrocarbon group is an alkynylene group, the divalent halogenated hydrocarbon group is, for example, a perfluoroethynylene group, a perfluoropropynylene group, a perfluorobutynylene group and a perfluorodecynylene group.

When the divalent hydrocarbon group is a cycloalkylene group, the divalent halogenated hydrocarbon group is, for example, a perfluorocyclopropylene group, a perfluorocyclobutylene group and a perfluorocyclodecylene group.

When the divalent hydrocarbon group is an aromatic hydrocarbon, the divalent halogenated hydrocarbon group is, for example, a perfluorophenylene group and a perfluoronaphthylene group.

Of course, since the above-mentioned specific examples of the divalent halogenated hydrocarbon group are just merely an example, the divalent halogenated hydrocarbon group may be a group other than the above-mentioned series of groups.

Inter alia, the divalent halogenated hydrocarbon group is preferably a group in which one or two or more hydrogen groups of each of the alkylene group, the alkenylene group and the alkynylene group are substituted with a halogen group, more preferably a group in which one or two or more hydrogen groups of the alkylene group are substituted with a halogen group. This is because the chemical stability of the electrolytic solution is sufficiently improved while the solubility and the compatibility of the first sulfonyl compound are ensured.

Details regarding the carbon number of the divalent halogenated hydrocarbon group are, for example, the same as the above-mentioned details regarding the carbon number of the divalent hydrocarbon group, except that the divalent hydrocarbon group is halogenated.

Rf1 is any of a halogen group and a monovalent halogenated hydrocarbon group, as described above.

Details regarding the halogen group are, for example, as described above. That is, a kind of the halogen group is, for example, a fluorine group, a chlorine group, a bromine group and an iodine group, and inter alia, the halogen group is preferably a fluorine group.

The "monovalent halogenated hydrocarbon group" is a group in which one or two or more hydrogen groups of a monovalent hydrocarbon group are substituted with a halogen group, as described above, and the "monovalent hydrocarbon group" is a generic name of a monovalent group that is formed of carbon and hydrogen.

This monovalent hydrocarbon group may be a linear chain, may be a branched chain having one or two or more branch portions, may be cyclic, or may be in the state where two or more kinds of them are mutually bound. Furthermore, the monovalent hydrocarbon group may comprise one or two or more intercarbon unsaturated bonds, or need not comprise the intercarbon unsaturated bond.

A kind of the monovalent hydrocarbon group is not particularly limited, but is, for example, an alkyl group, an alkenyl group, an alkynyl group, a cycloalkyl group, an aryl group and a monovalent group in which two or more kinds of them are bound (hereinafter, referred to as "monovalent bound group").

A kind of the alkyl group is not particularly limited, but is, for example, a methyl group, an ethyl group, a propyl group, a butyl group, a pentyl group, a hexyl group, a heptyl group, an octyl group, a nonyl group and a decyl group.

A kind of the alkenyl group is not particularly limited, but is, for example, an ethenyl group, a propenyl group, a butenyl group, a pentenyl group, a hexenyl group, a heptenyl group, an octenyl group, a nonenyl group and a decynyl group.

A kind of the alkynyl group is not particularly limited, but is, for example, an ethynyl group, a propynyl group, a butynyl group, a pentynyl group, a hexynyl group, a heptynyl group, an octynyl group, a nonylyl group and a decyl group.

A kind of the cycloalkyl group is not particularly limited, but is, for example, a cyclopropyl group, a cyclobutyl group, a cyclopentyl group, a cyclohexyl group, a cycloheptyl group, a cyclooctyl group, a cyclononyl group and a cyclodecyl group.

A king of the aryl group is not particularly limited, but is, for example, a phenyl group and a naphthyl group.

A kind of the monovalent bound group is not particularly limited, but is, for example, a group in which an alkyl group and an alkenyl group are mutually bound, a group in which an alkyl group and alkynyl are mutually bound, a group in which an alkenyl group and an alkynyl group are mutually bound, a group in which a cycloalkyl group and an aryl group are mutually bound, a group in which one or more kinds of an alkyl group, an alkenyl group and an alkynyl group and a cycloalkyl group are mutually bound, a group in which one or more kinds of an alkyl group, an alkenyl group and an alkynyl group and an aryl group are mutually bound, as well as a group in which one or more kinds of an alkyl group, an alkenyl group and an alkynyl group, a cycloalkyl group and an aryl group are mutually bound.

Inter alia, the monovalent hydrocarbon group is preferably an alkyl group. This is because the chemical stability of the electrolytic solution is sufficiently improved while the solubility and the compatibility of the first sulfonyl compound are ensured.

The carbon number of the monovalent hydrocarbon group is not particularly limited. Specifically, the carbon number of an alkyl group is, for example, 1 to 10. The carbon number of each of an alkenyl group and an alkynyl group is, for example, 2 to 10. The carbon number of each of a cycloalkyl group and an aryl group is, for example, 6 to 18. This is because the chemical stability of the electrolytic solution is sufficiently improved while the solubility and the compatibility of the first sulfonyl compound are ensured.

Inter alia, it is more preferable that the carbon number of each of an alkyl group, an alkenyl group, and alkynyl is 1 to 4. This is because the solubility and the compatibility of the first sulfonyl compound are more improved.

Specific examples of the monovalent halogen hydrocarbon group are as follows:

When the monovalent hydrocarbon group is an alkyl group, the monovalent halogenated hydrocarbon group is, for example, a fluoromethyl group, a perfluoromethyl group, a perfluoroethyl group, a perfluoropropyl group, a perfluorobutyl group and a perfluorodecyl group.

When the monovalent hydrocarbon group is an alkenyl group, the monovalent halogenated hydrocarbon group is, for example, a perfluoroethenyl group, a perfluoropropenyl group, a perfluorobutenyl group and a perfluorodecynyl group.

When the monovalent hydrocarbon group is an alkynyl group, the monovalent halogenated hydrocarbon group is, for example, a perfluoroethynyl group, a perfluoropropynyl group, a perfluorobutynyl group and a perfluorodecynyl group.

When the monovalent hydrocarbon group is a cycloalkyl group, the monovalent halogenated hydrocarbon group is, for example, a perfluorocyclopropyl group, a perfluorocyclobutyl group and a perfluorocyclodecyl group.

When the monovalent hydrocarbon group is aryl, the monovalent halogenated hydrocarbon group is, for example, a perfluorophenyl group and a perfluoronaphthyl group.

Of course, since the above-mentioned specific examples of the monovalent halogenated hydrocarbon group are just merely an example, the monovalent halogenated hydrocarbon group may be a group other than the above-mentioned series of groups.

Inter alia, the monovalent halogenated hydrocarbon group is preferably a group in which one or two or more hydrogen groups of each of an alkyl group, an alkenyl group and an alkynyl group are substituted with a halogen group, more preferably a group in which one or two or more hydrogen groups of an alkyl group are substituted with a halogen group, further preferably a perfluoroalkyl group. This is because the chemical stability of the electrolytic solution is sufficiently improved while the solubility and the compatibility of the first sulfonyl compound are ensured.

Details regarding the carbon number of the monovalent halogenated hydrocarbon group are, for example, the same as the above-mentioned details regarding the carbon number of the monovalent hydrocarbon group, except that the monovalent hydrocarbon group is halogenated.

As described above, $n1$ is an integer of 2 or more. For this reason, a value of $n1$ is not particularly limited as long as it is an integer of 2 or more. Depending on this value of $n1$, the valence of a stem portion (R1) is determined, and at the same time, the number of branch portions (—O—C(=O)—R2-S(=O)$_2$—Rf1) bound to the stem portion is determined.

The reason that $n1$ is 2 or more is because the chemical stability of the electrolytic solution is sufficiently improved, a decomposition reaction of the electrolytic solution is sufficiently suppressed, unlike the case where $n1$ is 1.

In particular, when $n1$ is 1, since the chemical stability of the electrolytic solution is not sufficiently improved, a decomposition reaction of the electrolytic solution is not sufficiently suppressed. In this case, when the secondary battery is used (charged and discharged) in the severe environment such as the high temperature environment and the low temperature environment, and at the same time, the secondary battery is preserved in those environments, since the electrolytic solution becomes remarkably easily decomposable, the discharge capacity becomes easily reducible considerably. Moreover, since the gas due to the decomposition reaction of the electrolytic solution becomes easily generatable at a large amount in the interior of the secondary battery, the secondary battery becomes easily swellable.

In contrast, when $n1$ is 2 or more, since the chemical stability of the electrolytic solution is sufficiently improved, the decomposition reaction of the electrolytic solution is sufficiently suppressed. In this case, even when the secondary battery is used in the severe environment such as the high temperature environment and the low temperature environment, and at the same time, the secondary battery is preserved in those environments, since the electrolytic solution becomes hardly decomposable, reduction in the discharge capacity is considerably suppressed. Moreover, since the gas due to the decomposition reaction of the electrolytic solution becomes hardly generatable in the interior of the secondary battery, the secondary battery becomes hardly swellable.

Inter alia, it is preferable that $n1$ is 4 or less. That is, it is preferable that $n1$ is an integer of 1 to 4. This is because the chemical stability of the electrolytic solution is sufficiently improved while the solubility and the compatibility of the first sulfonyl compound are ensured.

In the second sulfonyl compound, as shown in the formula (2), two or more branch portions comprising a sulfonyl group (—C(=O)—R4-S(=O)$_2$—Rf2) are bound to a stem portion (R3). A kind of the second sulfonyl compound may be only one kind, or may be two or more kinds.

R3 is any of an $n2$-valent hydrocarbon group, an $n2$-valent oxygen-containing hydrocarbon group, an $n2$-valent halogenated hydrocarbon group and an $n2$-valent halogenated oxygen-containing hydrocarbon group, as described above.

Details regarding each of the "$n2$-valent hydrocarbon group, the $n2$-valent oxygen-containing hydrocarbon group, the $n2$-valent halogenated hydrocarbon group and the $n2$-valent halogenated oxygen-containing hydrocarbon group" are, for example, the same as the above-mentioned details regarding each of the $n1$-valent hydrocarbon group, the n1-valent oxygen-containing hydrocarbon group, the n1-valent halogenated hydrocarbon group and the n1-valent halogenated oxygen-containing hydrocarbon group, except that the valence is different (it is not n1, but n2).

That is, the n2-valent hydrocarbon group is, for example, a group in which n2 hydrogen groups are eliminated from a hydrocarbon. The n2-valent oxygen-containing hydrocarbon group is, for example, a group in which one or two or more ether bonds are introduced into the middle of a n2-valent hydrocarbon group. The n2-valent halogenated hydrocarbon group is, for example, a group in which one or two or more hydrogen groups of the n2-valent hydrocarbon group are substituted with a halogen group. The n2-valent halogenated oxygen-containing hydrocarbon group is, for example, a group in which one or two or more hydrogen groups of the n2-valent oxygen-containing hydrocarbon group are substituted with a halogen group.

Provided that, unlike the first sulfonyl compound in which n1 is 2 or more, since in the second sulfonyl compound, n2 is 1 or more, the n2-valent hydrocarbon group, the n2-valent oxygen-containing hydrocarbon group, the n2-valent halogenated hydrocarbon group and the n2-valent halogenated oxygen-containing hydrocarbon group can be a monovalent hydrocarbon group, a monovalent oxygen-containing hydrocarbon group, a monovalent halogenated hydrocarbon group and a monovalent halogenated oxygen-containing hydrocarbon group.

The monovalent hydrocarbon group is a group in which one hydrogen group is eliminated from each of an alkane, an alkene, an alkyne, an alicyclic hydrocarbon, an aromatic hydrocarbon and a bound compound. The group in which one hydrogen group is eliminated from an alkane is a so-called alkyl group. The group in which one hydrogen group is eliminated from an alkene is a so-called alkenyl group. The group in which one hydrogen group is eliminated from an alkyne is a so-called alkynyl group. The group in which one hydrogen group is eliminated from an alicyclic hydrocarbon is a so-called cycloalkyl group, and may be a cycloalkenyl group and a cycloalkynyl group. The group in which one hydrogen group is eliminated from an aromatic hydrocarbon is a so-called aryl group. The group in which one hydrogen group is eliminated from a bound compound is a so-called monovalent bound group. Details regarding each of the alkyl group, the alkenyl group, the alkynyl group, the cycloalkyl group, the cycloalkenyl group, the cycloalkynyl group, the aryl group and the monovalent bound group are, for example, as described above.

The monovalent oxygen-containing hydrocarbon group is a group in which one or two or more ether bonds are introduced into the middle of a monovalent hydrocarbon group. The monovalent halogenated hydrocarbon group is a group in which one or two or more hydrogen groups of a monovalent hydrocarbon group are substituted with a halogen group. The monovalent halogenated oxygen-containing hydrocarbon group is a group in which one or two or more hydrogen groups of a monovalent oxygen-containing hydrocarbon group are substituted with a halogen group. In addition, details regarding the halogen group are, for example, as described above.

As clear from the chemical formula (2), the valence of a stem portion (an n2-valent hydrocarbon group, an n2-valent oxygen-containing hydrocarbon group, an n2-valent halogenated hydrocarbon group and an n2-valent halogenated oxygen-containing hydrocarbon group, which are R3) is determined depending on the number (value of n2) of a branch portion (—C(=O)—R4-S(=O)$_2$—Rf2).

The carbon number of the n2-valent hydrocarbon group is not particularly limited. Inter alia, when the n2-valent hydrocarbon group is a group in which n2 hydrogen groups are eliminated from any of an alkane, an alkene and an alkyne, the carbon number of the n2-valent hydrocarbon group is preferably 1 to 12. This is because the chemical stability of the electrolytic solution is sufficiently improved while the solubility and the compatibility of the second sulfonyl compound are ensured.

R4 is any of a divalent hydrocarbon group and a divalent halogenated hydrocarbon group, as described above. Details regarding R4 are, for example, the same as the above-mentioned details regarding R2.

That is, the divalent hydrocarbon group is, for example, an alkylene group, an alkenylene group, an alkynylene group, a cycloalkylene group, an arylene group and a divalent bound group. Furthermore, the divalent halogenated hydrocarbon group is, for example, a group in which one or two or more hydrogen groups of the divalent hydrocarbon group are substituted with a halogen group.

Rf2 is any of a halogen group and a monovalent halogenated hydrocarbon group, as described above. Details regarding Rf2 are, for example, the same as the above-mentioned details regarding Rf1.

That is, the halogen group is, for example, a fluorine group, a chlorine group, a bromine group and an iodine group. The divalent halogenated hydrocarbon group is, for example, a group in which one or two or more hydrogen groups of the divalent hydrocarbon group are substituted with a halogen group.

As described above, n2 is an integer of 1 or more, unlike the above-mentioned n1. For this reason, a value of n2 is not particularly limited as long as it is an integer of 1 or more. Depending on this value of n2, the valence of a stem portion (R3) is determined, and at the same time, the number of a branch portion (—C(=O)—R4-S(=O)$_2$—Rf2) bound to the stem portion is determined.

The reason that n2 is an integer of 1 or more is because when the second sulfonyl compound is used, since even when a value of n2 is 1, the chemical stability of the electrolytic solution is sufficiently improved like the case where a value of n2 is 2 or more, a decomposition reaction of the electrolytic solution is sufficiently suppressed, unlike the case where the first sulfonyl compound is used.

Inter alia, n2 is preferably 2 or more. That is, n2 is preferably an integer of 2 or more. This is because the chemical stability of the electrolytic solution is sufficiently improved while the solubility and the compatibility of the second sulfonyl compound are ensured.

Furthermore, n2 is preferably 4 or less. That is, n2 is preferably an integer of 4 or less. This is because the chemical stability of the electrolytic solution is sufficiently improved while the solubility and the compatibility of the second sulfonyl compound are ensured.

In the third sulfonyl compound, as shown in the formula (3), two or more branch portions comprising a sulfonyl group (Rf3-S(=O)$_2$—R6-C(=O)—N<C(=O)—R7-S(=O)$_2$—Rf4) are bound to a stem portion (R5). A kind of the third sulfonyl compound may be only one kind, or may be two or more kinds.

R5 is any of an n3-valent hydrocarbon group, an n3-valent oxygen-containing hydrocarbon group, an n3-valent halogenated hydrocarbon group and an n3-valent halogenated oxygen-containing hydrocarbon group, as described above.

Details regarding each of the "n3-valent hydrocarbon group, the n3-valent oxygen-containing hydrocarbon group, the n3-valent halogenated hydrocarbon group and the n3-valent halogenated oxygen-containing hydrocarbon group" are, for example, the same as the above-mentioned details regarding each of the n2-valent hydrocarbon group, the n2-valent oxygen-containing hydrocarbon] group, the n2-valent halogenated hydrocarbon group and the n2-valent halogenated oxygen-containing hydrocarbon group, except that the valence is different (it is not n2, but n3).

That is, the n3-valent hydrocarbon group is, for example, a group in which n3 hydrogen groups are eliminated from a hydrocarbon. The n3-valent oxygen-containing hydrocarbon group is, for example, a group in which one or two or more ether bonds are introduced into the middle of the n3-valent hydrocarbon group. The n3-valent halogenated hydrocarbon group is a group in which one or two or more hydrogen groups of the n3-valent hydrocarbon group are substituted with a halogen group. The n3-valent halogenated oxygen-containing hydrocarbon group is, for example, a group in which one or two or more hydrogen groups of the n3-valent oxygen-containing hydrocarbon group are substituted with a halogen group.

Provided that since in the third sulfonyl compound, n3 is 1 or more, the n3-valent hydrocarbon group, the n3-valent oxygen-containing hydrocarbon group, the n3-valent halogenated hydrocarbon group and the n3-valent halogenated oxygen-containing hydrocarbon group can be a monovalent hydrocarbon group, a monovalent oxygen-containing hydrocarbon group, a monovalent halogenated hydrocarbon group and a monovalent halogenated oxygen-containing hydrocarbon group. Details regarding each of the monovalent hydrocarbon group, the monovalent oxygen-containing hydrocarbon group, the monovalent halogenated hydrocarbon group and the monovalent halogenated oxygen-containing hydrocarbon group are, for example, as described above.

As clear from the chemical formula (3), the valence of a stem portion (each of an n3-valent hydrocarbon group, an n3-valent oxygen-containing hydrocarbon group, an n3-valent halogenated hydrocarbon group and an n3-valent halogenated oxygen-containing hydrocarbon group, which are R5) is determined depending on the number (a value of n3) of a branch portion (Rf3-S(=O)$_2$—R6-C(=O)—N<C (=O)—R7-S(O)$_2$—Rf4).

The carbon number of the n3-valent hydrocarbon group is not particularly limited. Inter alia, when the n3-valent hydrocarbon group is a group in which n3 hydrogen groups are eliminated from each of an alkane, an alkene and an alkyne, the carbon number of the n3-valent hydrocarbon group is preferably 1 to 12. This is because the chemical stability of the electrolytic solution is sufficiently improved while the solubility and the compatibility of the third sulfonyl compound are ensured.

Based on the same reason as that of n2 described above, n3 is an integer of 1 or more.

Each of R6 and R7 is any of a divalent hydrocarbon group and a divalent halogenated hydrocarbon group, as described above. Details regarding each of R6 and R7 are, for example, the same as the above-mentioned details regarding R2.

That is, the divalent hydrocarbon group is, for example, an alkylene group, an alkenylene group, an alkynylene group, a cycloalkylene group, an arylene group and a divalent bound group. Furthermore, the divalent halogenated hydrocarbon group is, for example, a group in which one or two or more hydrogen groups of the above-mentioned divalent hydrocarbon group are substituted with a halogen group.

Each of Rf3 and Rf4 is any of a halogen group and a monovalent halogenated hydrocarbon group, as described above. Details regarding each of Rf3 and Rf4 are, for example, the same as the above-mentioned details regarding Rf1.

That is, the halogen group is, for example, a fluorine group, a chlorine group, a bromine group and an iodine group. The divalent halogenated hydrocarbon group is, for example, a group in which one or two or more hydrogen groups of the above-mentioned divalent hydrocarbon group are substituted with a halogen group.

As described above, n3 is an integer of 1 or more, unlike the above-mentioned n1. For this reason, a value of n3 is not particularly limited as long as it is an integer of 1 or more. Depending on this value of n3, the valence of a stem portion (R3) is determined, and at the same time, the number of a branch portion (Rf3-S(=O)$_2$—R6-C(=O)—N<C(=O)—R7-S(=O)$_2$—Rf4) bound to the stem portion is determined.

The reason that n3 is an integer of 1 or more is because when the third sulfonyl compound is used, the chemical stability of the electrolytic solution is sufficiently improved even when a value of n3 is 1, like the case where a value of n3 is 2 or more, a decomposition reaction of the electrolytic solution is sufficiently suppressed, unlike the case where the first sulfonyl compound is used.

Inter alia, n3 is preferably 2 or more. That is, n3 is preferably an integer of 2 or more. This is because the chemical stability of the electrolytic solution is sufficiently improved while the solubility and the compatibility of the third sulfonyl compound are ensured.

Furthermore, n3 is preferably 4 or less. That is, n3 is preferably an integer of 4 or less. This is because the chemical stability of the electrolytic solution is sufficiently improved while the solubility and the compatibility of the third sulfonyl compound are ensured.

Inter alia, it is preferable that the sulfonyl compound includes the following compounds. This is because the sulfonyl compound is easily produced, and at the same time, the chemical stability of the electrolytic solution is sufficiently improved.

Specifically, it is preferable that the first sulfonyl compound includes one or both of compounds that are represented by each of the following chemical formula (4) and chemical formula (5). It is preferable that the second sulfonyl compound includes one or both of compounds that are represented by each of the following formula chemical (6) and chemical formula (7). It is preferable that the third sulfonyl compound includes one or both of compounds that are represented by each of the following chemical formula (8) and chemical formula (9).

[Chemical formula 4]

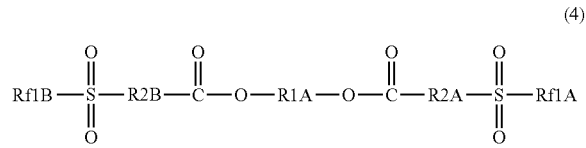

(4)

(R1A is any of a divalent hydrocarbon group, a divalent oxygen-containing hydrocarbon group, a divalent halogenated hydrocarbon group and a divalent halogenated oxygen-containing hydrocarbon group. Each of R2A and R2B is any of a divalent hydrocarbon group and a divalent halogenated hydrocarbon group. Each of Rf1A and Rf1B is any of a halogen group and a monovalent halogenated hydrocarbon group.)

[Chemical formula 5]

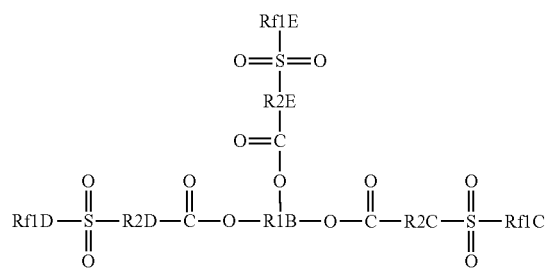

(5)

(R1B is any of a trivalent hydrocarbon group, a trivalent oxygen-containing hydrocarbon group, a trivalent halogenated hydrocarbon group and a trivalent halogenated oxygen-containing hydrocarbon group. Each of R2C, R2D and R2E is any of a divalent hydrocarbon group and a divalent halogenated hydrocarbon group. Each of Rf1C, Rf1D and Rf1E is any of a halogen group and a monovalent halogenated hydrocarbon group.)

[Chemical formula 6]

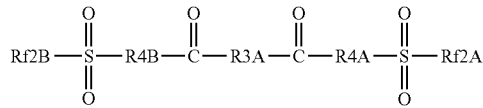

(6)

(R3A is any of a divalent hydrocarbon group, a divalent oxygen-containing hydrocarbon group, a divalent halogenated hydrocarbon group and a divalent halogenated oxygen-containing hydrocarbon group. Each of R4A and R4B is any of a divalent hydrocarbon group and a divalent halogenated hydrocarbon group. Each of Rf2A and Rf2B is any of a halogen group and a monovalent halogenated hydrocarbon group.)

[Chemical formula 7]

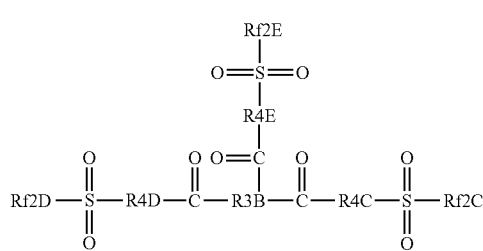

(7)

(R3B is any of a trivalent hydrocarbon group, a trivalent oxygen-containing hydrocarbon group, a trivalent halogenated hydrocarbon group and a trivalent halogenated oxygen-containing hydrocarbon group. Each of R4C, R4D and R4E is any of a divalent hydrocarbon group and a divalent halogenated hydrocarbon group. Each of Rf2C, Rf2D and Rf2E is any of a halogen group and a monovalent halogenated hydrocarbon group.)

[Chemical formula 8]

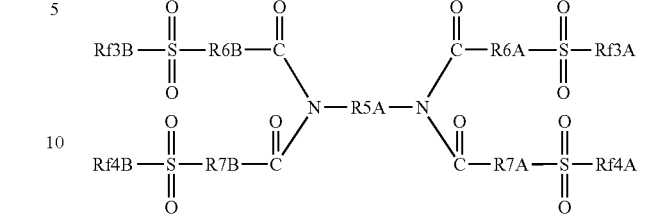

(8)

(R5A is any of a divalent hydrocarbon group, a divalent oxygen-containing hydrocarbon group, a divalent halogenated hydrocarbon group and a divalent halogenated oxygen-containing hydrocarbon group. Each of R6A, R6B, R7A and R7B is any of a divalent hydrocarbon group and a divalent halogenated hydrocarbon group. Each of Rf3A, Rf3B, Rf4A and Rf4B is any of a halogen group and a monovalent halogenated hydrocarbon group.)

[Chemical formula 9]

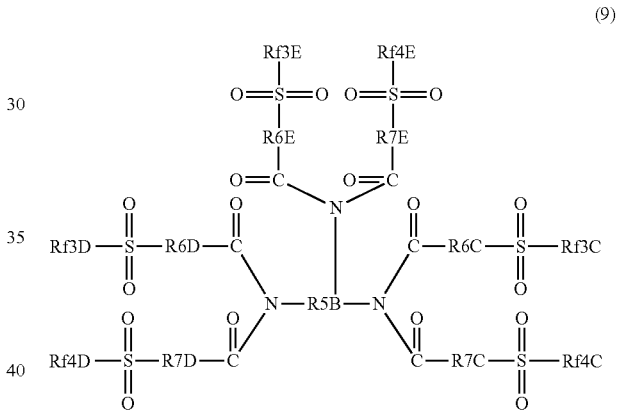

(9)

(R5B is any of a trivalent hydrocarbon group, a trivalent oxygen-containing hydrocarbon group, a trivalent halogenated hydrocarbon group and a trivalent halogenated oxygen-containing hydrocarbon group. Each of R6C, R6D, R6E, R7C, R7D and R7E is any of a divalent hydrocarbon group and a divalent halogenated hydrocarbon group. Each of Rf3C, Rf3D, Rf3E, Rf4C, Rf4D and Rf4E is any of a halogen group and a monovalent halogenated hydrocarbon group.)

The compound shown in the chemical formula (4) is a compound in which n1=2 in the chemical formula (1). That is, in the compound illustrated herein, two branch portions (—O—C(=O)—R2A-S(=O)$_2$—Rf1A and —O—C(=O)—R2B—S(=O)$_2$—Rf1B) are bound to a stem group (R1A).

Details regarding R1A (a divalent hydrocarbon group, a divalent oxygen-containing hydrocarbon group, a divalent halogenated hydrocarbon group and a divalent halogenated oxygen-containing hydrocarbon group) are, for example, the same as the above-mentioned details regarding R1 (an n-valent hydrocarbon group, an n-valent oxygen-containing hydrocarbon group, an n-valent halogenated hydrocarbon group and an n-valent halogenated oxygen-containing hydrocarbon group), except that the valence is limited to divalence. Details regarding each of R2A and R2B are, for example, the same as the above-mentioned details regarding R2. Details regarding Rf1A and Rf1B are, for example, the same as the above-mentioned details regarding Rf1.

The compound shown in the chemical formula (5) is a compound in which n1=3 in the formula (1). That is, in the compound illustrated herein, three branch portions (—O—C(=O)—R2C—S(=O)$_2$—Rf1C, —O—C(=O)—R2D-S(=O)$_2$—Rf1D and —O—C(=O)—R2E-S(=O)$_2$—Rf1E) are bound to a stem portion (R1B).

Details regarding R1B (a trivalent hydrocarbon group, a trivalent oxygen-containing hydrocarbon group, a trivalent halogenated hydrocarbon group and a trivalent halogenated oxygen-containing hydrocarbon group) are, for example, the same as the above-mentioned details regarding R1 (an n-valent hydrocarbon group, an n-valent oxygen-containing hydrocarbon group, an n-valent halogenated hydrocarbon group and an n-valent halogenated oxygen-containing hydrocarbon group), except that the valence is limited to trivalence. Details regarding each of R2C, R2D and R2E are, for example, the same as the above-mentioned details regarding R2. Details regarding Rf1C, Rf1D and Rf1E are, for example, the same as the above-mentioned details regarding Rf1.

The compound shown in the chemical formula (6) is a compound in which n2=2 in the chemical formula (2). That is, in the compound illustrated herein, two branch portions (—O—C(=O)—R4A-S(=O)$_2$—Rf2A and —O—C(=O)—R4B—S(=O)$_2$—Rf2B) are bound to a stem portion (R3A).

Details regarding R3A (a divalent hydrocarbon group, a divalent oxygen-containing hydrocarbon group, a divalent halogenated hydrocarbon group and a divalent halogenated oxygen-containing hydrocarbon group) are, for example, the same as the above-mentioned details regarding R1 (an n-valent hydrocarbon group, an n-valent oxygen-containing hydrocarbon group, an n-valent halogenated hydrocarbon group and an n-valent halogenated oxygen-containing hydrocarbon group), except that the valence is limited to divalence. Details regarding each of R4A and R4B are, for example, the same as the above-mentioned details regarding R2. Details regarding Rf2A and Rf2B are, for example, the same as the above-mentioned details regarding Rf1.

The compound shown in the chemical formula (7) is a compound in which n2=3 in the chemical formula (2). That is, in the compound illustrated herein, three branch portions (—O—C(=O)—R4C—S(=O)$_2$—Rf2C, —O—C(=O)—R4D-S(=O)$_2$—Rf2D and —O—C(=O)—R4E-S(=O)$_2$—Rf2E) are bound to a stem portion (R3B).

Details regarding R3B (a trivalent hydrocarbon group, a trivalent oxygen-containing hydrocarbon group, a trivalent halogenated hydrocarbon group and a trivalent halogenated oxygen-containing hydrocarbon group) are, for example, the same as the above-mentioned details regarding R1 (an n-valent hydrocarbon group, an n-valent oxygen-containing hydrocarbon group, an n-valent halogenated hydrocarbon group and an n-valent halogenated oxygen-containing hydrocarbon group), except that the valence is limited to trivalence. Details regarding each of R4C, R4D and R4E are, for example, the same as the above-mentioned details regarding R2. Details regarding Rf2C, Rf2D and Rf2E are, for example, the same as the above-mentioned details regarding Rf1.

The compound shown in the chemical formula (8) is a compound in which n3=2 in the chemical formula (3). That is, in the compound illustrated herein, two branch portions (Rf3A-S(=O)$_2$—R6A-C(=O)—N<C(=O)—R7A-S(=O)$_2$—Rf4A and Rf3B—S(=O)$_2$—R6B—C(=O)—N<C(=O)—R7B—S(=O)$_2$—Rf4B) are bound to a stem portion (R5A).

Details regarding R5A (a divalent hydrocarbon group, a divalent oxygen-containing hydrocarbon group, a divalent halogenated hydrocarbon group and a divalent halogenated oxygen-containing hydrocarbon group) are, for example, the same as the above-mentioned details regarding R1 (an n-valent hydrocarbon group, an n-valent oxygen-containing hydrocarbon group, an n-valent halogenated hydrocarbon group and an n-valent halogenated oxygen-containing hydrocarbon group), except that the valence is limited to divalence. Details regarding each of R6A, R6B, R7A and R7B are, for example, the same as the above-mentioned details regarding R2. Details regarding Rf3A, Rf3B, Rf4A and Rf4B are, for example, the same as the above-mentioned details regarding Rf1.

The compound shown in the chemical formula (9) is a compound in which n3=3 in the chemical formula (3). That is, in the compound illustrated herein, three portions (Rf3C—S(=O)$_2$—R6C—C(=O)—N<C(=O)—R7C—S(=O)$_2$—Rf4C, Rf3D-S(=O)$_2$—R6D-C(=O)—N<C(=O)—R7D-S(=O)$_2$—Rf4D and Rf3E-S(=O)$_2$—R6E-C(=O)—N<C(=O)—R7E-S(=O)$_2$—Rf4E) are bound to a stem portion (R5B).

Details regarding R5B (a trivalent hydrocarbon group, a trivalent oxygen-containing hydrocarbon group, a trivalent halogenated hydrocarbon group and a trivalent halogenated oxygen-containing hydrocarbon group) are, for example, the same as the above-mentioned details regarding R1 (an n-valent hydrocarbon group, an n-valent oxygen-containing hydrocarbon group, an n-valent halogenated hydrocarbon group and an n-valent halogenated oxygen-containing hydrocarbon group), except that the valence is limited to trivalence. Details regarding each of R6C, R6D, R6E, R7C, R7D and R7E are, for example, the same as the above-mentioned details regarding R2. Details regarding Rf3C, Rf3D, Rf3E, Rf4C, Rf4D and Rf4E are, for example, the same as the above-mentioned details regarding Rf1.

Specific examples of the sulfonyl compound are as follows: However, specific examples of the sulfonyl compound are not limited to compounds illustrated below, but may be other compounds.

A specific example of the first sulfonyl compound is compounds that are represented by each of the following chemical formula (1-1) to chemical formula (1-12).

[Chemical formula (1-1) to (1-8)]

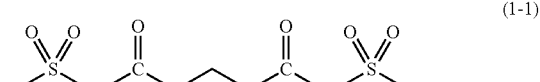

(1-1)

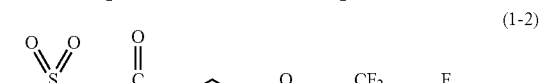

(1-2)

(1-3)

-continued

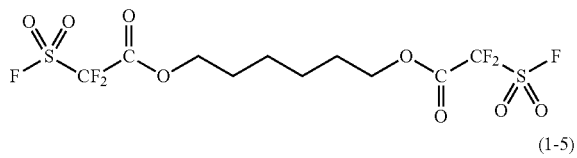
(1-4)

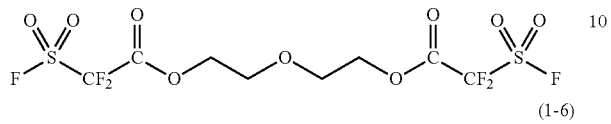
(1-5)

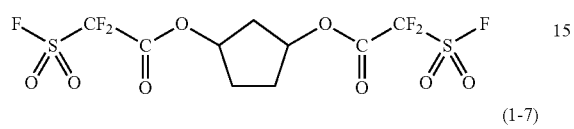
(1-6)

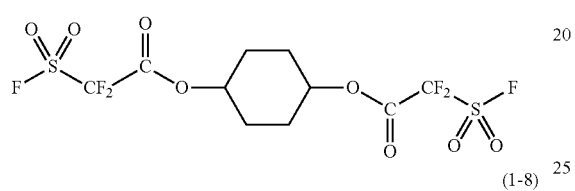
(1-7)

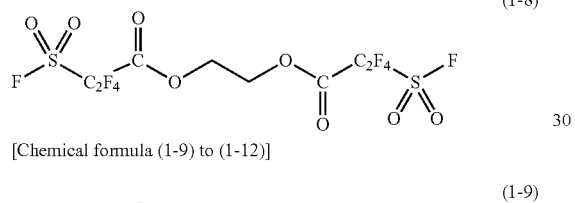
(1-8)

[Chemical formula (1-9) to (1-12)]

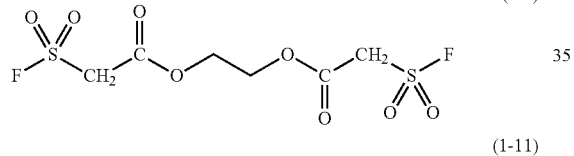
(1-9)

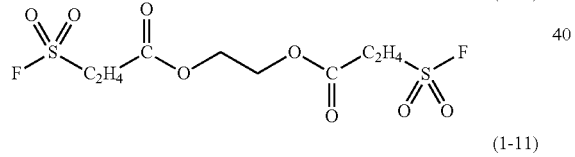
(1-11)

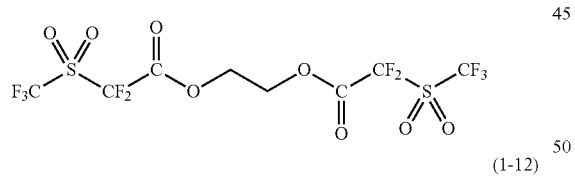
(1-11)

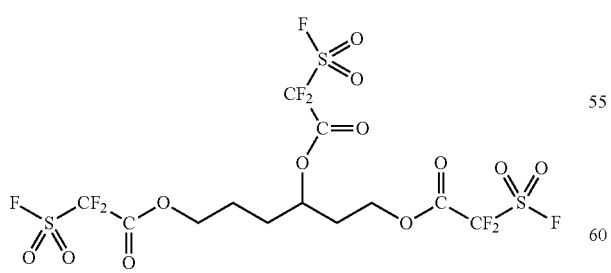
(1-12)

Compounds that are shown in each of the chemical formula (1-1) to the chemical formula (1-11) are compounds corresponding to the formula (4). That is, since n1=2, they are compounds in which the number of branch portions is 2.

The compound shown in the chemical formula (1-12) is a compound corresponding to the chemical formula (5). That is, since n1=3, it is a compound in which the number of branch portions is 3.

A specific example of the second sulfonyl compound is compounds that are represented by each of the following chemical formula (2-1) to chemical formula (2-23).

[Chemical formula (2-1) to (2-14)]

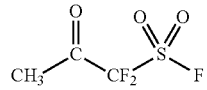
(2-1)

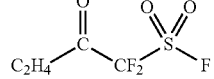
(2-2)

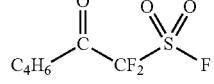
(2-3)

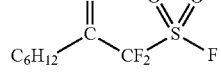
(2-4)

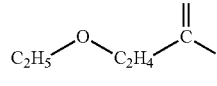
(2-5)

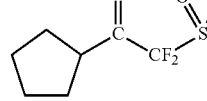
(2-6)

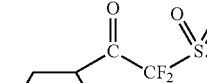
(2-7)

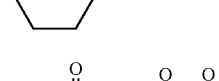
(2-8)

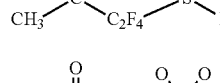
(2-9)

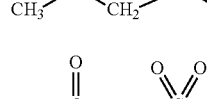
(2-10)

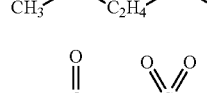
(2-11)

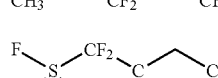
(2-12)

(2-13)
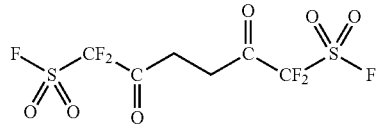

(2-14)
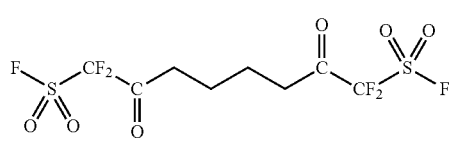

[Chemical formula (2-15) to (2-23)]

(2-15)
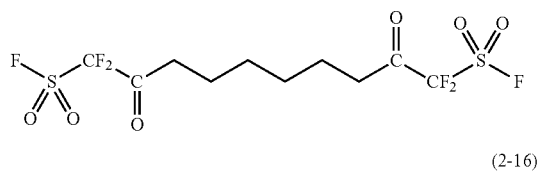

(2-16)
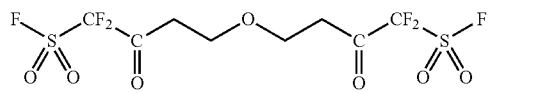

(2-17)
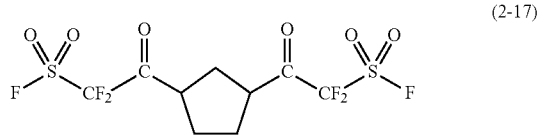

(2-18)
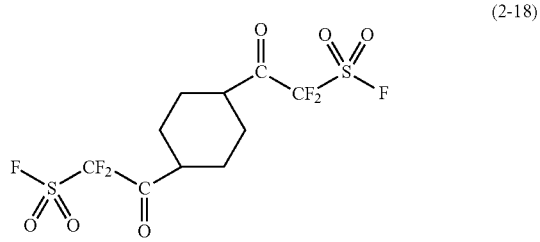

(2-19)
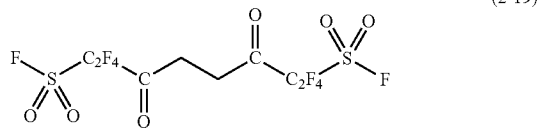

(2-20)
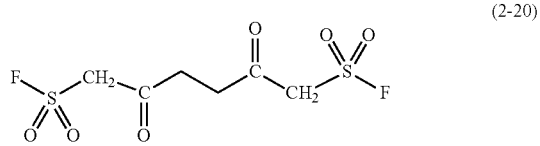

(2-21)
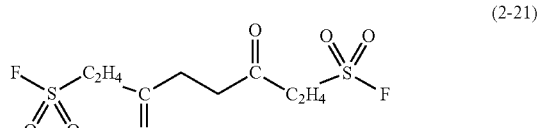

(2-22)
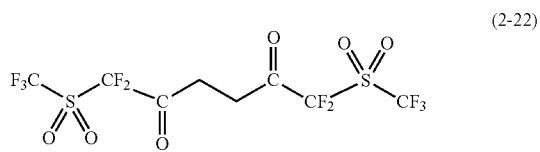

(2-23)
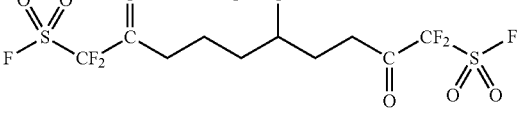

Compounds that are shown in each of the chemical formula (2-1) to the chemical formula (2-11) are compounds in which the number of a branch portion is 1 due to n2=1.

Compounds that are shown in each of the chemical formula (2-12) to the chemical formula (2-22) are compounds corresponding to the formula (6). That is, since n2=2, they are compounds in which the number of branch portions is 2.

The compound shown in the chemical formula (2-23) is a compound corresponding to the chemical formula (7). That is, since n2=3, it is a compound in which the number of branch portions is 3.

A specific example of the third sulfonyl compound is compounds that are represented by each of the following chemical formula (3-1) to chemical formula (3-23).

[Chemical formula (3-1) to (3-8)]

(3-1)
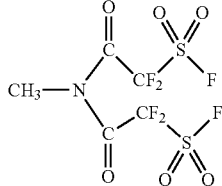

(3-2)
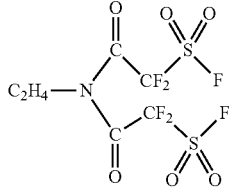

(3-3)
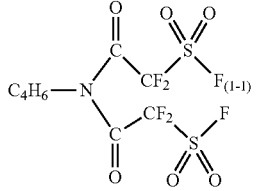

(3-4)
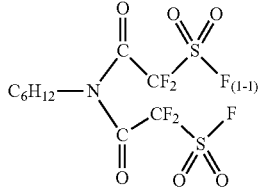

(3-5)
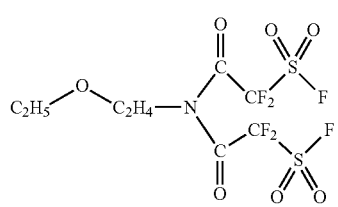
(3-6)
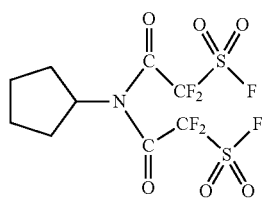
(3-7)
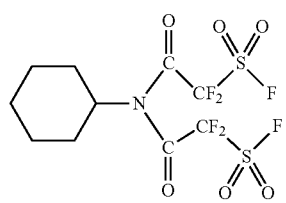
(3-8)
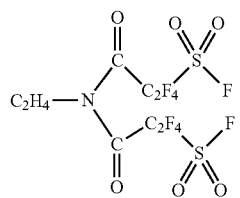
[Chemical formula (3-9) to (3-14)]
(3-9)
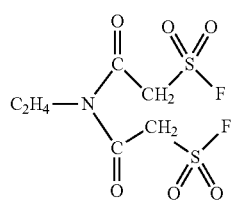
(3-10)
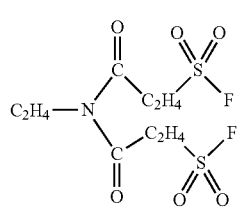
(3-11)
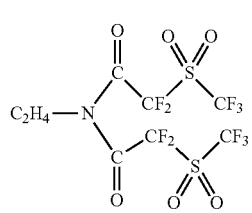
(3-12)
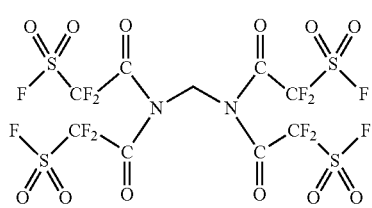
(3-13)
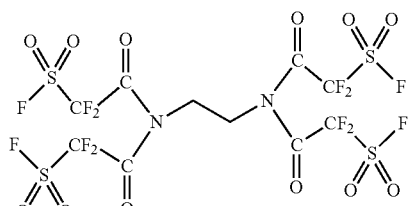
(3-14)
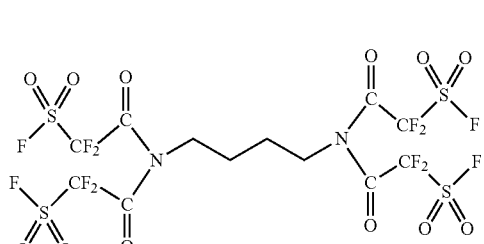
[Chemical formula (3-15) to (3-19)]
(3-15)
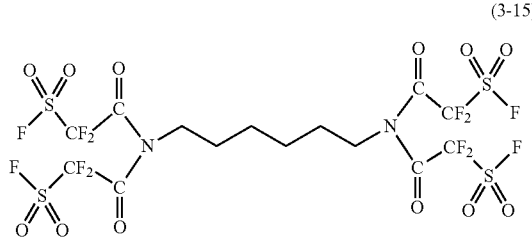
(3-16)
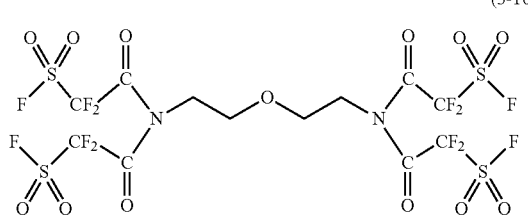
(3-17)
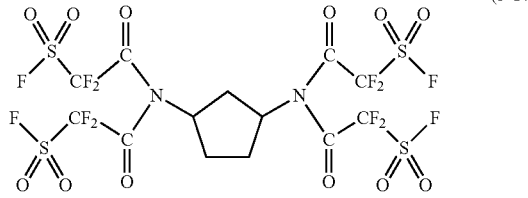
(3-18)
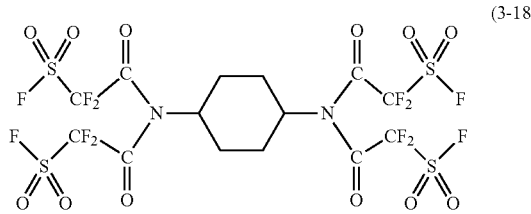

(3-19)
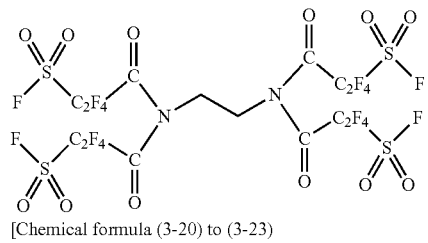

[Chemical formula (3-20) to (3-23)]

(3-20)
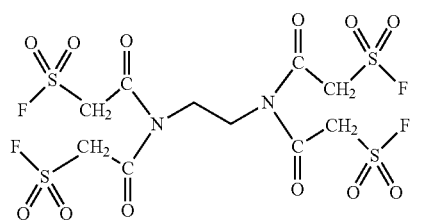

(3-21)
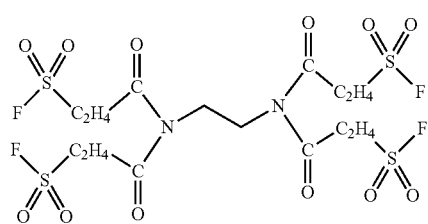

(3-22)
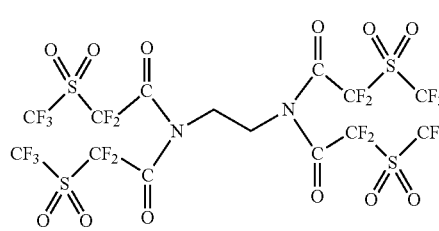

(3-23)
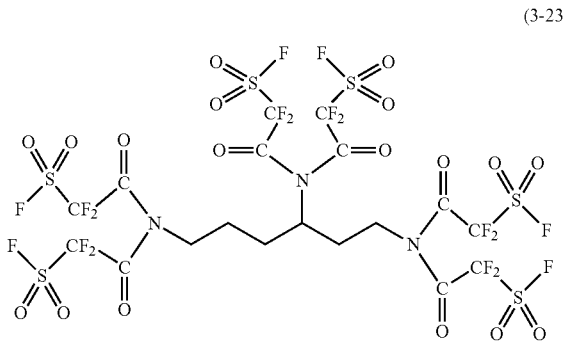

Compounds that are shown in each of the chemical formula (3-1) to the chemical formula (3-11) are compounds in which the number of a branch portion is 1 due to n3=1.

Compounds that are shown in each of the chemical formula (3-12) to the chemical formula (3-22) are compounds corresponding to the chemical formula (8). That is, since n3=2, they are compounds in which the number of branch portions is 2.

The compound shown in the chemical formula (3-23) is a compound corresponding to the chemical formula (9). That is, since n3=3, it is a compound in which the number of branch portions is 3.

In addition, the electrolytic solution may contain any one or two or more kinds of another material, in addition to the above-mentioned sulfonyl compound.

Another material is any one or two or more kinds of solvents such as a non-aqueous solvent (organic solvent). The electrolytic solution containing the non-aqueous solvent is a so-called non-aqueous electrolytic solution.

The solvent is, for example, cyclic carbonic acid ester, chainlike carbonic acid ester, lactone, chainlike carboxylic acid ester and nitrile (mononitrile). This is because the excellent battery capacity, cycle property and preservation property are obtained.

Specific examples of the cyclic carbonic acid ester are ethylene carbonate, propylene carbonate and butylene carbonate. Specific examples of the chainlike carbonic acid ester are dimethyl carbonate, diethyl carbonate, ethyl methyl carbonate and methyl propyl carbonate. Specific examples of the lactone are γ-butyrolactone and γ-valerolactone. Specific examples of the chainlike carboxylic acid ester are methyl acetate, ethyl acetate, methyl propionate, ethyl propionate, propyl propionate, methyl butyrate, methyl isobutyrate, methyl trimethylacetate and ethyl trimethylacetate. Specific examples of the nitrile are acetonitrile, methoxyacetonitrile and 3-methoxypropionitrile.

Besides this, the solvent may be, for example, 1,2-dimethoxyethane, tetrahydrofuran, 2-methyltetrahydrofuran, tetrahydropyran, 1,3-dioxolane, 4-methyl-1,3-dioxolane, 1,3-dioxane, 1,4-dioxane, N,N-dimethylformamide, N-methylpyrrolidinone, N-methyloxazolidinone, N,N'-dimethylimidazolidinone, nitromethane, nitroethane, sulfolane, trimethyl phosphate and dimethyl sulfoxide. This is because the same advantage is obtained.

Inter alia, it is preferable that the solvent contains any one or two or more kinds of ethylene carbonate, propylene carbonate, dimethyl carbonate, diethyl carbonate and ethyl methyl carbonate. This is because the high battery capacity, the excellent cycle property and the excellent preservation property are obtained. In this case, a combination of a high viscosity (high dielectric constant) solvent (for example, relative permittivity ε≥30) such as ethylene carbonate and propylene carbonate, and a low viscosity solvent (for example, viscosity ≤1 mPa·s) such as dimethyl carbonate, ethyl methyl carbonate and diethyl carbonate is more preferable. This is because the dissociability of an electrolyte salt and the ion mobility are improved.

Furthermore, the solvent may contain any one or two or more kinds of unsaturated cyclic carbonic acid ester, halogenated carbonic acid ester, sulfonic acid ester, an acid anhydride, a dinitrile compound and a diisocyanate compound. This is because the chemical stability of the electrolytic solution is more improved.

The unsaturated cyclic carbonic acid ester is cyclic carbonic acid ester comprising one or two or more intercarbon unsaturated bonds (intercarbon double bond), and is, for example, compounds that are represented by each of the following formula (10) to formula (12). The content of the unsaturated cyclic carbonic acid ester in the solvent is not particularly limited, but is, for example, 0.01% by weight to 10% by weight.

[Chemical formula 21]

(10)
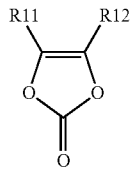

-continued

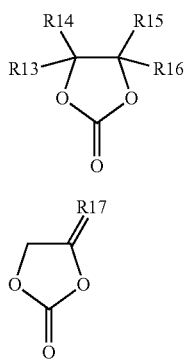
(11)

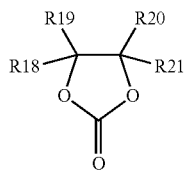
[Chemical formula 13 and 14]
(13)

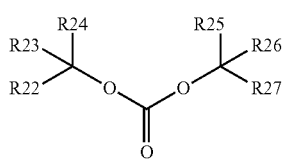
(14)

(12)

(Each of R11 and R12 is any of a hydrogen group and an alkyl group. Each of R13 to R16 is any of a hydrogen group, an alkyl group, a vinyl group and an allyl group, and at least one of R13 to R16 is any of a vinyl group and an allyl group. R17 is a group represented by >CR171R172, and each of R171 and R172 is any of a hydrogen group and an alkyl group.)

The compound shown in the chemical formula (10) is a vinylene carbonate type compound. R11 and R12 may be groups of the same kind as each other, or may be groups of different kinds from each other. Details regarding the alkyl group are as described above. Specific examples of the vinylene carbonate type compound are vinylene carbonate (1,3-dioxol-2-one), methyl vinylene carbonate (4-methyl-1,3-dioxol-2-one), ethyl vinylene carbonate (4-ethyl-1,3-dioxol-2-one), 4,5-dimethyl-1,3-dioxol-2-one, 4,5-diethyl-1,3-dioxol-2-one, 4-fluoro-1,3-dioxol-2-one and 4-trifluoromethyl-1,3-dioxol-2-one.

The compound shown in the chemical formula (11) is a vinyl ethylene carbonate type compound. R13 to R16 may be groups of the same kind as each other, or may be groups of different kinds from each other. Of course, a part of R13 to R16 may be groups of the same kind as each other. Specific examples of the vinyl ethylene carbonate type compound are vinyl ethylene carbonate (4-vinyl-1,3-dioxolan-2-one), 4-methyl-4-vinyl-1,3-dioxolan-2-one, 4-ethyl-4-vinyl-1,3-dioxolan-2-one, 4-n-propyl-4-vinyl-1,3-dioxolan-2-one, 5-methyl-4-vinyl-1,3-dioxolan-2-one, 4,4-divinyl-1,3-dioxolan-2-one and 4,5-divinyl-1,3-dioxolan-2-one.

The compound shown in the chemical formula (12) is a methylene ethylene carbonate type compound. R171 and R172 may be groups of the same kind as each other, or may be groups of different kinds from each other. Specific examples of the methylene ethylene carbonate type compound are methylene ethylene carbonate (4-methylene-1,3-dioxolan-2-one), 4,4-dimethyl-5-methylene-1,3-dioxolan-2-one and 4,4-diethyl-5-methylene-1,3-dioxolan-2-one.

Besides this, the unsaturated cyclic carbonic acid ester may be carbonic acid catechol (catechol carbonate) having a benzene ring.

The halogenated carbonic acid ester is cyclic or chainlike carbonic acid ester comprising one or two or more halogens as a constituent element, and is, for example, compounds that are represented by each of the following chemical formula (13) and chemical formula (14). The content of the halogenated carbonic acid ester in the solvent is not particularly limited, but is, for example, 0.01% by weight to 10% by weight.

(R18 to R21 are any of a hydrogen group, a halogen group, an alkyl group and a halogenated alkyl group, and at least one of R18 to R21 is any of a halogen group and a halogenated alkyl group. R22 to R27 are any of a hydrogen group, a halogen group, an alkyl group and a halogenated alkyl group, and at least one of R22 to R27 is any of a halogen group and a halogenated alkyl group.)

The compound shown in the chemical formula (5) is cyclic halogenated carbonic acid ester. R18 to R21 may be groups of the same kind as each other, or may be groups of different kinds from each other. Of course, a part of R18 to R21 may be groups of the same kind as each other.

A kind of the halogen group is not particularly limited, but is, inter alia, preferably any one or two or more kinds of a fluorine group, a chlorine group, a bromine group and an iodine group, more preferably a fluorine group. Furthermore, the number of the halogen group may be 1, or may be 2 or more.

Details regarding the alkyl group are as described above. The halogenated alkyl group is a group in which one or two or more hydrogen groups of the alkyl group are substituted (halogenated) with a halogen group. Details regarding the halogen group are as described above.

Specific examples of the cyclic halogenated carbonic acid ester are compounds that are represented by each of the following chemical formula (13-1) to chemical formula (13-21), and those compounds also include geometrical isomers. Inter alia, 4-fluoro-1,3-dioxolan-2-one shown in the formula (13-1) and 4,5-difluoro-1,3-dioxolan-2-one shown in the formula (13-3) are preferable. In addition, as 4,5-difluoro-1,3-dioxolan-2-one, a trans isomer is more preferable than a cis isomer. This is because it is easily available, and at the same time, the high effect is obtained.

[Chemical formula (13-1) to (13-21)]

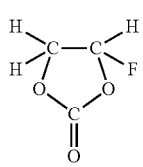
(13-1)

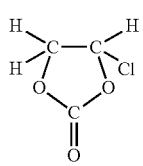
(13-2)

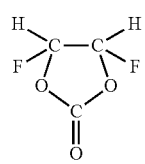 (13-3)
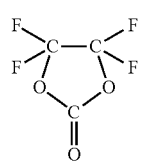 (13-4)
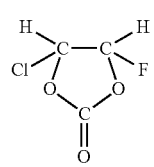 (13-5)
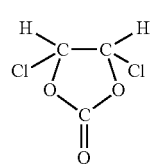 (13-6)
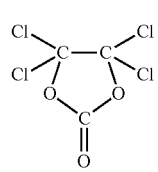 (13-7)
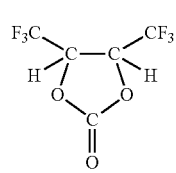 (13-8)
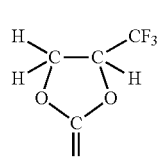 (13-9)
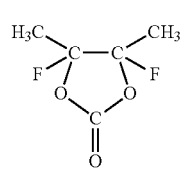 (13-10)
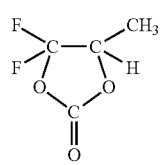 (13-11)
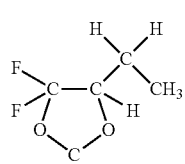 (13-12)
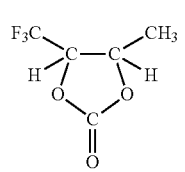 (13-13)
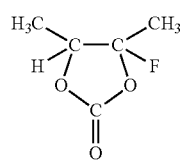 (13-14)
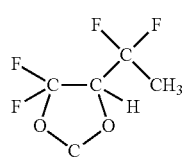 (13-15)
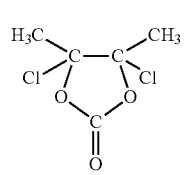 (13-16)
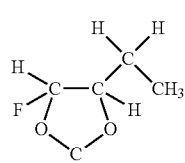 (13-17)
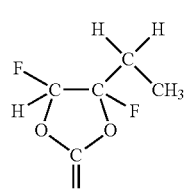 (13-18)
(13-19)

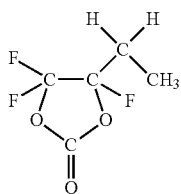
(13-20)

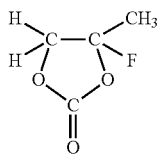
(13-21)

The compound shown in the chemical formula (14) is chainlike halogenated carbonic acid ester. R22 to R27 may be groups of the same kind as each other, or may be groups of different kinds from each other. Of course, a part of R22 to R27 may be groups of the same kind as each other.

Specific examples of the chainlike halogenated carbonic acid ester are fluoromethyl methyl carbonate, bis(fluoromethyl) carbonate and difluoromethyl methyl carbonate.

The sulfonic acid ester includes, for example monosulfonic acid ester and disulfonic acid ester. The content of the sulfonic acid ester in the solvent is not particularly limited, but is, for example, 0.01% by weight to 10% by weight.

The monosulfonic acid ester may be cyclic monosulfonic acid ester, or may be chainlike monosulfonic acid ester. A specific example of the cyclic monosulfonic acid ester is sultone such as 1,3-propanesultone and 1,3-propenesultone. A specific example of the chainlike monosulfonic acid ester is a compound in which cyclic monosulfonic acid ester is cut in the middle thereof.

The disulfonic acid ester may be cyclic disulfonic acid ester, or may be chainlike disulfonic acid ester. Specific examples of the cyclic disulfonic acid ester are compounds that are represented by each of the following chemical formula (15-1) to chemical formula (15-3). A specific example of the chainlike disulfonic acid ester is a compound in which cyclic disulfonic acid ester is cut in the middle thereof.

[Chemical formula (15-1) to (15-3)]

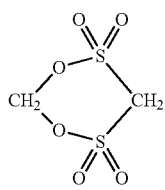
(15-1)

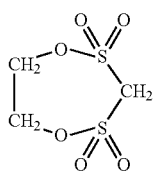
(15-2)

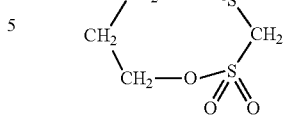
(15-3)

The acid anhydride is, for example, carboxylic anhydride, disulfonic anhydride and carbonic sulfonic anhydride. The content of the acid anhydride in the solvent is not particularly limited, but is, for example, 0.01% by weight to 10% by weight.

Specific examples of the carboxylic anhydride are succinic anhydride, glutaric anhydride and maleic anhydride. A specific example of the disulfonic anhydride is ethanedisulfonic anhydride and propanedisulfonic anhydride. Specific examples of the carbonic sulfonic anhydride are sulfobenzoic anhydride, sulfopropionic anhydride and sulfobutyric anhydride.

The dinitrile compound is, for example, any one or two or more kinds of compounds represented by the following formula (16). The content of the dinitrile compound in the solvent is not particularly limited, but is, for example, 0.1% by weight to 10% by weight, preferably 0.5% by weight to 2% by weight.

$$NC\text{—}R28\text{—}CN \quad (16)$$

(R28 is any of a divalent hydrocarbon group, a divalent halogenated hydrocarbon group, a divalent oxygen-containing group, a divalent nitrogen-containing group, a divalent sulfur-containing group, a divalent phosphorus-containing group and a divalent group in which two or more kinds of them are bound.)

The divalent hydrocarbon group is, for example, an alkylene group, an alkenylene group, an alkynylene group, a cycloalkylene group, an arylene group and a divalent group in which two or more kinds of them are bound. Specific examples of the divalent hydrocarbon group are a methylene group, a vinylene group, an ethynylene group, a cyclohexylene group and a phenylene group.

The divalent halogenated hydrocarbon group is a group in which one or two or more hydrogen groups of the above-mentioned divalent hydrocarbon group are substituted with a halogen group. A specific example of the monovalent halogenated hydrocarbon group is a perfluoromethylene group.

The divalent oxygen-containing group is a divalent group comprising oxygen as a constituent element. Specific examples of the divalent oxygen-containing group are an ether group (—O—), an ester group (—C(═O)O—), a carbonyl group (—C(═O)—) and an epoxy group (—COC—). Besides this, the divalent oxygen-containing group may be, for example, a divalent group (divalent oxygen-containing connected group) in which any one or two or more kinds of the above-mentioned specific examples of the divalent oxygen-containing group and any one or two or more kinds of the above-mentioned divalent hydrocarbon group and divalent halogenated hydrocarbon group are bound. Details regarding each of the divalent hydrocarbon group and the divalent halogenated hydrocarbon group are as described above. Specifically, the divalent hydrocarbon group and the divalent halogenated hydrocarbon group are, for example, a methylene group, a vinylene group, an ethynylene group, a cycloalkylene group, a phenylene group and a perfluoromethylene group. A specific example of the divalent oxygen-containing connected group is an alkyl ether group (—R201-O—R202-: Each of R201 and R202 is a divalent hydrocarbon group.).

The divalent nitrogen-containing group is a divalent group comprising nitrogen as a constituent element. Specific examples of the divalent nitrogen-containing group are an amide group (—NHCO—), a carbamate group (—NHCOO—), an amine group (—NH$_2$—), an azo group (—N=N—), a diazo group (—C=N$_2$—) and a diimide group (—N=C=N—). Besides this, the divalent nitrogen-containing group may be, for example, a divalent group (divalent nitrogen-containing connected group) in which any one or two or more kinds of the above-mentioned specific examples of the divalent nitrogen-containing group and any one or two or more kinds of the above-mentioned divalent hydrocarbon group and divalent halogenated hydrocarbon group are bound. Details regarding each of the divalent hydrocarbon group and the divalent halogenated hydrocarbon group are as described above. Specifically, the divalent hydrocarbon group and the divalent halogenated hydrocarbon group are, for example, a methylene group, a vinylene group, an ethynylene group, a cycloalkylene group, a phenylene group and a perfluoromethylene group. A specific example of the divalent nitrogen-containing connected group is an alkylamine group (—R203-NH$_2$—R204-: Each of R203 and R204 is a divalent hydrocarbon group.).

The divalent sulfur-containing group is a divalent group comprising sulfur as a constituent element. Specific examples of the divalent sulfur-containing group are a sulfonyl group (—SO$_2$—), a sulfide group (—S—) and a disulfide group (—S—S—). Besides this, the divalent sulfur-containing group may be, for example, a divalent group (divalent sulfur-containing connected group) in which any one or two or more kinds of the above-mentioned specific examples of the divalent sulfur-containing group and any one or two or more kinds of the above-mentioned divalent hydrocarbon group and divalent halogenated hydrocarbon group are bound. Details regarding each of the divalent hydrocarbon group and the divalent halogenated hydrocarbon group are as described above. Specifically, the divalent hydrocarbon group and the divalent halogenated hydrocarbon group are, for example, a methylene group, a vinylene group, an ethynylene group, a cycloalkylene group, a phenylene group and a perfluoromethylene group. A specific example of the divalent sulfur-containing connected group is an alkylsulfonyl group (—R205-SO$_2$—R206-: Each of R205 and R206 is a divalent hydrocarbon group.).

The divalent phosphorus-containing group is a group comprising phosphorus (P) as a constituent element. A specific example of the divalent phosphorus-containing group is a phosphatidyl group (—R207-PO$_4$—: R207 is a divalent hydrocarbon group.). Besides this, the divalent phosphorus-containing group may be, for example, a divalent group (divalent phosphorus-containing connected group) in which any one or two or more kinds of the above-mentioned specific examples of the divalent phosphorus-containing group and any one or two or more kinds of the above-mentioned divalent hydrocarbon group and divalent halogenated hydrocarbon group are bound. Details regarding each of the divalent hydrocarbon group and the divalent halogenated hydrocarbon group are as described above. Specifically, the divalent hydrocarbon group and the divalent halogenated hydrocarbon group are, for example, a methylene group, a vinylene group, an ethynylene group, a cycloalkylene group, a phenylene group and a perfluoromethylene group. A specific example of the divalent phosphorus-containing connected group is an alkylphosphatidyl group (—R207-PO$_4$—R208-: R208 is a divalent hydrocarbon group.).

Specific examples of the dinitrile compound are succinonitrile (NC—C$_2$H$_4$—CN), glutaronitrile (NC—C$_3$H$_6$—CN), adiponitrile (NC—C$_4$H$_8$—CN), sebaconitrile (NC—C$_8$H$_{16}$—CN) and phthalonitrile (NC—C$_6$H$_4$—CN).

The diisocyanate compound is, for example, a compound represented by OCN—C$_n$H$_{2n}$—NCO (wherein n is an integer of 1 or more.). The content of the diisocyanate compound in the solvent is not particularly limited, but is, for example, 0.1% by weight to 10% by weight. A specific example of the diisocyanate compound is OCN—C$_6$H$_{12}$—NCO.

The diisocyanate compound is, for example, a compound represented by OCN—C$_n$H$_{2n}$—NCO (wherein n is an integer of 1 or more.). The content of the diisocyanate compound in the solvent is not particularly limited, but is, for example, 0.1% by weight to 10% by weight. A specific example of the diisocyanate compound is OCN—C$_6$H$_{12}$—NCO.

Furthermore, another material is, for example, any one or two or more kinds of an electrolyte salt such as a lithium salt. Provided that the electrolyte salt may include, for example, a salt other than the lithium salt. The salt other than the lithium salt is a salt of a light metal other than lithium.

Specific examples of the lithium salt are lithium hexafluorophosphate (LiPF$_6$), lithium tetrafluoroborate (LiBF$_4$), lithium perchlorate (LiClO$_4$), lithium hexafluoroarsenate (LiAsF$_6$), lithium tetraphenylborate (LiB(C$_6$H$_5$)$_4$), lithium methanesulfonate (LiCH$_3$SO$_3$), lithium trifluoromethanesulfonate (LiCF$_3$SO$_3$), lithium tetrachloroaluminate (LiAlCl$_4$), dilithium hexafluorosilicate (Li$_2$SiF$_6$), lithium chloride (LiCl), and lithium bromide (LiBr).

Inter alia, any one or two or more kinds of lithium hexafluorophosphate, lithium tetrafluoroborate, lithium perchlorate and lithium hexafluoroarsenate are preferable, and lithium hexafluorophosphate is more preferable. This is because the internal resistance is reduced.

Besides this, the electrolyte salt may be any one or two or more kinds of compounds that are represented by each the following chemical formula (17) to chemical formula (19). R41 and R43 may be groups of the same kind as each other, or may be groups of different kinds from each other. R51 to R53 may be groups of the same kind as each other, or may be groups of different kinds from each other. Of course, a part of R51 to R53 may be groups of the same kind as each other. R61 and R62 may be groups of the same kind as each other, or may be groups of different kinds from each other.

[Chemical formula 17]

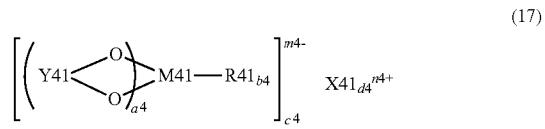

(17)

(X41 is any of a group 1 element and a group 2 element of the long-form periodic table, as well as aluminum (Al). M41 is any of a transition metal, as well as a group 13 element, a group 14 element and a group 15 element of the long-form periodic table. R41 is a halogen group. Y41 is any of —C(=O)—R42-C(=O)—, —C(=O)—CR43$_2$— and —C(=O)—C(=O)—. In the formula, R42 is any of an alkylene group, a halogenated alkylene group, an arylene group and a halogenated arylene group. R43 is any of an alkyl group, a halogenated alkyl group, an aryl group and a halogenated aryl group. And a4 is an integer of 1 to 4, b4 is an integer of 0, 2 or 4, and each of c4, d4, m4 and n4 is an integer of 1 to 3.)

[Chemical formula 18]

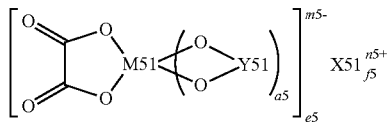

(18)

(X51 is any of a group 1 element and a group 2 element of the long-form periodic table. M51 is any of a transition metal, as well as a group 13 element, a group 14 element and a group 15 element of the long-form periodic table. Y51 is any of $-C(=O)-(CR51_2)_{b5}-C(=O)-$, $-R53_2C-(CR52_2)_{c5}-C(=O)-$, $-R53_2C-(CR52_2)_{c5}-CR53_2-$, $-R53_2C-(CR52_2)_{c5}-S(=O)_2-$, $-S(=O)_2-(CR52_2)_{d5}-S(=O)_2-$ and $-C(=O)-(CR52_2)_{d5}-S(=O)_2-$. Each of R51 and R53 is any of a hydrogen group, an alkyl group, a halogen group and a halogenated alkyl group. In the formula, at least one of R51s is any of a halogen group and a halogenated alkyl group, at least one of R53s is any of a halogen group and a halogenated alkyl group. R52 is any of a hydrogen group, an alkyl group, a halogen group and a halogenated alkyl group. Each of a5, e5 and n5 is an integer of 1 or 2, each of b5 and d5 is an integer of 1 to 4, c5 is an integer of 0 to 4, and each of f5 and m5 is an integer of 1 to 3.)

[Chemical formula 19]

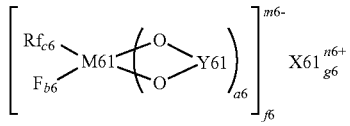

(19)

(X61 is any of a group 1 element and a group 2 element of the long-form periodic table. M61 is any of a transition metal, as well as a group 13 element, a group 14 element and a group 15 element of the long-form periodic table. Rf is any of a fluorinated alkyl group and a fluorinated aryl group, and the carbon number of each of the fluorinated alkyl group and the fluorinated aryl group is 1 to 10. Y61 is any of $-C(=O)-(CR61_2)_{d6}-C(=O)-$, $-R62_2C-(CR61_2)_{d6}-C(=O)-$, $-R62_2C-(CR61_2)_{d6}-CR62_2-$, $-R62_2C-(CR61_2)_{d6}-S(=O)_2-$, $-S(=O)_2-(CR61_2)_{d6}-S(=O)_2-$ and $-C(=O)-(CR61_2)_{e6}-S(=O)_2-$. In the formula, R61 is any of a hydrogen group, an alkyl group, a halogen group and a halogenated alkyl group. R62 is any of a hydrogen group, an alkyl group, a halogen group and a halogenated alkyl group, and at least one of R62s is any of a halogen group and a halogenated alkyl group. Each of a6, f6 and n6 is an integer of 1 or 2, each of b6, c6 and e6 is an integer of 1 to 4, d6 is an integer of 0 to 4, and each of g6 and m6 is an integer of 1 to 3.)

In addition, the group 1 element is hydrogen (H), lithium (Li), sodium (Na), potassium (K), rubidium (Rb), cesium (Cs) and francium (Fr). The group 2 element is beryllium (Be), magnesium (Mg), calcium (Ca), strontium (Sr), barium (Ba) and radium (Ra). The group 13 element is boron (B), aluminum (Al), gallium (Ga), indium (In) and thallium (Tl). The group 14 element is carbon (C), silicon (Si), germanium (Ge), tin (Sn) and lead (Pb). The group 15 element is nitrogen (N), phosphorus (P), arsenic (As), antimony (Sb) and bismuth (Bi).

Specific examples of the compound shown in the formula (17) are compounds that are represented by each of the following chemical formula (17-1) to chemical formula (17-6). Specific examples of the compound shown in the formula (18) are compounds that are represented by each of the following chemical formula (18-1) to chemical formula (18-8). A specific example of the compound shown in the chemical formula (19) is a compound represented by the following chemical formula (19-1).

[Chemical formula (17-1) to (17-6)]

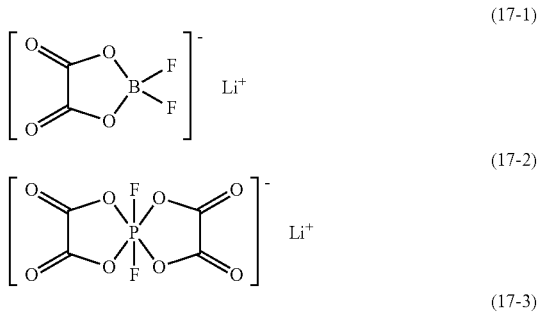

[Chemical formula (18-1) to (18-8)]

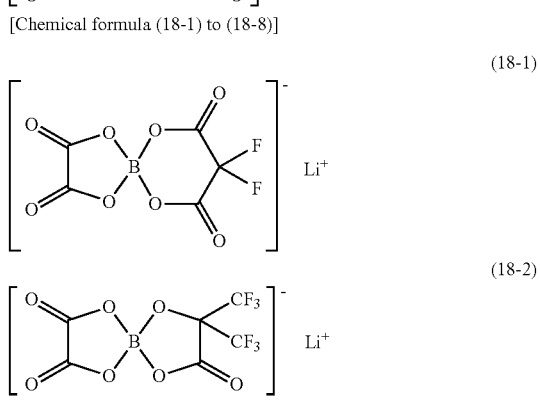

-continued

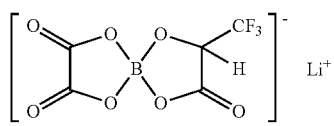
(18-3)

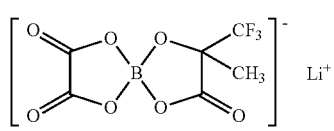
(18-4)

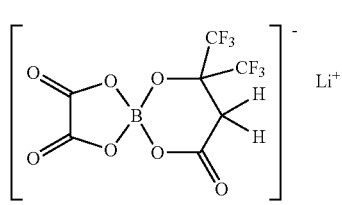
(18-5)

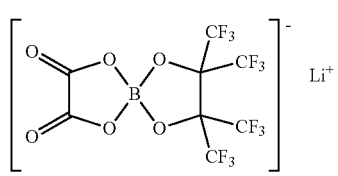
(18-6)

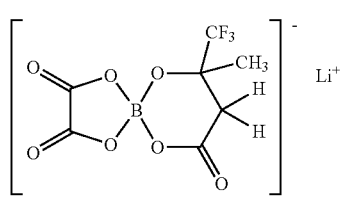
(18-7)

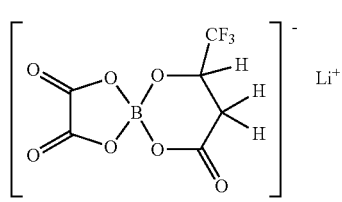
(18-8)

[Chemical formula (19-1)]

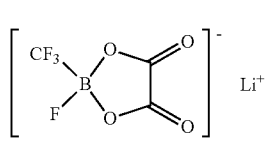
(19-1)

Furthermore, the electrolyte salt may be any one or two or more kinds of compounds that are represented by each of the following chemical formula (20) to chemical formula (22). The values of m and n may be the same as each other, or different from each other. And, p, q and r may be values that are the same as each other, or values that are different from each other. Of course, a part of p, q and r may be values that are the same as each other.

$$LiN(C_mF_{2m+1}SO_2)(C_nF_{2n+1}SO_2) \tag{20}$$

(Each of m and n is an integer of 1 or more.)

[Chemical formula 21]

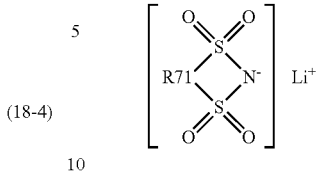
(21)

(R71 is a linear-chain or branched-chain perfluoroalkylene group having 2 to 4 carbon atoms.)

$$LiC(C_pF_{2p+1}SO_2)(C_qF_{2q+1}SO_2)(C_rF_{2r+1}SO_2) \tag{22}$$

(Each of p, q and r is an integer of 1 or more.)

The compound shown in the chemical formula (20) is a chainlike imide compound.

Specific examples of the chainlike imide compound are lithium bis(fluorosulfonyl)imide (LiN(SO$_2$F)$_2$), lithium bis(trifluoromethanesulfonyl)imide (LiN(CF$_3$SO$_2$)$_2$), lithium bis(pentafluoroethanesulfonyl)imide (LiN(C$_2$F$_5$SO$_2$)$_2$), lithium (trifluoromethanesulfonyl)(pentafluoroethanesulfonyl)imide (LiN(CF$_3$SO$_2$)(C$_2$F$_5$SO$_2$)), lithium (trifluoromethanesulfonyl)(heptafluoropropanesulfonyl)imide (LiN(CF$_3$SO$_2$)(C$_3$F$_7$SO$_2$)) and lithium (trifluoromethanesulfonyl)(nonafluorobutanesulfonyl)imide (LiN(CF$_3$SO$_2$)(C$_4$F$_9$SO$_2$)).

The compound shown in the chemical formula (21) is a cyclic imide compound. Specific examples of the cyclic imide compound are compounds that are represented by each of the following chemical formula (21-1) to chemical formula (21-4).

[Chemical formula (21-1) to (21-4)]

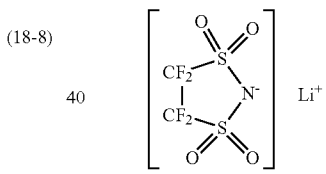
(21-1)

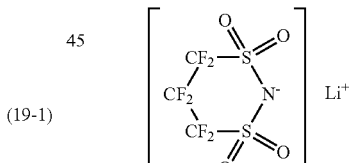
(21-2)

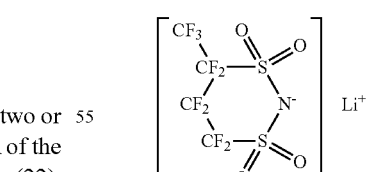
(21-3)

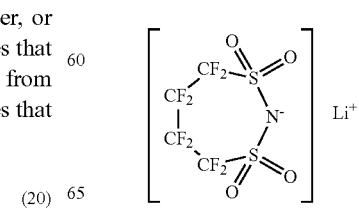
(21-4)

The compound shown in the chemical formula (22) is a chainlike methide compound. A specific example of the chainlike methide compound is lithium tris(trifluoromethanesulfonyl)methide (LiC(CF$_3$SO$_2$)$_3$).

The content of the electrolyte salt is not particularly limited, but inter alia, it is preferable that the content is 0.3 mol/kg to 3.0 mol/kg based on the solvent. This is because the high ion conductivity is obtained.

Furthermore, another material may be any one or two or more kinds of a material other than the above-mentioned materials. The material other than the above-mentioned materials is, for example, a phosphorus and fluorine-containing salt such as lithium difluorophosphate (LiPF$_2$O$_2$) and lithium fluorophosphate (Li$_2$PFO$_3$). The content of the phosphorus and fluorine-containing salt in the electrolytic solution is not particularly limited.

When the electrolytic solution is produced, for example, after an electrolyte salt is added to a solvent, the electrolyte salt is dissolved or dispersed in the solvent by stirring the solvent. Subsequently, after a sulfonyl compound is added to the solvent in which the electrolyte salt has been dissolved or dispersed, the sulfonyl compound is dissolved or dispersed in the solvent by stirring the solvent. A kind of the sulfonyl compound may be only one kind, or two or more kinds. Thereby, an electrolytic solution containing the sulfonyl compound is obtained.

This electrolytic solution contains the above-mentioned sulfonyl compound. In this case, as compared with the case where the electrolytic solution does not contain the sulfonyl compound and the case where the electrolytic solution contains another compound, the chemical stability of the electrolytic solution is improved, as described above. Thereby, a decomposition reaction of the electrolytic solution is suppressed, and at the same time, generation of the gas due to the decomposition reaction of the electrolytic solution is suppressed. Accordingly, the battery property of a secondary battery using the electrolytic solution can be improved.

In addition, the above-mentioned "another compound" is a compound not corresponding to the sulfonyl compound, more specifically, is a compound that does not satisfy conditions shown in each of the chemical formula (1), the chemical formula (2) and the chemical formula (3). Another compound is, for example, a compound represented by the following chemical formula (23-1). The compound shown in the chemical formula (23-1) is, for example, a compound in which n1=1 in the chemical formula (1). That is, since n1=1, it is a compound in which the number of a branch portion (—C(=O)—R2-S(=O)$_2$—Rf1) is 1.

[Chemical formula (23-1)]

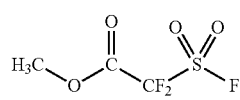

(23-1)

Particularly, regarding the first sulfonyl compound shown in the chemical formula (1), when the n1-valent hydrocarbon group is a group in which n1 hydrogen groups are eliminated from a hydrocarbon such as an alkane, each of the n1-valent oxygen-containing hydrocarbon group, the n1-valent halogenated hydrocarbon group and the n1-valent halogenated oxygen-containing hydrocarbon group is a group based on the above-mentioned n1-valent hydrocarbon group, and the halogen group is a fluorine group or the like, the chemical stability of the electrolytic solution is more improved. Accordingly, since a decomposition reaction of the electrolytic solution is more suppressed, the higher effect can be obtained.

Furthermore, regarding the second sulfonyl compound shown in the chemical formula (2), when the n2-valent hydrocarbon group is a group in which n2 hydrogen groups are eliminated from a hydrocarbon such as an alkane, and at the same time, each of the n2-valent oxygen-containing hydrocarbon group, the n2-valent halogenated hydrocarbon group and the n2-valent halogenated oxygen-containing hydrocarbon group is a group based on the above-mentioned n2-valent hydrocarbon group, and the halogen group is a fluorine group or the like, the chemical stability of the electrolytic solution is more improved. Accordingly, since a decomposition reaction of the electrolytic solution is more suppressed, the higher effect can be obtained.

Furthermore, regarding the third sulfonyl compound shown in the chemical formula (3), when the n3-valent hydrocarbon group is a group in which n3 hydrogen groups are eliminated from a hydrocarbon such as an alkane, and at the same time, each of the n3-valent oxygen-containing hydrocarbon group, the n3-valent halogenated hydrocarbon group and the n3-valent halogenated oxygen-containing hydrocarbon group is a group based on the above-mentioned n3-valent hydrocarbon group, and the halogen group is a fluorine group or the like, the chemical stability of the electrolytic solution is more improved. Accordingly, since a decomposition reaction of the electrolytic solution is more suppressed, the higher effect can be obtained.

Furthermore, when the divalent hydrocarbon group is an alkylene group, the divalent halogenated hydrocarbon group is a group based on the above-mentioned divalent hydrocarbon group, and the halogen group is a fluorine group or the like, since the chemical stability of the electrolytic solution is more improved, the higher effect can be obtained.

Furthermore, when the halogen group is a fluorine group or the like, and at the same time, the monovalent halogenated hydrocarbon group is a group based on a monovalent hydrocarbon group such as an alkyl group, since the chemical stability of the electrolytic solution is more improved, the higher effect can be obtained.

Furthermore, in the case where the n1-valent hydrocarbon group is a group in which n1 hydrogen groups are eliminated from an alkane, the n2-valent hydrocarbon group is a group in which n2 hydrogen groups are eliminated from an alkane, and the n3-valent hydrocarbon group is a group in which n3 hydrogen groups are eliminated from an alkane, when the carbon number of each of the n1-valent hydrocarbon group, the n2-valent hydrocarbon group and the n3-valent hydrocarbon group is 1 to 12, since the chemical stability of the electrolytic solution is more improved, the higher effect can be obtained.

Furthermore, when the carbon number of each of the divalent hydrocarbon group and the divalent halogenated hydrocarbon group is 1 to 4, since the chemical stability of the electrolytic solution is more improved, the higher effect can be obtained.

Furthermore, when the carbon number of the monovalent halogenated hydrocarbon is 1 to 4, or the monovalent halogenated hydrocarbon group is a perfluoroalkyl group, since the chemical stability of the electrolytic solution is more improved, the higher effect can be obtained.

Furthermore, when n1 is 4 or less, n2 is 4 or less, and n3 is 8 or less, or n2 is 2 or more, and n3 is 2 or more, since the chemical stability of the electrolytic solution is more improved, the higher effect can be obtained.

Furthermore, when the sulfonyl compound shown in the chemical formula (1) includes one or both of compounds that are shown in each of the chemical formula (4) and the chemical formula (5), the sulfonyl compound shown in the chemical formula (2) includes one or both of compounds that are shown in each of the chemical formula (6) and the chemical formula (7), and the sulfonyl compound shown in the chemical formula (3) includes one or both of compounds that are shown in each of the chemical formula (8) and the chemical formula (9), since the chemical stability of the electrolytic solution is more improved, the higher effect can be obtained.

Furthermore, when the electrolytic solution contains the dinitrile compound together with the sulfonyl compound, since the chemical stability of the electrolytic solution is more improved, the higher effect can be obtained.

Furthermore, when the content of the sulfonyl compound in the electrolytic solution is 0.01% by weight to 5% by weight, since the chemical stability of the electrolytic solution is more improved, the higher effect can be obtained.

Then, a secondary battery using the above-mentioned electrolytic solution will be illustrated.

Figure 2:
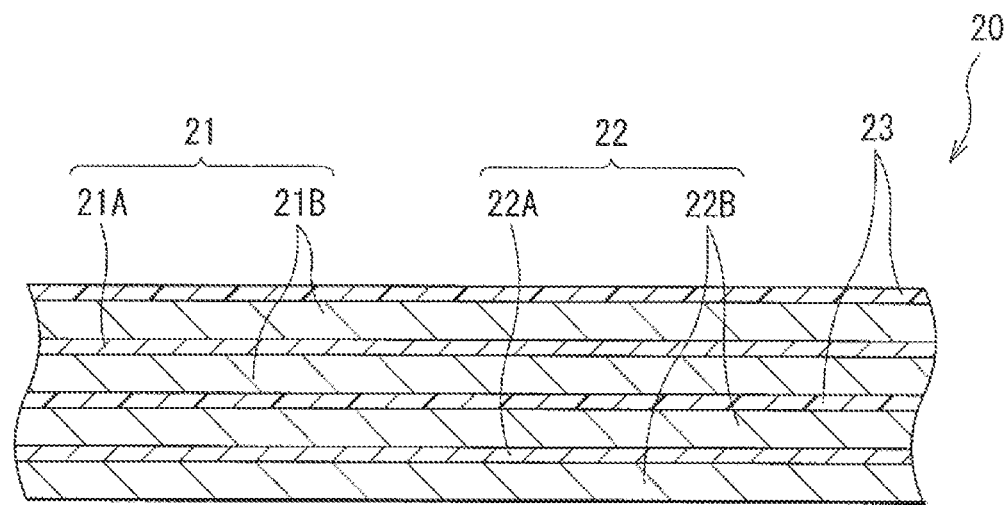
FIG. 2 is a cross-sectional view representing a feature of a part of a wound electrode body shown in FIG. 1 by enlargement.

FIG. 1 represents a cross-sectional configuration of a secondary battery, and FIG. 2 enlarges a cross-sectional configuration of a part of a wound electrode body 20 shown in FIG. 1.

A secondary battery illustrated herein is, for example, a lithium ion secondary battery in which the capacity of a negative electrode 22 is obtained by occlusion and release of lithium that is an electrode reactant.

This secondary battery has a so-called cylindrical type battery configuration, and for example, as shown in FIG. 1, one pair of insulating plates 12, 13, and a wound electrode body 20 that is a battery element are housed in the interior of a hollow columnar battery can 11. In the wound electrode body 20, for example, after a positive electrode 21 and a negative electrode 22 are laminated with a separator 23 interposed therebetween, the positive electrode 21, the negative electrode 22 and the separator 23 are wound. This wound electrode body 20 is impregnated with an electrolytic solution that is a liquid electrolyte.

The battery can 11 has, for example, a hollow structure in which one end is closed, and at the same time, the other end is opened, and contains one or two or more kinds of iron, aluminum and an alloy thereof. The surface of this battery can 11 may be plated with nickel. The one pair of insulating plates 12, 13 are arranged so as to hold the wound electrode body 20, and at the same time, extend vertical to the winding circumferential surface thereof.

At an open end of the battery can 11, a battery lid 14, a safety valve mechanism 15, and a heat-sensitive resistive element (PTC element) 16 are crimped with a gasket 17 interposed therebetween. Thereby, the battery can 11 is sealed. The battery lid 14 is formed of, for example, the same material as that of the battery can 11. Each of the safety valve mechanism 15 and the heat-sensitive resistive element 16 is disposed inside the battery lid 14, and the safety valve mechanism 15 is electrically connected to the battery lid 14 with the heat-sensitive resistive element 16 interposed therebetween. In this safety valve mechanism 15, when the internal pressure becomes a prescribed value or higher due to internal short or heating from the outside, a disk plate 15A is inverted. Thereby, electrical connection between the battery lid 14 and the wound electrode body 20 is cut. In order to prevent abnormal heat generation due to the large current, the resistance of the heat-sensitive resistive element 16 is increased in response to rise in the temperature. The gasket 17 is formed of, for example, an insulating material, and the surface of the gasket 17 may be coated with the asphalt or the like.

In a winding center of the wound electrode body 20, for example, a center pin 24 is inserted. In this regard, the center pin 24 need not be inserted in the winding center of the wound electrode body 20. A positive electrode lead 25 is attached to the positive electrode 21, and at the same time, a negative electrode lead 26 is attached to the negative electrode 22. The positive electrode lead 25 contains, for example, an electrically conductive material such as aluminum. This positive electrode lead 25 is attached to, for example, the safety valve mechanism 15, and at the same time, electrically connected to the battery lid 14. The negative electrode lead 26 contains, for example, an electrically conductive material such as nickel. This negative electrode lead 26 is attached to, for example, the battery can 11, and is electrically connected to the battery can 11.

The positive electrode 21 comprises, for example, a positive electrode current collector 21A, and a positive electrode active material layer 21B disposed on both sides of the positive electrode current collector 21A, as shown in FIG. 2. In this regard, the positive electrode active material layer 21B may be disposed on only one side of the positive electrode current collector 21A.

The positive electrode current collector 21A contains, for example, any one or two or more kinds of an electrically conductive material. A kind of the electrically conductive material is not particularly limited, but is, for example, a metal material such as aluminum, nickel and stainless steel. This positive electrode current collector 21A may be a monolayer, or may be a multilayer.

The positive active material layer 21B contains, as a positive electrode active material, any one or two or more kinds of a positive electrode material that can occlude and release lithium. Provided that the positive electrode active material layer 21B may contain any one or two or more kinds of another material such as a positive electrode binding agent and a positive electrode conducting agent, in addition to the positive electrode active material.

The positive electrode material is preferably a lithium-containing compound, and more specifically, is preferably any one or both of a lithium-containing complex oxide and a lithium-containing phosphate compound. This is because the high energy density is obtained.

The lithium-containing complex oxide is an oxide containing, as a constituent element, lithium and one or two or more other elements (elements other than lithium), and has, for example, a crystal structure of any of a layered rock salt type and a spinel type. The lithium-containing phosphate compound is a phosphate compound containing, as a constituent element, lithium and one or two or more other elements, and has, for example, a crystal structure such as an olivine type.

A kind of other elements is not particularly limited, as long as they are any one or two or more kinds of any elements. Inter alia, it is preferable that other elements are any one or two or more kinds of elements belonging to a group 2 to a group 15 of the long-form periodic table. More specifically, it is more preferable that other elements contain any one or two or more kinds of metal elements of nickel (Ni), cobalt (Co), manganese (Mn) and iron (Fe). This is because a high voltage is obtained.

The lithium-containing complex oxide having a layered rock salt type crystal structure is, for example, compounds that are represented by each of the following chemical formula (21) to chemical formula (23):

$$Li_aMn_{(1-b-c)}Ni_bM11_cO_{(2-d)}F_e \quad (21)$$

(M11 is at least one kind of cobalt (Co), magnesium (Mg), aluminum (Al), boron (B), titanium (Ti), vanadium (V), chromium (Cr), iron (Fe), copper (Cu), zinc (Zn), zirconium (Zr), molybdenum (Mo), tin (Sn), calcium (Ca), strontium (Sr) and tungsten (W). And a to e satisfy $0.8 \leq a \leq 1.2$, $0 < b < 0.5$, $0 \leq c \leq 0.5$, $(b+c) < 1$, $-0.1 \leq d \leq 0.2$ and $0 \leq e \leq 0.1$. Provided that the composition of lithium is different depending on the charged or discharged state, and a is a value in the completely discharged state.)

$$Li_aNi_{(1-b)}M12_bO_{(2-c)}F_d \quad (22)$$

(M12 is at least one kind of cobalt (Co), manganese (Mn), magnesium (Mg), aluminum (Al), boron (B), titanium (Ti), vanadium (V), chromium (Cr), iron (Fe), copper (Cu), zinc (Zn), molybdenum (Mo), tin (Sn), calcium (Ca), strontium (Sr) and tungsten (W). And a to d satisfy $0.8 \leq a \leq 1.2$, $0.005 \leq b < 0.5$, $-0.1 \leq c \leq 0.2$ and $0 \leq d \leq 0.1$. Provided that the composition of lithium is different depending on the charged or discharged state, and a is a value in the completely discharged state.)

$$Li_aCo_{(1-b)}M13_bO_{(2-c)}F_d \quad (23)$$

(M13 is at least one kind of nickel (Ni), manganese (Mn), magnesium (Mg), aluminum (Al), boron (B), titanium (Ti), vanadium (V), chromium (Cr), iron (Fe), copper (Cu), zinc (Zn), molybdenum (Mo), tin (Sn), calcium (Ca), strontium (Sr) and tungsten (W). And a to d satisfy $0.8 \leq a \leq 1.2$, $0 \leq b < 0.5$, $-0.1 \leq c \leq 0.2$ and $0 \leq d \leq 0.1$. Provided that the composition of lithium is different depending on the charged or discharged state, and a is a value in the completely discharged state.)

Specific examples of the lithium-containing complex oxide having a layered rock salt type crystal structure are $LiNiO_2$, $LiCoO_2$, $LiCo_{0.98}Al_{0.01}Mg_{0.01}O_2$, $LiNi_{0.5}Co_{0.2}Mn_{0.3}O_2$, $LiNi_{0.8}Co_{0.15}Al_{0.05}O_2$, $LiNi_{0.33}Co_{0.33}O_2$, $Li_{1.2}Mn_{0.52}Co_{0.175}Ni_{0.1}O_2$ and $Li_{1.15}(Mn_{0.65}Ni_{0.22}Co_{0.13})O_2$.

In addition, when the lithium-containing complex oxide having a layered rock salt type crystal structure contains, as a constituent element, nickel, cobalt, manganese and aluminum, the atomic ratio of the nickel is preferably 50 atom % or more. This is because the high energy density is obtained.

The lithium-containing complex oxide having a spinel type crystal structure is, for example, a compound represented by the following chemical formula (24):

$$Li_aMn_{(2-b)}M14_bO_cF_d \quad (24)$$

(M14 is at least one kind of cobalt (Co), nickel (Ni), magnesium (Mg), aluminum (Al), boron (B), titanium (Ti), vanadium (V), chromium (Cr), iron (Fe), copper (Cu), zinc (Zn), molybdenum (Mo), tin (Sn), calcium (Ca), strontium (Sr) and tungsten (W). And a to d satisfy $0.9 \leq a \leq 1.1$, $0 \leq b \leq 0.6$, $3.7 \leq c \leq 4.1$ and $0 \leq d \leq 0.1$. Provided that the composition of lithium is different depending on the charged or discharged state, and a is a value in the completely discharged state.)

A specific example of the lithium-containing complex oxide having a spinel type crystal structure is $LiMn_2O_4$.

The lithium-containing phosphate compound having an olivine type crystal structure is, for example, a compound represented by the following chemical formula (25):

$$Li_aM15PO_4 \quad (25)$$

(M15 is at least one kind of cobalt (Co), manganese (Mn), iron (Fe), nickel (Ni), magnesium (Mg), aluminum (Al), boron (B), titanium (Ti), vanadium (V), niobium (Nb), copper (Cu), zinc (Zn), molybdenum (Mo), calcium (Ca), strontium (Sr), tungsten (W) and zirconium (Zr). And a satisfies $0.9 \leq a \leq 1.1$. Provided that the composition of lithium is different depending on the charged or discharged state, and a is a value in the completely discharged state.)

Specific examples of the lithium-containing phosphate compound having an olivine type crystal structure are $LiFePO_4$, $LiMnPO_4$, $LiFe_{0.5}Mn_{0.5}PO_4$ and $LiFe_{0.3}Mn_{0.7}PO_4$.

In addition, the lithium-containing complex oxide may be a compound represented by the following chemical formula (26):

$$(Li_2MnO_3)_x(LiMnO_2)_{1-x} \quad (26)$$

(X satisfies $0 \leq x \leq 1$. Provided that the composition of lithium is different depending on the charged or discharged state, and a is a value in the completely discharged state.)

Besides this, the positive electrode material may be, for example, any one or two or more kinds of oxide, disulfide, chalcogenide and an electrically conductive polymer. The oxide is, for example, titanium oxide, vanadium oxide and manganese dioxide. The disulfide is, for example, titanium disulfide and molybdenum disulfide. The chalcogenide is, for example, niobium selenide. The electrically conductive polymer is, for example, sulfur, polyaniline and polythiophene. Provided that the positive electrode material may be another material other than the above-mentioned materials.

The positive electrode binding agent contains, for example, any one or two or more kinds of a synthetic rubber and a polymer compound. The synthetic rubber is, for example, a styrene-butadiene-based rubber, a fluorine-based rubber and ethylene-propylene-diene. The polymer compound is, for example, polyvinylidene fluoride and polyimide.

The positive electrode conducting agent contains, for example, any one or two or more kinds of a carbon material. This carbon material is, for example, graphite, carbon black, acetylene black and Ketjen black. Provided that the positive electrode conducting agent may be a metal material and an electrically conductive polymer, so long as it is a material having the electrical conductivity.

The negative electrode 22 comprises, for example, a negative electrode current collector 22A, and a negative electrode active material layer 22B provided on both sides of the negative electrode current collector 22A, as shown in FIG. 2. Provided that the negative electrode active material layer 22B may be provided on only one side of the negative electrode current collector 22A.

The negative electrode current collector 22A contains, for example, any one or two or more kinds of an electrically conductive material. A kind of the electrically conductive material is not particularly limited, but is, for example, a metal material such as copper, aluminum, nickel and stainless steel. This negative electrode current collector 22A may be a monolayer or a multilayer.

It is preferable that the surface of the negative electrode current collector 22A is roughened. This is because the close contact property of the negative electrode active material layer 22B to the negative electrode current collector 22A is improved due to so-called anchoring effect. In this case, it is enough that at least in a region opposite to the negative electrode active material layer 22B, the surface of the negative electrode current collector 22A is roughened. A method of roughening is, for example, a method of forming fine grains utilizing electrolytic treatment. In electrolytic treatment, since fine grains are formed on the surface of the negative electrode current collector 22A in an electrolytic bath by an electrolytic method, irregularities are provided on the surface of the negative electrode current collector 22A. A copper foil manufactured by an electrolytic method is generally called electrolytic copper foil.

The negative electrode active material layer 22B contains, as the negative electrode active material, any one or two or more kinds of a negative electrode material that can occlude and release lithium. Provided that the negative electrode active material layer 22B may contain any one or two or more kinds of other materials such as a negative electrode binding agent and a negative electrode conducting agent, in addition to the negative electrode active material.

In order to prevent a lithium metal from unintentionally precipitating on the negative electrode 22 during charging, it is preferable that the chargeable capacity of the negative electrode material is greater than the discharge capacity of the positive electrode 21. That is, it is preferable that the electrochemical equivalent of the negative electrode material that can occlude and release lithium is greater than the electrochemical equivalent of the positive electrode 21.

The negative electrode material is, for example, any one or two or more kinds of a carbon material. This is because since change in a crystal structure at occlusion and release of lithium is very small, the high energy density is stably obtained. Furthermore, this is because since the carbon material also functions as the negative electrode conducting agent, the electrical conductivity of the negative electrode active material layer 22B is improved.

The carbon material is, for example, easily graphitizable carbon, hardly graphitizable carbon and graphite. Provided that the spacing of the (002) plane in hardly graphitizable carbon is preferably 0.37 nm or more, and at the same time, the spacing of the (002) plane in graphite is preferably 0.34 nm or less. More specifically, the carbon material is, for example, pyrolytic carbon, coke, glassy carbon fiber, fired organic polymer compound, activated carbon and carbon black. This coke includes pitch coke, needle coke and petroleum coke. The fired organic polymer compound is a polymer compound such as a phenol resin and a furan resin, which has been fired (carbonized) at an appropriate temperature. Besides this, the carbon material may be low crystalline carbon that has been heat-treated at a temperature of about 1000° C. or lower, or may be amorphous carbon. In addition, a shape of the carbon material may be any of a fibrous shape, a spherical shape, a particulate shape and a scaly shape.

Furthermore, the negative electrode material is a material that contains, as a constituent element, any one or two or more kinds of metal elements and semimetal elements (metal-based material). This is because the high energy density is obtained.

The metal-based material may be any of a simple substance, an alloy and a compound, may be two or more kinds of them, or may be a material having one or two or more kinds of phases of them at least in a part thereof. Provided that the alloy also includes a material containing one or two or more kinds of metal elements and one or two or more kinds of semimetal elements, in addition to the material composed of two or more kinds of metal elements. Alternatively, the alloy may contain a nonmetal element. The structure of this metal-based material may be, for example, a solid solution, a eutectic (eutectic mixture), an intermetallic compound and a coexisting material of two or more kinds of them.

The above-mentioned metal element and semimetal element are, for example, any one or two or more kinds of a metal element and a semimetal element, which can form an alloy with lithium. Specifically, they are, for example, magnesium (Mg), boron (B), aluminum (Al), gallium (Ga), indium (In), silicon (Si), germanium (Ge), tin (Sn), lead (Pb), bismuth (Bi), cadmium (Cd), silver (Ag), zinc, hafnium (Hf), zirconium, yttrium (Y), palladium (Pd) and platinum (Pt).

Inter alia, one or both of silicon and tin are preferable. This is because the remarkably high energy density is obtained due to the excellent ability to occlude and release lithium.

The material containing, as a constituent element, one or both of silicon and tin may be any of a simple substance, an alloy and a compound of silicon, may be any of a simple substance, an alloy and a compound of tin, may be two or more kinds of them, or may be a material having one or two or more phases of them, at least in a part thereof. The simple substance illustrated herein means just a simple substance (that may contain a minor amount of impurities) in a general sense, and does not necessarily mean the purity of 100%.

The alloy of silicon contains, as a constituent element other than silicon, for example, any one or two or more kinds of tin, nickel, copper, iron, cobalt, manganese, indium, silver, titanium, germanium, bismuth, antimony and chromium. The compound of silicon contains, as a constituent element other than silicon, for example, any one or two or more kinds of carbon and oxygen. In addition, the compound of silicon may contain, as a constituent element other than silicon, for example, any one or two or more kinds of a series of elements illustrated regarding the alloy of silicon.

Specific examples of each of the alloy of silicon and the compound of silicon are, for example, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_5Si$, $FeSi_2$, $MnSi_2$, $NbSi_2$, $TaSi_2$, $VSi_2$, $WSi_2$, $ZnSi_2$, $SiC$, $Si_3N_4$, $Si_2N_2O$, $SiO_v$, ($0<v\leq2$), and $LiSiO$. In addition, v in $SiO_v$ may also be $0.2<v<1.4$.

The alloy of tin contains, as a constituent element other than tin, for example, any one or two or more kinds of silicon, nickel, copper, iron, cobalt, manganese, zinc, indium, silver, titanium, germanium, bismuth, antimony and chromium. The compound of tin contains, as a constituent element other than tin, for example, any one or two or more kinds of carbon and oxygen. In addition, the compound of tin may contain, as a constituent element other than tin, for example, one or two or more kinds of a series of elements illustrated regarding the alloy of tin.

Specific examples of the alloy of tin and the compound of tin are $SnO_w$ ($0<w\leq2$), $SnSiO_3$, $LiSnO$ and $Mg_2Sn$.

In particular, it is preferable that the material containing tin as a constituent element is, for example, a material containing a second constituent element and a third constituent element together with tin that is a first constituent element (Sn-containing material). The second constituent element includes, for example, any one or two or more kinds of cobalt, iron, magnesium, titanium, vanadium, chromium, manganese, nickel, copper, zinc, gallium, zirconium, niobium, molybdenum, silver, indium, cesium (Ce), hafnium (Hf), tantalum, tungsten, bismuth and silicon. The third constituent element includes, for example, any one or two or more kinds of boron, carbon, aluminum and phosphorus. This is because the high battery capacity and the excellent cycle property are obtained by containing the second and third constituent elements in the Sn-containing material.

Inter alia, it is preferable that the Sn-containing material is a material containing, as a constituent element, tin, cobalt and carbon (SnCoC-containing material). In this SnCoC-containing material, for example, the content of carbon is 9.9% by mass to 29.7% by mass, and the ratio of the content of tin and that of cobalt (Co/(Sn+Co)) is 20% by mass to 70% by mass. This is because the high energy density is obtained.

It is preferable that the SnCoC-containing material has a phase containing tin, cobalt and carbon, and the phase is low crystalline or amorphous. Since this phase is a reaction phase that can react with lithium, the more excellent property is obtained due to existence of the reaction phase. A half-value width (diffraction angle 2θ) obtained by X-ray diffraction of this reaction phase is preferably 1° or more, when CuK☐ ray is used as characteristic X-ray, and at the same time, a sweep speed is 1°/min. This is because lithium is occluded and released more smoothly, and at the same time, the reactivity with the electrolytic solution is reduced. In addition, the SnCoC-containing material contains a phase in which a simple substance or a part of each constituent element is contained, in addition to a low crystalline or amorphous phase, in some cases.

Whether or not a diffraction peak obtained by X-ray diffraction corresponds to a reaction phase that can react with lithium can be easily determined when X-ray diffraction charts before and after an electrochemical reaction with lithium are compared. For example, if a position of the diffraction peak is changed between before and after the electrochemical reaction with lithium, this corresponds to the reaction phase that can react with lithium. In this case, for example, a diffraction peak of the low crystalline or amorphous reaction phase is seen between 2θ=20° to 50°. Such a reaction phase contains, for example, the above-mentioned each constituent element, and is considered to be low crystallized or non-crystallized due to, mainly, existence of carbon.

In the SnCoC-containing material, it is preferable that at least a part of carbon that is a constituent element is bound with the metal element and the semimetal element that are another constituent element. This is because aggregation or crystallization of tin is suppressed. The bound state of elements can be confirmed using, for example, X-ray photoelectron spectroscopy (XPS). In a commercially available apparatus, as soft X-ray, for example, Al-K☐ ray or Mg-K☐ ray is used. When at least a part of carbon is bound with the metal element or the semimetal element, a peak of an associated wave of 1s orbital of carbon (C1s) appears in a region at lower than 284.5 eV. In addition, it is assumed that the energy has been calibrated so that a peak of 4f orbital of a gold atom (Au4f) appears at 84.0 eV. Thereupon, usually, since surface-contaminating carbon exists on the substance surface, a peak of C1s of the surface-contaminating carbon is let to be 284.8 eV, and the peak is used as an energy standard. In XPS measurement, a waveform of the peak of C1s is obtained in a form containing a peak of the surface-contaminating carbon and a peak of carbon in the SnCoC-containing material. For this reason, peaks of both of them are separated, for example, by analysis using commercially available software. In analysis of a waveform, a position of a main peak existing on a minimum bound energy side is used as an energy standard (284.8 eV).

This SnCoC-containing material is not limited to a material containing only tin, cobalt and carbon as a constituent element (SnCoC). This SnCoC-containing material may further contain, as a constituent material, for example, any one or two or more kinds of silicon, iron, nickel, chromium, indium, niobium, germanium, titanium, molybdenum, aluminum, phosphorus, gallium and bismuth, in addition to tin, cobalt and carbon.

Besides the SnCoC-containing material, a material containing, as a constituent element, tin, cobalt, iron and carbon (SnCoFeC-containing material) is also preferable. The composition of this SnCoFeC-containing material is arbitrary. As an example, when the content of iron is set to be small, the content of carbon is 9.9% by mass to 29.7% by mass, the content of iron is 0.3% by mass to 5.9% by mass, and the ratio of the content of tin and that of cobalt (Co/(Sn+Co)) is 30% by mass to 70% by mass. Furthermore, when the content of iron is set to be large, the content of carbon is 11.9% by mass to 29.7% by mass, the ratio of the contents of tin, cobalt and iron ((Co+Fe)/(Sn+Co+Fe)) is 26.4% by mass to 48.5% by mass, and the ratio of contents of cobalt and iron (Co/(Co+Fe)) is 9.9% by mass to 79.5% by mass. This is because the high energy density is obtained in such a composition range. In addition, physical properties (half-value width etc.) of the SnCoFeC-containing material are the same as the above-mentioned physical properties of the SnCoC-containing material.

Besides this, the negative electrode material may be, for example, any one or two or more kinds of a metal oxide and a polymer compound. The metal oxide is, for example, iron oxide, ruthenium oxide and molybdenum oxide. The polymer compound is, for example, polyacetylene, polyaniline and polypyrrole.

Inter alia, it is preferable that the negative electrode material contains both of a carbon material and a metal-based material, for the following reason.

While the metal-based material, particularly, a material containing, as a constituent element, one or both of silicon and tin has an advantage that the theoretical capacity is high, it has the concern that it is vigorously easily expanded and shrunk at charging and discharging. On the other hand, while the carbon material has the concern that the theoretical capacity is low, it has an advantage that it is hardly expanded and shrunk at charging and discharging. Accordingly, by using both of the carbon material and the metal-based material, expansion and shrinkage at charging and discharging are suppressed, while the high theoretical capacity (in other words, battery capacity) is obtained.

The negative electrode active material layer 22B is formed, for example, by any one or two or more kinds of methods of a coating method, a vapor phase method, a liquid phase method, a thermal spraying method and a firing method (sintering method). The coating method is, for example, a method of mixing a particulate (powdery) negative electrode active material with a negative electrode binding agent and the like, dispersing the mixture in an organic solvent, and thereafter, coating the dispersion on the negative electrode current collector 22A. The vapor phase method is, for example, a physical depositing method and a chemical depositing method. More specifically, it is, for example, a vacuum depositing method, a sputtering method, an ion plating method, a laser ablation method, thermal chemical vapor deposition, a chemical vapor deposition (CVD) method and a plasma chemical vapor deposition method. The liquid phase method is, for example, an electrolytic plating method and a non-electrolytic plating method. The thermal spraying method is a method of spraying a negative electrode active material in the molten state or the semi-molten state to the negative electrode current collector 22A. The firing method is, for example, a method of coating a mixture dispersed in an organic solvent on the negative electrode current collector 22A using a coating method, and thereafter, heat-treating this at a temperature higher than a melting point of a negative electrode binding agent. As this firing method, for example, an atmospheric firing method, a reaction firing method and a hot press firing method can be used.

In this secondary battery, as described above, in order to prevent lithium from unintentionally precipitating on the negative electrode 22 during charging, the electrochemical equivalent of the negative electrode that can occlude and release lithium is larger than the electrochemical equivalent of the positive electrode. Furthermore, since when an open circuit voltage (i.e. battery voltage) at complete charge is 4.25 V or higher, a release amount of lithium per unit mass becomes larger even using the same positive electrode active material as compared with the case where the open circuit voltage at complete charge is 4.20 V, an amount of the positive electrode active material and the negative electrode active material are adjusted accordingly. Thereby, the high energy density is obtained.

The open circuit voltage at complete charge is not particularly limited, but 4.25 V or higher is preferable, as described above. Inter alia, the open circuit voltage at complete charge is more preferably 4.35 V or higher. This is because since an advantage due to the above-mentioned sulfonyl compound is obtained even when the open circuit voltage at complete charge is remarkably high, the excellent battery property is obtained.

The separator 23 is arranged, for example, between the positive electrode 21 and the negative electrode 22, as shown in FIG. 2. This separator 23 isolates the positive electrode 21 and the negative electrode 22, and at the same time, makes a lithium ion pass while short of current due to contact between both electrodes is prevented.

This separator 23 is, for example, any one or two or more kinds of a synthetic resin and a porous membrane such as ceramic, and may be a laminated membrane of two or more kinds of porous membranes. The synthetic resin is, for example, polytetrafluoroethylene, polypropylene and polyethylene.

In particular, the separator 23 may comprise, for example, the above-mentioned porous membrane (substrate layer), and a polymer compound layer provided on one side or both sides of the substrate layer. This is because since the close contact property of the separator 23 to each of the positive electrode 21 and the negative electrode 22 is improved, the strain of the wound electrode body 20 is suppressed. Thereby, since a decomposition reaction of the electrolytic solution is suppressed, and at the same time, liquid leakage of the electrolytic solution impregnated into the substrate layer is also suppressed, even when charge and discharge are repeated, rise in the resistance becomes difficult, and at the same time, battery swelling is suppressed.

The polymer compound layer contains, for example, a polymer compound such as polyvinylidene fluoride. This is because the polymer compound is excellent in the physical strength, and at the same time, is electrochemically stable. Provided that the polymer compound may be other than polyvinylidene fluoride. When this polymer compound layer is formed, for example, after a solution in which the polymer compound is dissolved in an organic solvent is coated on a substrate layer, the substrate layer is dried. In addition, after immersion of a substrate layer in a solution, the substrate layer may be dried. This polymer compound layer may contain, for example, any one or two or more kinds of insulating particles such as inorganic particles. A kind of the inorganic particles is, for example, aluminum oxide and aluminum nitride.

The wound electrode body 20 is impregnated with an electrolytic solution, as described above. This electrolytic solution has the same feature as that of the above-mentioned electrolytic solution of the present technology. That is, the electrolytic solution contains the sulfonyl compound.

This secondary battery operates, for example, as follows:

At charging, a lithium ion is released from the positive electrode 21, and at the same time, the lithium ion is occluded in the negative electrode 22 through the electrolytic solution. On the other hand, at discharging, a lithium ion is released from the negative electrode 22, and at the same time, the lithium ion is occluded in the positive electrode 21 through the electrolytic solution.

This secondary battery is manufactured, for example, by the following procedure:

When a positive electrode 21 is manufactured, first, a positive electrode active material and, as necessary, a positive electrode binding agent and a positive electrode conducting agent are mixed, thereby, to prepare a positive electrode mixture. Subsequently, the positive electrode mixture is dispersed in an organic solvent, thereby, to prepare pasty positive electrode mixture slurry. Subsequently, after the positive electrode mixture slurry is coated on both sides of a positive electrode current collector 21A, the positive electrode mixture slurry is dried, thereby, to form a positive electrode active material layer 21B. Subsequently, the positive electrode active material layer 21B is compression-molded using a roll press machine while the positive electrode active material layer 21B is heated, as necessary. In this case, compression molding may be repeated plural times.

When a negative electrode 22 is manufactured, according to the same procedure as the above-mentioned procedure of the positive electrode 21, a negative electrode active material layer 22B is formed on both sides of a negative electrode current collector 22A. Specifically, after a negative active material, a negative electrode binding agent and a negative electrode conducting agent are mixed, thereby, to prepare a negative electrode mixture, the negative electrode mixture is dispersed in an organic solvent, thereby, to prepare pasty negative electrode mixture slurry. Subsequently, after the negative electrode mixture slurry is coated on both sides of the negative electrode current collector 22A, the negative electrode mixture slurry is dried, thereby, to form a negative active material layer 22B. Finally, the negative electrode active material layer 22B is compression-molded using a roll press machine.

When a secondary battery is assembled, a positive electrode lead 25 is attached to the positive electrode current collector 21A using a welding method, and at the same time, a negative electrode lead 26 is attached to the negative electrode current collector 22A using a welding method. Subsequently, after the positive electrode 21 and the negative electrode 22 are laminated with a separator 23 interposed therebetween, the positive electrode 21, the negative electrode 22 and the separator 23 are wound, thereby, to form a wound electrode body 20. Subsequently, a center pin 24 is inserted into a winding center of the wound electrode body 20.

Subsequently, the wound electrode body 20 is housed in the interior of a battery can 11 while the wound electrode body 20 is held with one pair of insulating plates 12, 13. In this case, a tip portion of the positive electrode lead 25 is attached to a safety valve mechanism 15 using a welding method, and at the same time, a tip portion of the negative electrode lead 26 is attached to a battery can 11 using a welding method. Subsequently, an electrolytic solution is injected into the interior of the battery can 11, thereby, the electrolytic solution is impregnated into the wound electrode body 20. Finally, a battery lid 14, the safety valve mechanism 15 and a heat-sensitive resistive element 16 are crimped to an opening end of the battery can 11 with a gasket 17 interposed therebetween. Thereby, a cylindrical type secondary battery is completed.

According to this cylindrical type lithium secondary battery, since the electrolytic solution has the same feature as that of the electrolytic solution of the present technology, a decomposition reaction of the electrolytic solution is suppressed at use of the secondary battery (at charging and discharging) and at preservation thereof. Accordingly, the excellent battery property can be obtained. Action and effect other than this are the same as the action and the effect regarding the electrolytic solution of the present technology.

Figure 3:
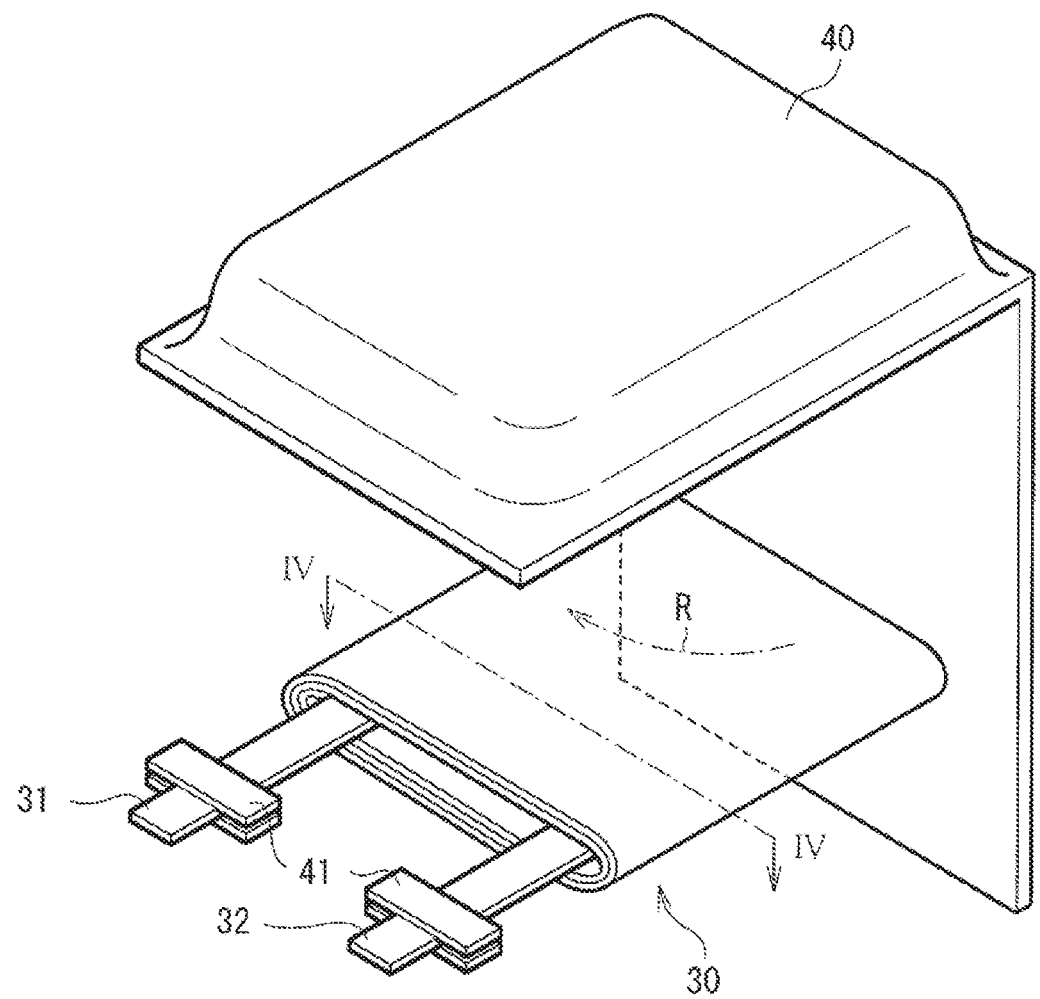
FIG. 3 is a perspective representing constituent features of a secondary battery (laminate film type) of an embodiment of the present technology.
Figure 4:
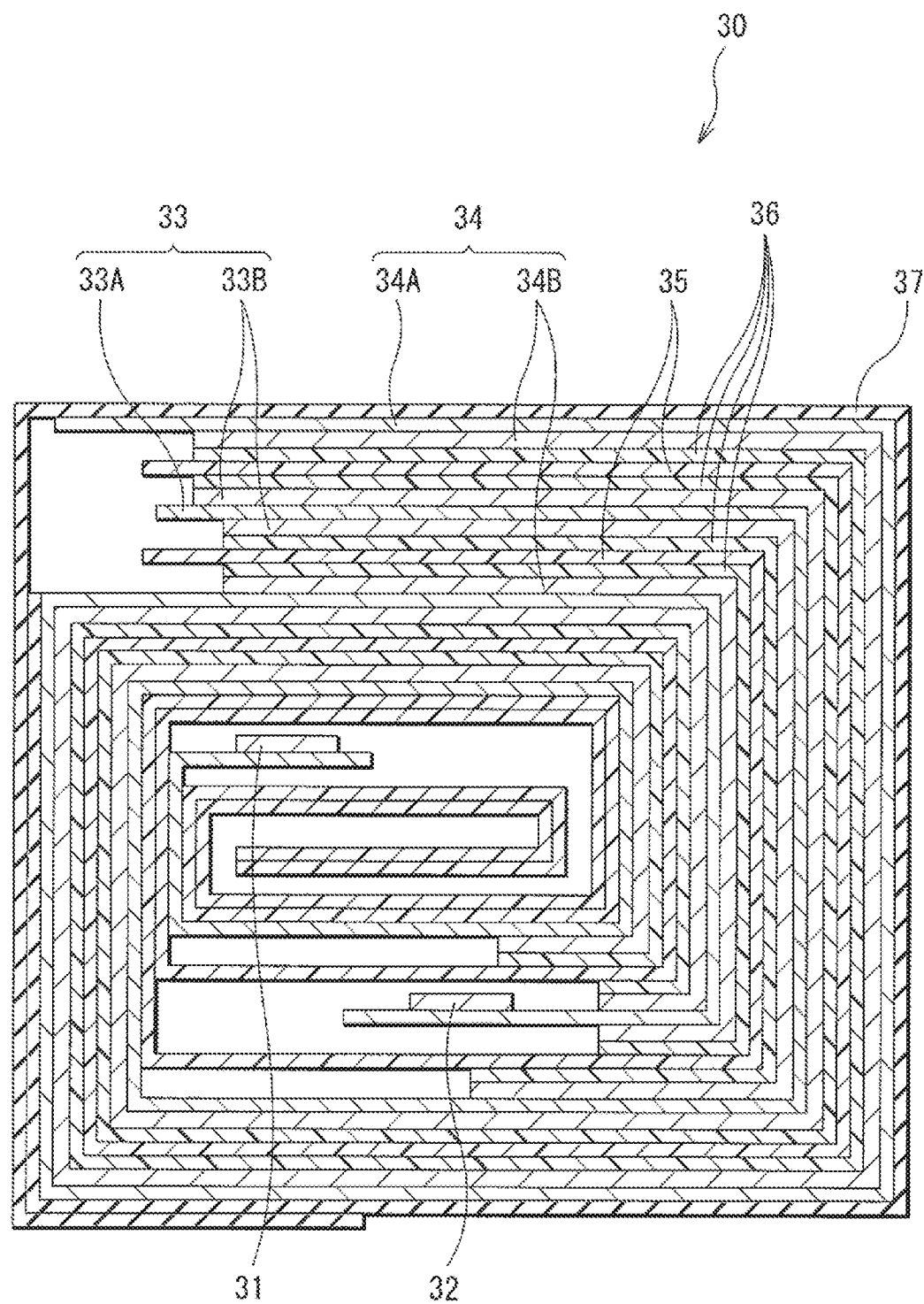
FIG. 4 is a cross-sectional view of a wound electrode body along IV-IV line shown in FIG. 3.

FIG. 3 represents a perspective configuration of another secondary battery, and FIG. 4 represents a cross section along IV-IV line of a wound electrode body 30 shown in FIG. 3. In addition, in FIG. 3, the state where the wound electrode body 30 and an exterior member 40 are separated is shown.

In the following illustration, the components of the cylindrical type secondary battery already illustrated will be referred as required.

This secondary battery is a lithium ion secondary battery having a so-called laminate film type, and for example, as shown in FIG. 3, a wound electrode body 30 that is a battery element is housed in the interior of a film-like exterior member 40. In the wound electrode body 30, for example, after a positive electrode 33 and a negative electrode 34 are laminated with a separator 35 and an electrolyte layer 36 interposed therebetween, the positive electrode 33, the negative electrode 34, the separator 35 and the electrolyte layer 36 are wound. A positive lead 31 is attached to the positive electrode 33, and at the same time, a negative electrode lead 32 is attached to the negative electrode 34. An outermost circumferential part of the wound electrode body 30 is protected with a protective tape 37.

Each of the positive electrode lead 31 and the negative electrode lead 32 is derived to, for example, the same direction towards the outside from the interior of the exterior member 40. The positive lead 31 contains, for example, any one or two or more kinds of an electrically conductive material such as aluminum (Al). The negative electrode lead 32 contains, for example, one or two or more kinds of an electrically conductive material such as copper (Cu), nickel (Ni) and stainless steel. These electrically conductive materials are, for example, thin plate-like or net-like.

The exterior member 40 is, for example, one film that is foldable to a direction of an arrow R shown in FIG. 3, and a depression for housing the wound electrode body 30 is provided on a part of the exterior member 40. This exterior member 40 is, for example, a laminated film in which a fusion layer, a metal layer and a surface protective layer are laminated in this order. In a step of manufacturing a secondary battery, after the exterior member 40 is folded so that fusion layers are opposite with the wound electrode body 30 interposed therebetween, external circumferential edges of the fusion layers are fused. Provided that the exterior member 40 may be a member obtained by sticking two laminate films through an adhesive agent. The fusion layer is, for example, any one or two or more films of polyethylene and polypropylene. The metal layer is, for example, any one or two or more kinds of an aluminum foil. The surface protective layer is, for example, any one or two or more kinds of films of nylon and polyethylene terephthalate.

Inter alia, the exterior member 40 is preferably an aluminum laminate film in which a polyethylene film, an aluminum foil and a nylon film are laminated in this order. Provided that the exterior member 40 may be a laminate film having another lamination structure, may be a polymer film such as polypropylene, or may be a metal film.

Between the exterior member 40 and the positive electrode lead 31, for example, a close contact film 41 is inserted in order to prevent the entrance of outside air. Furthermore, between the exterior member 40 and the negative electrode lead 32, for example, above-mentioned close contact film 41 is inserted. This close contact film 41 contains a material having the close contact property to both of the positive electrode lead 31 and the negative electrode lead 32. This material having the close contact property is, for example, a polyolefin resin, more specifically, any one or two or more kinds of polyethylene, polypropylene, modified polyethylene and modified polypropylene.

The electrode 33 comprises, for example, a positive electrode current collector 33A and a positive electrode active material layer 33B, and at the same time, the negative electrode 34 comprises, for example, a negative electrode current collector 34A and a negative electrode active material layer 34B. A configuration of each of the positive electrode current collector 33A, the positive electrode active material layer 33B, the negative electrode current collector 34A and the negative electrode active material layer 34B is, for example, the same as the configuration of each of the positive electrode current collector 21A, the positive electrode active material layer 21B, the negative electrode current collector 22A and the negative electrode active material layer 22B. A configuration of the separator 35 is, for example, the same as the configuration of the separator 23.

The electrolyte layer 36 contains an electrolytic solution and a polymer compound, and the electrolytic solution has the same feature as that of the electrolytic solution of the present technology. That is, the electrolytic solution contains the sulfonyl compound. The electrolyte layer 36 illustrated herein is a so-called gel-like electrolyte, and the electrolytic solution is retained by the polymer compound. This is because the high ion conductivity (for example, 1 mS/cm or more at room temperature) is obtained, and at the same time, liquid leakage of the electrolytic solution is prevented. In addition, the electrolyte layer 36 may further contain any one or two or more kinds of other materials such as an additive.

The polymer compound includes, for example, any one or two or more kinds of polyacrylonitrile, polyvinylidene fluoride, polytetrafluoroethylene, polyhexafluoropropylene, polyethylene oxide, polypropylene oxide, polyphosphazene, polysiloxane, polyvinyl fluoride, polyvinyl acetate, polyvinyl alcohol, polymethyl methacrylate, polyacrylic acid, polymethacrylic acid, styrene-butadiene rubber, nitrile-butadiene rubber, polystyrene and polycarbonate. Besides this, the polymer compound may be a copolymer. This copolymer is, for example, a copolymer of vinylidene fluoride and hexafluoropyrene. Inter alia, as a homopolymer, polyvinylidene fluoride is preferable, and as a copolymer, a copolymer of vinylidene fluoride and hexafluoropyrene is preferable. This is because they are electrochemically stable.

In the electrolyte layer 36 that is a gel-like electrolyte, a solvent contained in the electrolytic solution is a broad conception including not only a liquid material, but also a material having the ion conductivity, which can dissociate an electrolyte salt. Accordingly, when a polymer compound having the ion conductivity is used, the polymer compound is also contained in a non-aqueous solvent.

In addition, in place of the electrolyte layer 36, the electrolytic solution may be used as it is. In this case, the electrolytic solution is impregnated into the wound electrode body 30.

This secondary battery operates, for example, as follows:

At charging, a lithium ion is released from the positive electrode 33, and at the same time, the lithium ion is occluded in the negative electrode 34 through the electrolyte layer 36. On the other hand, at discharging, a lithium ion is released from the negative electrode 34, and at the same time, the lithium ion is occluded in the positive electrode 33 through the electrolyte layer 36.

A secondary battery equipped with the gel-like electrolyte 36 is manufactured, for example, by the following three kinds of procedures.

In a first procedure, by the same procedure as the procedure of manufacturing the positive electrode 21 and the negative electrode 22, the positive electrode 33 and the negative electrode 34 are manufactured. That is, when the positive electrode 33 is manufactured, the positive electrode active material layer 33B is formed on both sides of the positive electrode current collector 33A, and when the negative electrode 34 is manufactured, the negative electrode active material layer 34B is formed on both sides of the negative electrode current collector 34A.

Subsequently, an electrolytic solution, a polymer compound, and an organic solvent are mixed, thereby, to prepare a precursor solution. Subsequently, after the precursor solution is coated on the positive electrode 33, the precursor solution is dried, thereby, to form the gel-like electrolyte layer 36. Furthermore, after the precursor solution is coated on the negative electrode 34, the precursor solution is dried, thereby, to form the gel-like electrolyte layer 36.

Subsequently, the positive electrode lead 31 is attached to the positive electrode current collector 33A using a welding method, and at the same time, the negative electrode lead 32 is attached to the negative electrode current collector 34A using a welding method. Subsequently, after the positive electrode 33 and the negative electrode 34 are laminated with the separator 35 interposed therebetween, the positive electrode 33, the negative electrode 34 and the separator 35 are wound, thereby, to form the wound electrode body 30. Subsequently, the protective tape 37 is stuck to an outermost circumferential part of the wound electrode body 30. Subsequently, after the exterior member 40 is folded so as to hold the wound electrode body 30, external circumferential edges of the external member 40 are adhered using a thermal fusion method, thereby, the wound electrode body 30 is enclosed in the interior of the exterior member 40. In this case, the close contact film 41 is inserted between the positive electrode lead 31 and the exterior member 40, and at the same time, the close contact film 41 is inserted between the negative electrode lead 32 and the exterior member 40.

In a second procedure, the positive electrode lead 31 is attached to the positive electrode 33, and at the same time, the negative electrode lead 32 is attached to the negative electrode 34.

Subsequently, after the positive electrode 33 and the negative electrode 34 are laminated with the separator 35 interposed therebetween, they are wound, thereby, to manufacture a wound body that is a precursor of the wound electrode body 30, and thereafter, the protective tape 37 is stuck to an outermost circumferential part of the wound body. Subsequently, after the exterior member 40 is folded so as to fold the wound electrode body 30, remaining external circumferential edges except for an external circumferential edge of one side of the exterior member 40 are bonded using a thermal fusion method, thereby, the wound body is housed in the interior of a bag-like exterior member 40.

Subsequently, an electrolytic solution, a monomer that is a raw material of a polymer compound, a polymerization initiator and, optionally, another material such as a polymerization inhibitor are mixed, thereby, to prepare a composition for an electrolyte. Subsequently, after the composition for an electrolyte is injected into the interior of the bag-like exterior member 40, the exterior member 40 is sealed using a thermal fusion method. Subsequently, the monomer is thermally polymerized, thereby, to form a polymer compound. Thereby, since the electrolytic solution is retained by the polymer compound, the gel-like electrolyte layer 36 is formed.

In a third procedure, according to the same manner as that of the above-mentioned second procedure except that the separator 35 on which a polymer compound layer is formed is used, a wound body is prepared, and is housed in the interior of the bag-like exterior member 40.

Subsequently, after an electrolytic solution is prepared, and injected into the interior of the exterior member 40, a cavity of the exterior member 40 is sealed using a thermal fusion method. Subsequently, by heating while a load is applied to the exterior member 40, the separator 35 is brought into close contact with the positive electrode 33 with a polymer compound layer interposed therebetween, and at the same time, the separator 35 is brought into close contact with the negative electrode 34 with a polymer compound layer interposed therebetween. Thereby, since the electrolytic solution is impregnated into each of the polymer compound layers, and at the same time, each of the polymer compound layers is gelled, the electrolyte layer 36 is formed.

In this third procedure, swelling of the secondary battery is suppressed more than in the first procedure. Furthermore, in the third procedure, since a non-aqueous solvent and a monomer (raw material of polymer compound) remain little in the electrolyte layer 36 as compared with the second procedure, a step of forming the polymer compound is controlled good. For this reason, each of the positive electrode 33, the negative electrode 34 and the separator 35, and the electrolyte layer 36 are sufficiently brought into close contact.

According to this laminate film type lithium ion secondary battery, since the electrolyte layer 36 contains the electrolytic solution, and the electrolytic solution has the same feature as that of the electrolytic solution of the present technology, the excellent battery property can be obtained, for the same reason as that of the above-mentioned cylindrical type lithium ion secondary battery. Action and effect other than this are the same as the action and effect regarding the cylindrical type lithium ion secondary battery.

A secondary battery illustrated herein is a cylindrical type lithium metal secondary battery in which the capacity of the negative electrode 22 is obtained by precipitation and dissolution of a lithium metal. This secondary battery has the same configuration as that of the above-mentioned cylindrical type lithium ion secondary battery except that the negative electrode active material layer 22B is formed of a lithium metal, and it is manufactured by the same procedure.

In this secondary battery, since a lithium metal is used as a negative electrode active material, the high energy density is obtained. The negative electrode active material layer 22B may exist already from the time of assembling, but it does not exist at the time of assembling, and may be formed of a lithium metal that is precipitated at charging. Furthermore, by utilizing the negative electrode active material layer 22B as a current collector, the negative electrode current collector 22A may be omitted.

This secondary battery operates, for example, as follows: At charging, a lithium ion is released from the positive electrode 21, and at the same time, the lithium ion becomes a lithium metal to precipitate on the surface of the negative electrode current collector 22A through the electrolytic solution. On the other hand, at discharging, a lithium metal becomes a lithium ion and is dissolved from the negative electrode active material layer 22B into the electrolytic solution, and at the same time, the lithium ion is occluded in the positive electrode 21 through the electrolytic solution.

According to this cylindrical type lithium metal secondary battery, since the electrolytic solution has the same feature as that of the electrolytic solution of the present technology, the excellent battery property can be obtained, for the same reason as that of the above-mentioned lithium ion secondary battery. Action and effect other than this is the same as the action and effect regarding the lithium ion secondary battery.

In addition, a configuration of the lithium metal secondary battery illustrated herein may be applied to a laminate film type secondary battery in place of the cylindrical type secondary battery. Also in this case, the same effect can be obtained.

Then, an application example of the above-mentioned secondary battery will be illustrated.

Intended use of the secondary battery is not particularly limited, as long as it is a machine, equipment, an instrument, a device and a system (aggregate of a plurality of pieces of equipment), in which the secondary battery can be utilized as an electric power source for driving or an electric power storage source for electric power accumulation. The secondary battery which is used as an electric power source may be a main electric power source, or may be an auxiliary electric power source. The main electric power source is an electric power source that is used preferentially, irrespective of the presence or absence of another electric power source. The auxiliary electric power source may be, for example, an electric power source which is used in place of the main electric power source, or may be an electric power source which is switched from the main electric power source, as required. When the secondary battery is used as the auxiliary electric power source, a kind of the main electric power source is not limited to the secondary battery.

Intended use of the secondary battery is, for example, as follows: Electronic equipment (including portable electronic equipment) such as a video camera, a digital still camera, a cellular phone, a notebook-type personal computer, a cordless telephone, a headphone stereo, a portable radio, a portable television and a personal digital assistant. A portable life instrument such as an electric shaver. A storage device such as a backup power supply and a memory card. An electric tool such as an electric drill and an electric saw. A battery pack that is mounted in a notebook-type personal computer as a detachable electric power source. Medical electronic equipment such as a pacemaker and a hearing aid. An electrically driven vehicle such as an electric car (including a hybrid automobile). An electric power storage system such as a home battery system, which stores electric power for emergencies. Of course, intended use of the secondary battery may be intended use other than the above-mentioned intended uses.

Inter alia, it is effective that the secondary battery is applied to a battery pack, an electrically driven vehicle, an electric power storage system, an electric tool and electronic equipment. This is because since the excellent battery property is required in these intended uses, improvement in performance can be effectively realized by using the secondary battery of the present technology. In addition, the battery pack is an electric power source using the secondary battery. This battery pack may use a single battery, or may use an assembled battery, as described later. The electrically driven vehicle is a vehicle that operates (runs) using the secondary battery as an electric power source for driving, and may be an automobile also equipped with a driving source other than the secondary battery (hybrid automobile etc.), as described above. The electric power storage system is a system using the secondary battery as an electric power storage source. For example, in a home electric power storage system, since the electric power is accumulated in the secondary battery which is an electric power storage source, it is possible to use home electric products utilizing the electric power. The electric tool is a tool in which a movable part (for example, drill etc.) is moved using the secondary battery as an electric power source for driving. Electronic equipment is equipment that exerts various functions utilizing the secondary battery as an electric power source for driving (electric power supply source).

Herein, some application examples of the secondary battery will be specifically illustrated. In addition, since configurations of the application examples illustrated below are just an example, the configurations of the application examples can be appropriately changed.

Figure 5:
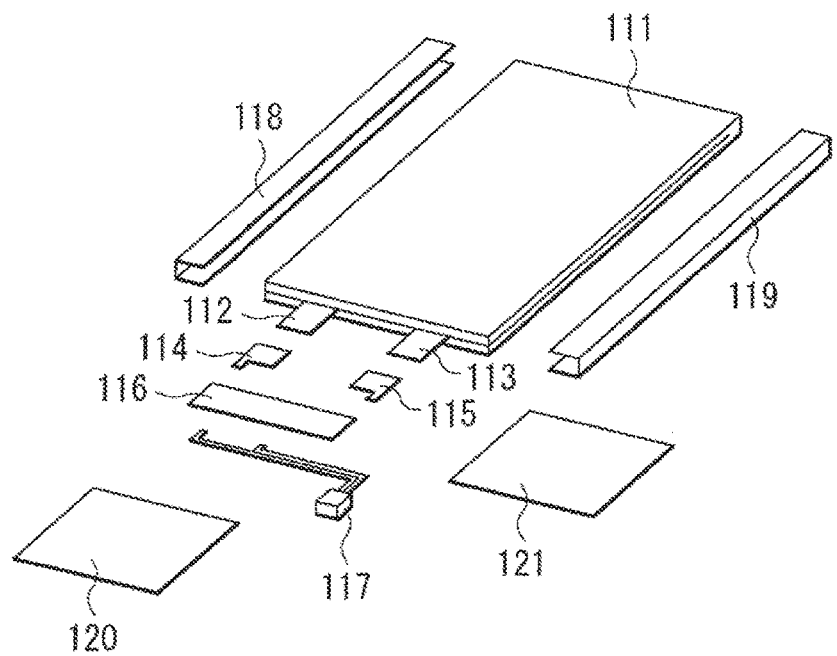
FIG. 5 is a perspective representing constituent features of an application example of a secondary battery (battery pack:single battery) according to an embodiment of the present technology.
Figure 6:
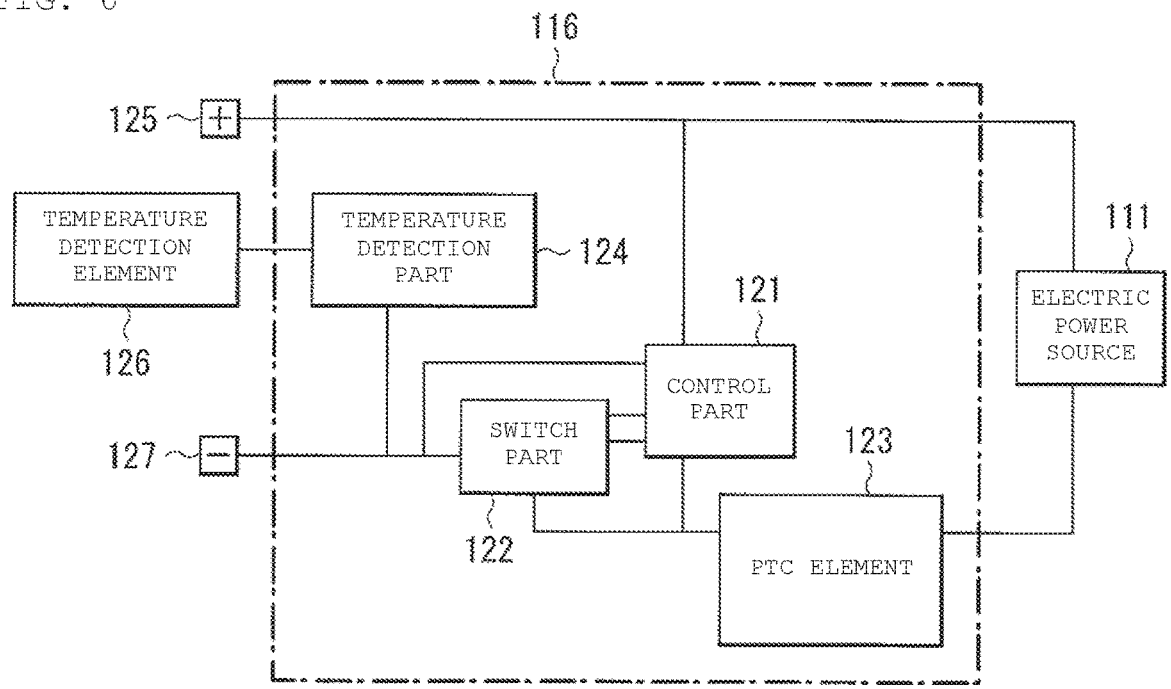
FIG. 6 is a block diagram representing constituent features of a battery pack shown in FIG. 5.

FIG. 5 represents a perspective configuration of a battery pack using a single battery. FIG. 6 represents a block configuration of a battery pack shown in FIG. 5. In addition, in FIG. 5, the state where a battery pack has been disassembled is shown.

A battery pack illustrated herein is a simplified battery pack (so-called soft pack) using one secondary battery of the present technology, and is mounted in electronic equipment typified by a smartphone. This battery pack is provided with, for example, an electric power source 111 that is a laminate film type secondary battery, and a circuit board 116 connected to the electric power source 111, as shown in FIG. 5. A positive electrode lead 112 and a negative electrode lead 113 are attached to this electric power source 111.

One pair of pressure-sensitive adhesive tapes 118, 119 are stuck to both side faces of the electric power source 111. On the circuit board 116, a protection circuit (PCM: Protection Circuit Module) is formed. This circuit board 116 is connected to the positive electrode 112 with a tab 114 interposed therebetween, and at the same time, is connected to the negative electrode lead 113 with a tab 115 interposed therebetween. Furthermore, the circuit board 116 is connected to a lead wire 117 with a connector for external connection. In addition, in the state where the circuit board 116 is connected to the electric power source 111, the circuit board 116 is protected with a label 120 and an insulating sheet 121. By sticking this label 120, the circuit board 116 and the insulating sheet 121 are fixed.

One again, the battery pack is provided with, for example, an electric power source 111 and a circuit board 116, as shown in FIG. 6. The circuit board 116 is provided with, for example, a control part 121, a switch part 122, a PTC element 123, and a temperature detection part 124. Since the electric power source 111 can be connected to the outside through a positive electrode terminal 125 and a negative electrode terminal 127, the electric power source 111 is charged and discharged through the positive electrode terminal 125 and the negative electrode terminal 127. The temperature detection part 124 detects the temperature using a temperature detection terminal (so-called T terminal) 126.

The control part 121 controls operation (including the use state of the electric power source 111) of a whole battery pack. This control part 121 comprises, for example, a central processing unit (CPU) and a memory.

This control part 121 prevents a charging current from flowing through a current path of the electric power source 111 by disconnecting the switch part 122, for example, when a battery voltage reaches an overcharge detection voltage. Furthermore, the control part 121 interrupts a charging current by disconnecting the switch part 122, for example, when a large current has flown at charging.

Meanwhile, the control part 121 prevents a discharging current from flowing through a current path of the electric power source 111 by disconnecting the switch part 122, for example, when a battery voltage reaches an overdischarge detection voltage. Furthermore, the control part 121 interrupts a discharging current by disconnecting the switch part 122, for example, when a large current has flown at discharging.

In addition, the overcharge detection voltage is, for example, 4.2 V±0.05 V, and the overdischarge detection voltage is, for example, 2.4 V±0.1 V.

The switch part 122 switches the use state of the electric power source 111, that is, the presence or absence of connection between the electric power source 111 and external equipment, in response to an instruction of the control part 121. This switch part 122 comprises, for example, a charge control switch and a discharge control switch. Each of the charge control switch and the discharge control switch is, for example, a semiconductor switch such as a field effect transistor using a metal oxide semiconductor (MOSFET). In addition, a charging and discharging current is detected, for example, based on the ON resistance of the switch part 122.

The temperature detection part 124 measures a temperature of the electric power source 111, and at the same time, outputs the measurement result of the temperature to the control part 121. This temperature detection part 124 comprises, for example, a temperature detection element such as a thermistor. In addition, the measurement result of the temperature measured by the temperature detection part 124 is used when the control part 121 performs charge and discharge control at abnormal heat generation, and when the control part 121 performs correction processing at calculation of the remaining capacity.

In addition, the circuit board 116 need not comprise the PTC element 123. In this case, the PTC element may be annexed to the circuit board 116 separately.

Figure 7:
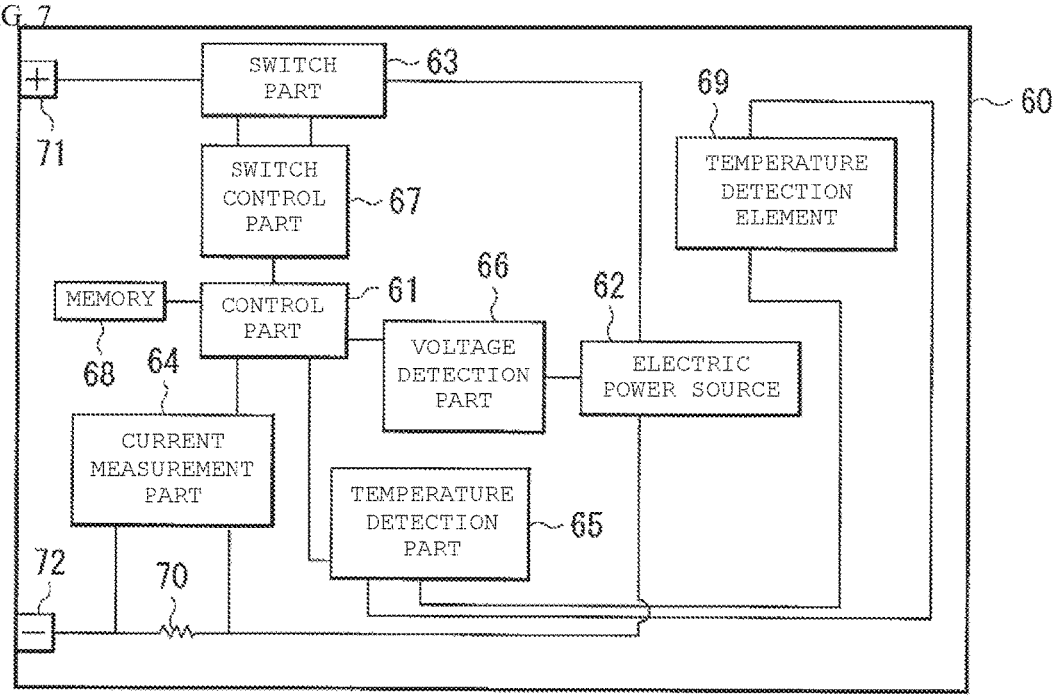
FIG. 7 is a block diagram representing constituent features of an application example of a secondary battery (battery pack: assembled battery) according to an embodiment of the present technology.

FIG. 7 represents a block configuration of a battery pack using an assembled battery.

This battery pack comprises, for example, a control part 61 (controller), an electric power source 62, a switch part 63, a current measurement part 64, a temperature detection part 65, a voltage detection part 66, and a switch control part 67, a memory 68, a temperature detection element 69, a current detection resistance 70, a positive electrode terminal 71 and a negative electrode terminal 72 in the interior of a housing 60. This housing 60 contains, for example, a plastic material.

The control part 61 controls operation (including the use state of the electric power source 62) of a whole battery pack. This control part 61 (controller) comprises, for example, CPU or a processor. The electric power source 62 is an assembled battery comprising two or more kinds of the secondary batteries of the present technology, and a mode of connecting the two or more kinds of the secondary batteries may be serial, parallel, or a mixed type of both of them. As an example, the electric power source 62 comprises six secondary batteries which are connected so as to be two parallel and three serial.

The switch part 63 switches the use state of the electric power source 62, that is, the presence or absence of connection between the electric power source 62 and external equipment, in response to an instruction of the control part 61. This switch part 63 comprises, for example, a charge control switch, a discharge control switch, a diode for charging and a diode for discharging. Each of the charge control switch and the discharge control switch is, for example, a semiconductor switch such as a field effect transistor using a metal oxide semiconductor (MOSFET).

The current measurement part 64 measures current using the current detection resistance 70, and at the same time, outputs the measurement result of the current to the control part 61. The temperature detection part 65 measures temperature using the temperature detection element 69, and at the same time, outputs the measurement result of the temperature to the control part 61. This measurement result of the temperature is used, for example, when the control part 61 performs charge and discharge control at abnormal heat generation, and when the control part 61 performs correction processing at calculation of the remaining capacity. The voltage detection part 66 measures a voltage of the secondary battery in the electric power source 62, and at the same time, supplies the measurement result of the voltage which has been subjected to analog/digital conversion, to the control part 61.

The switch control part 67 controls operation of the switch part 63, in response to a signal inputted from each of the current measurement part 64 and the voltage detection part 66.

This switch control part 67 prevents a charging current from flowing through a current path of the electric power source 62 by disconnecting the switch part 63 (charge control switch), for example, when a battery voltage reaches an overcharge defection voltage. Thereby, at the electric power source 62, only discharge becomes possible through the diode for discharging. In addition, the switch control part 67 interrupts a charging current, for example, when a large current has flown at charging.

Furthermore, the switch control part 67 prevents a discharging current from flowing through a current path of the electric power source 62 by disconnecting the switch part 63 (discharge control switch), for example, when a battery voltage reaches an overdischarge detection voltage. Thereby, at the electric power source 62, only charge becomes possible through the diode for charging. In addition, the switch control part 67 interrupts a discharging current, for example, when a large current has flown at discharging.

In addition, the overcharge detection voltage is, for example, 4.2 V±0.05 V, and the overdischarge detection voltage is, for example, 2.4 V±0.1 V.

The memory 68 comprises, for example, EEPROM that is a nonvolatile memory. In this memory 68, for example, numerical values operated by the control part 61, and information of the secondary battery measured at a stage of a manufacturing step (for example, internal resistance at the initial state) are stored. In addition, when the full charge capacity of the secondary battery is stored in the memory 68, the control part 61 can grasp information such as the remaining capacity.

The temperature detection element 69 measures temperature of the electric power source 62, and at the same time, outputs the measurement result of the temperature to the control part 61. This temperature detection element 69 comprises, for example, a thermistor.

Each of the positive electrode terminal 71 and the negative electrode terminal 72 is a terminal connected to external equipment (for example, notebook-type personal computer etc.) that works using the battery pack, or external equipment (for example, battery charger) that is used for charging the battery pack. The electric power source 62 is charged and discharged through the positive electrode terminal 71 and the negative electrode terminal 72.

Figure 8:
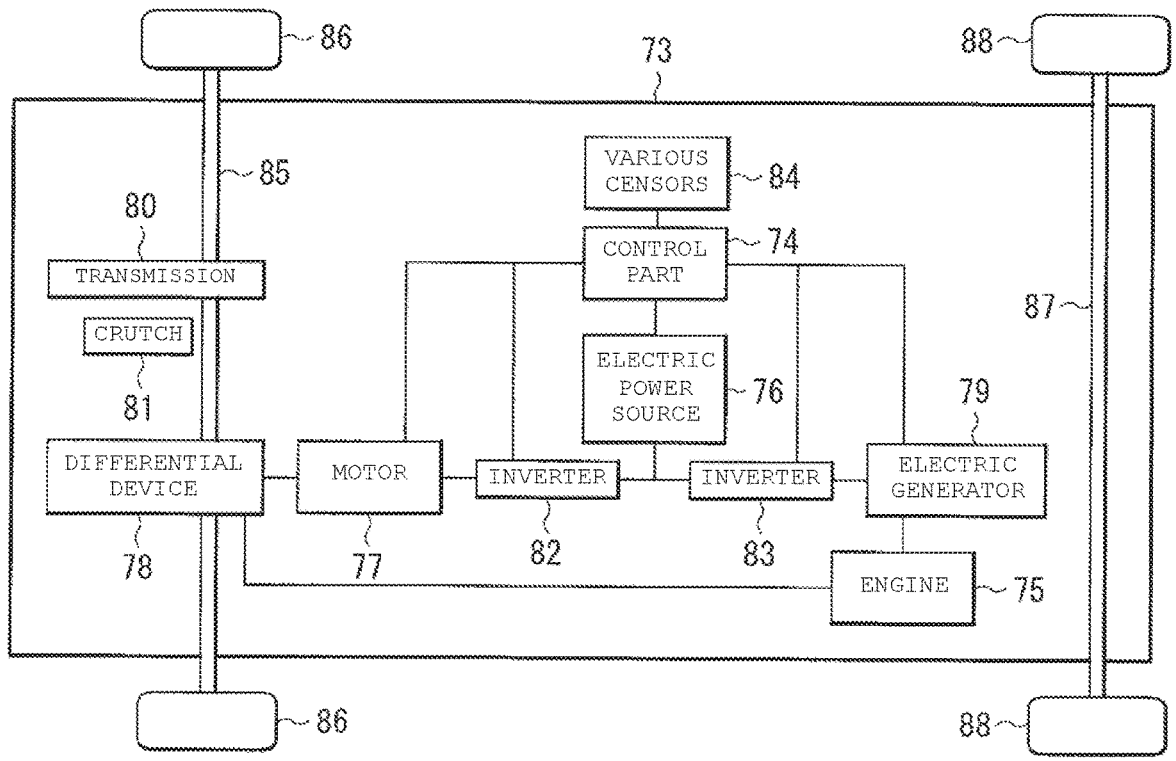
FIG. 8 is a block diagram representing constituent features of an application example of a secondary battery (electrically driven vehicle) according to an embodiment of the present technology.

FIG. 8 represents a block configuration of a hybrid automobile which is an example of the electrically driven vehicle.

This electrically driven vehicle is provided with, for example, a control part 74 (controller), an engine 75, an electric power source 76, a motor 77 for driving, a differential device 78, an electrical generator 79, a transmission 80 and a clutch 81, inverters 82, 83, and various sensors 84, in the interior of a housing 73 made of metal. Besides this, the electrically driven vehicle is provided with, for example, a driving axis for a front wheel 85, which is connected to a differential device 78 and a transmission 80, and front wheels 86, as well as a driving axis for a rear wheel 87 and rear wheels 88.

This electrically driven vehicle can run using, for example, any one of an engine 75 and a motor 77 as a driving source. The engine 75 is a main power source, and is, for example, a gasoline engine. When the engine 75 is used as a power source, a driving force (rotative force) of the engine 75 is transmitted to the front wheels 86 and the rear wheels 88, for example, through the differential device 78, the transmission 80 and the clutch 81, which are a driving part. In addition, since a rotative force of the engine 75 is transmitted to the electrical generator 79, the electrical generator 79 generates AC power utilizing the rotative force, and at the same time, since the AC power is converted into DC power through the inverter 83, the DC power is accumulated in the electric power source 76. On the other hand, when the motor 77 that is a converter is used as the power source, electric power (DC power) supplied from the electric power source 76 is converted into AC power through the inverter 82, the motor 77 is driven utilizing the AC power. The driving force (rotative force) that was converted from the electric power by this motor 77 is transmitted to the front wheels 86 and the rear wheels 88 though the differential device 78, the transmission 80 and the clutch 81, which are a driving part (driver).

In addition, when the electrically driven vehicle reduces the speed through a control mechanism, since a resistive force at the reduction in the speed is transmitted to the motor 77 as a rotative force, it may be configured that the motor 77 generates AC power utilizing the rotative force. Since this AC power is converted into DC power through the inverter 82, DC regenerative power is preferably accumulated in the electric power source 76.

The control part 74 controls operation of a whole electrically driven vehicle. This control part 74 (controller) comprises, for example, CPU or processor. The electric power source 76 comprises one or two or more kinds of the secondary batteries of the present technology. This electric power source 76 is connected to an external electric power source, and at the same time, it may be made to accumulate the electric power by receiving electric power supply from the external electric power source. Various sensors 84 are used, for example, in order to control a rotation number of the engine 75, and at the same time, control opening of a throttle valve (throttle opening). These various sensors 84 comprise, for example, any one or two or more kinds of a speed sensor, an acceleration sensor and an engine rotation number sensor.

In addition, the case where the electrically driven vehicle is a hybrid automobile was illustrated as an example, and the electrically driven vehicle may a vehicle that operates not using the engine 75, but using only the electric power source 76 and the motor 77 (electric car).

Figure 9:
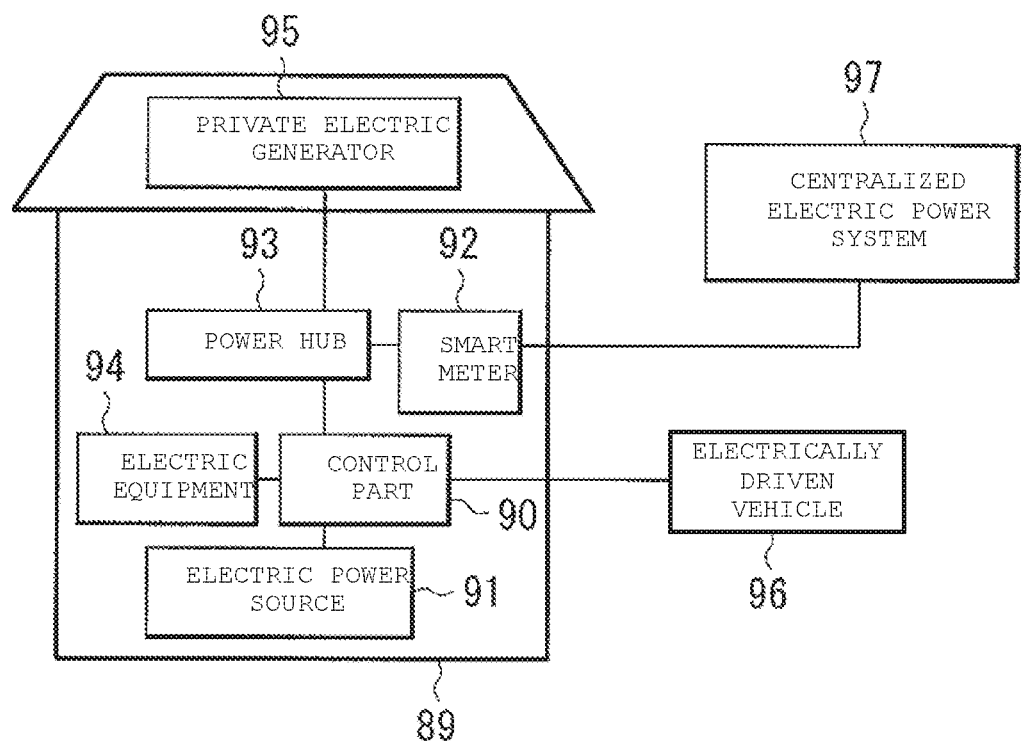
FIG. 9 is a block diagram representing constituent features of an application example of a secondary battery (electric power storage system) according to an embodiment of the present technology.

FIG. 9 represents a block configuration of an electric power storage system.

This electric power storage system is provided with, for example, a control part 90 (controller), an electric power source 91, a smart meter 92, and a power hub 93, in the interior of a house 89 such as a conventional home and a commercial building.

Herein, it is possible that, for example, the electric power source 91 is connected to electric equipment 94 arranged in the interior of the house 89, and at the same time, is connected to an electrically driven vehicle 96 which is stopped outside the house 89. Furthermore, it is possible that, for example, the electric power source 91 is connected to a private power generator 95 arranged in the house 89 through the power hub 93, and at the same time, is connected to an external centralized electric power system 97 through the smart meter 92 and the power hub 93.

In addition, the electric equipment 94 comprises, for example, one or two or more kinds of home electric appliances, and the home electric appliances are, for example, a refrigerator, an air conditioner, a television and a water heater. The private electric generator 95 comprises, for example, one or two or more kinds of a solar photovoltaic power generator and a wind power generator. The electrically driven vehicle 96 comprises, for example, any one or two or more kinds of an electric car, an electric motor cycle and a hybrid automobile. The centralized electric power system 97 comprises, for example, any one or two or more kinds of a thermal power station, a nuclear power station, a hydraulic power station and a wind power station.

The control part 90 controls operation (including the use state of the electric power source 91) of a whole electric power storage system. This control part 90 (controller) comprises, for example, CPU or processor. The electric power source 91 comprises one or two or more kinds of the secondary batteries of the present technology. The smart meter 92 is, for example, a network-compatible wattmeter mounted in the house 89 on an electric power demand side, and can communicate with an electric power supply side. Accordingly, the smart meter 92 can stably supply the energy at the high efficiency, for example, by controlling the balance between demand and supply of the electric power in the house 89 while communicating with the outside.

In this electric power storage system, for example, the electric power is accumulated in the electric power source 91 from the centralized electric power system 97 that is an external electric power source, through the smart meter 92 and the power hub 93, and at the same time, the electric power is accumulated in the electric power source 91 from the private power generator 95 that is an independent electric power source, through the power hub 93. Since the electric power accumulated in this electric power source 91 is supplied to electric equipment 94 and the electrically driven vehicle 96, in response to an instruction of the control part 90, the electric equipment 94 becomes workable, and at the same time, the electrically driven vehicle 96 becomes chargeable. That is, the electric power storage system is a system that enables accumulation and supply of the electric power in the house 89 using the electric power source 91.

The electric power accumulated in the electric power source 91 can be used, as requested. For this reason, for example, in the middle of the night when an electric bill is low, the electric power is accumulated in the electric power source 91 from the centralized electric power system 97, and in the daytime when an electric bill is high, the electric power accumulated in the electric power source 91 can be used.

In addition, the above-mentioned electric power storage system may be mounted in every house (household), or may be mounted in every plural houses (plural households).

Figure 10:
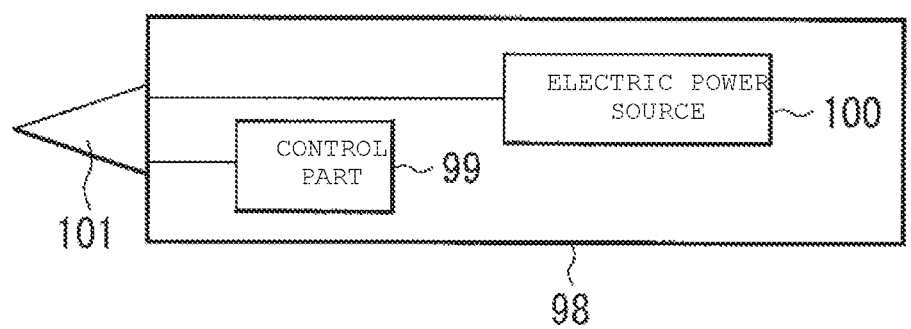
FIG. 10 is a block diagram representing constituent features of an application example of a secondary battery (electric tool) according to an embodiment of the present technology.

FIG. 10 represents a block configuration of an electric tool.

An electric tool illustrated herein is, for example, an electric drill. This electric tool is provided with, for example, a control part 99 and an electric power source 100 in the interior of a tool body 98. For example, a drill part 101 that is a movable part is workably (rotatably) attached to this tool body 98.

The tool body 98 contains, for example, a plastic material. The control part 99 controls operation (including the use state of the electric power source 100) of a whole electric tool. This control part 99 comprises, for example, CPU. The electric power source 100 comprises one or two or more secondary batteries of the present technology. This control part 99 supplies the electric power from the electric power source 100 to the drill part 101, in response to operation of an operating switch.

Examples of the present technology will be illustrated.

Experimental Examples 1-1 to 1-17

By the flowing procedure, using a sulfonyl compound (first sulfonyl compound), a laminate film type lithium ion secondary battery shown in FIG. 3 and FIG. 4 was manufactured.

When a positive electrode 33 was manufactured, first, by mixing lithium carbonate ($Li_2CO_3$) and cobalt carbonate ($CoCO_3$), and firing the mixture in the air (firing temperature=900° C., firing time=5 hours), lithium cobaltate ($LiCoO_2$) that is a lithium-containing compound was obtained. In this case, the mixing ratio (molar ratio) of lithium carbonate and cobalt carbonate was lithium carbonate:cobalt carbonate=0.5:1.

Subsequently, by mixing 91 parts by mass of a positive electrode active material (lithium cobaltate), 3 parts by mass of a positive electrode binding agent (polyvinylidene fluoride) and 6 parts by mass of a positive electrode conducting agent (graphite), a positive electrode mixture was obtained. Subsequently, by placing the positive electrode mixture in an organic solvent (N-methyl-2-pyrrolidone), and stirring the organic solvent, pasty positive electrode mixture slurry was obtained. Subsequently, by coating the positive electrode mixture slurry on both sides of a positive electrode current collector 33A (belt-like aluminum foil having the thickness of 12 μm) using a coating device, and drying the positive electrode mixture slurry, a positive electrode active material layer 33B was formed. Finally, the positive electrode active material layer 33B was compression-molded using a roll press machine.

When a negative electrode 34 was manufactured, first, by mixing 96 parts by mass of a negative electrode active material (graphite, median diameter=15 μm), 1.5 parts by mass of a negative electrode binding agent (acryl-modified styrene butadiene rubber copolymer), and 1.5 parts by mass of a thickener (carboxymethylcellulose), a negative electrode mixture was obtained. Subsequently, by placing the negative electrode mixture in pure water, and stirring the pure water, pasty negative electrode mixture slurry was obtained. Subsequently, by coating the negative electrode mixture slurry on both sides of a negative electrode current collector 34A (belt-like copper foil having the thickness of 15 μm) using a coating device, and drying the negative electrode mixture slurry, a negative electrode active material layer 34B was formed. Finally, the negative electrode active material layer 34B was compression-molded using a roll press machine.

When an electrolytic solution was prepared, by adding an electrolyte salt ($LiPF_6$) to a solvent (ethylene carbonate and propylene carbonate), thereby, stirring the solvent, and further adding a first sulfonyl compound to the solvent, the solvent was stirred. In this case, the mixing ratio (weight ratio) of ethylene carbonate and propylene carbonate was ethylene carbonate:propylene carbonate=50:50. The content of the electrolyte salt was 1.2 mol/kg based on the solvent. A kind of the first sulfonyl compound and the content (% by weight) of the first sulfonyl compound in the electrolytic solution are as shown in Table 1.

In addition, for comparison, according to the same procedure except that the first sulfonyl compound was not used, an electrolytic solution was prepared. Furthermore, for comparison, according to the same procedure except that another compound was used in place of the first sulfonyl compound, an electrolytic solution was prepared. A kind of another compound and the content (% by weight) of another compound in the electrolytic solution are as shown in Table 1.

When a secondary battery was assembled, first, a positive electrode lead 31 made of aluminum was welded to the positive electrode current collector 33A, and at the same time, a negative electrode lead 32 made of copper was welded to the negative electrode current collector 34A. Subsequently, by laminating the positive electrode 33 and the negative electrode 34 with a separator 35 (fine porous polyethylene film having the thickness of 12 μm) interposed therebetween, a laminate was obtained. Subsequently, by winding the laminate in a longitudinal direction, and sticking a protective tape 37 to an outermost circumferential part of the laminate, a wound electrode body 30 was manufactured. Finally, an exterior member 40 was folded so as to hold the wound electrode body 30, and external circumferential edges of three sides of the exterior member 40 were thermally fused. This exterior member 40 is an aluminum laminate film in which a nylon film having the thickness of 25 μm, an aluminum foil having the thickness of 40 μm, and a polypropylene film having the thickness of 30 μm are laminated from an outer side in this order. In this case, a close contact film 41 was inserted between the positive electrode lead 31 and the exterior member 40, and at the same time, a close contact film 41 was inserted between the negative electrode lead 32 and the exterior member 40. Finally, by injecting the electrolytic solution into the interior of the exterior member 40, the electrolytic solution was impregnated into the separator 35, and thereafter, external circumferential edges of remaining one side of the exterior member 40 were thermally fused in the reduced pressure environment. Thereby, since the wound electrode body 30 was enclosed into the interior of the exterior member 40, a laminate film type lithium ion secondary battery was completed.

In order to assess the battery property of the secondary battery, when the cycle property, the preservation property and the swelling property of the secondary battery were investigated, the result shown in Table 1 was obtained.

When the cycle property was investigated, first, by charging and discharging (2 cycles) the secondary battery in the normal temperature environment (temperature=23° C.), the discharge capacity of a second cycle was measured. Subsequently, by charging and discharging (100 cycles) the secondary battery in the low temperature environment (temperature=0° C.), the discharge capacity of a 102nd cycle was measured. Finally, low temperature cycle maintenance rate (%)=(discharge capacity of 102nd cycle/discharge capacity of second cycle)×100 was calculated.

In addition, at charging, constant current charging was performed until the voltage reached 4.2 V at the current of 0.2 C, and thereafter, constant voltage charging was performed until the current reached 0.05 C at the voltage of 4.2 V. At discharging, constant current discharging was performed until the voltage reached 2.5 V at the current of 0.2 C. "0.2 C" is a current value by which the battery capacity (theoretical capacity) can be discharged in 5 hours, and "0.05 C" is a current value by which the battery capacity can be discharged in 20 hours.

When the preservation property was investigated, first, by charging and discharging (2 cycles) the secondary battery in the normal temperature environment (temperature=23° C.), the discharge capacity of a second cycle (discharge capacity before preservation) was measured. Subsequently, after the secondary battery was charged again, the secondary battery in the charged state was preserved (preservation time=10 days) in the high temperature environment (temperature=60° C.) in a thermostatic bath. Subsequently, by taking out the secondary battery from the thermostatic bath, and discharging the secondary battery in the normal temperature environment (temperature=23° C.), the discharge capacity at a third cycle (discharge capacity after preservation) was measured. Finally, high temperature preservation maintenance rate (%)=(discharge capacity after preservation/discharge capacity before preservation)×100 was calculated. In addition, the charging and discharging conditions when the preservation property was investigated were the same as the charging and discharging conditions when the cycle property was investigated.

When the swelling property was investigated, first, in the normal temperature environment (temperature=23° C.), the secondary battery was charged and discharged (2 cycles). Subsequently, by immersing the secondary battery in an ethanol bath, the volume (volume (cm$^3$) before preservation) of the secondary battery was measured. Subsequently, after the secondary battery was taken out from the ethanol bath, the secondary battery was sufficiently dried. Subsequently, after the secondary battery was charged again, the secondary battery in the charged state was preserved (preservation time=10 days) in the high temperature environment (temperature=60° C.) in the thermostatic bath. Subsequently, after the secondary battery was taken out from the thermostatic bath, by immersing the secondary battery in the ethanol bath again, the volume (volume after preservation) of the secondary battery was measured. Finally, high temperature volume change rate (%)=(volume after preservation/volume before preservation)×100 was calculated. This high temperature volume change rate is a so-called swelling rate of the secondary battery. In addition, the charging and discharging conditions when the swelling property was investigated were the same as the charging and discharging conditions when the cycle property was investigated.

TABLE 1

| Experimental Example | Sulfonyl compound (First sulfonyl compound) | | Another compound | | Low temperature cycle maintenance rate (%) | High temperature preservation maintenance rate (%) | High temperature volume change rate (%) |
| --- | --- | --- | --- | --- | --- | --- | --- |
| | Kind | Content (% by weight) | Kind | Content (% by weight) | | | |
| 1-1 | Formula (1-2) | 0.1 | — | — | 70 | 75 | 135 |
| 1-2 | | 0.5 | — | — | 72 | 75 | 109 |
| 1-3 | | 1 | — | — | 75 | 80 | 110 |
| 1-4 | | 3 | — | — | 72 | 75 | 115 |
| 1-5 | | 5 | — | — | 71 | 75 | 120 |
| 1-6 | Formula (1-3) | 1 | — | — | 74 | 77 | 111 |
| 1-7 | Formula (1-4) | 1 | — | — | 74 | 76 | 115 |
| 1-8 | Formula (1-5) | 1 | — | — | 73 | 76 | 120 |
| 1-9 | Formula (1-6) | 1 | — | — | 73 | 75 | 118 |
| 1-10 | Formula (1-7) | 1 | — | — | 74 | 75 | 112 |
| 1-11 | Formula (1-8) | 1 | — | — | 71 | 76 | 115 |
| 1-12 | Formula (1-9) | 1 | — | — | 70 | 75 | 113 |
| 1-13 | Formula (1-10) | 1 | — | — | 72 | 75 | 125 |
| 1-14 | Formula (1-11) | 1 | — | — | 74 | 76 | 114 |
| 1-15 | Formula (1-12) | 1 | — | — | 72 | 75 | 121 |
| 1-16 | — | — | — | — | 69 | 74 | 151 |
| 1-17 | — | — | Formula (23-1) | 1 | 69 | 73 | 152 |

When the first sulfonyl compound was used (Experimental Examples 1-1 to 1-15), all of a low temperature cycle maintenance rate, a high temperature preservation maintenance rate and a high temperature volume change rate were improved, as compared with the case where the first sulfonyl compound was not used (Experimental Examples 1-16, 1-17).

In detail, when neither the first sulfonyl compound nor another compound was used (Experimental Example 1-16), a certain degree of a low temperature cycle maintenance rate and a high temperature preservation maintenance rate were obtained, but a high temperature volume change rate was excessively increased. In the following illustration, each of a low temperature cycle maintenance rate, a high temperature preservation maintenance rate and a high temperature volume change rate in the case where neither the first sulfonyl compound nor another compound was used (Experimental Example 1-16) will be used as a comparison criterion.

When another compound was used (Experimental Example 1-17), an equivalent low temperature cycle maintenance rate was obtained, but a high temperature preservation maintenance rate was decreased, and at the same time, a high temperature volume change rate was increased.

In contrast, when the first sulfonyl compound was used (Experimental Examples 1-1 to 1-15), both a low temperature cycle maintenance rate and a high temperature preservation maintenance rate were increased, and at the same time, a high temperature volume change rate was considerably decreased, not depending on a kind of the first sulfonyl compound. In this case, particularly, when the content of the first sulfonyl compound in the electrolytic solution was 0.1% by weight to 5% by weight, a high temperature volume change rate was sufficiently decreased, while increasing a low temperature cycle maintenance rate and a high temperature preservation maintenance rate.

Experimental Examples 2-1 to 2-16

As shown in Table 2, according to the same procedure as the above-mentioned procedure of Experimental Examples 1-1 to 1-17 except that a second sulfonyl compound was used in place of the first sulfonyl compound, secondary batteries were manufactured, and the cycle property, the preservation property and the swelling property of the secondary batteries were investigated. A kind of the second sulfonyl compound and the content (% by weight) of the second sulfonyl compound in the electrolytic solution are as shown in Table 2.

TABLE 2

| Experimental Example | Sulfonyl compound (Second sulfonyl compound) | | Another compound | | Low temperature cycle maintenance rate (%) | High temperature preservation maintenance rate (%) | High temperature volume change rate (%) |
|---|---|---|---|---|---|---|---|
| | Kind | Content (% by weight) | Kind | Content (% by weight) | | | |
| 2-1 | Formula (2-1) | 1 | — | — | 71 | 76 | 118 |
| 2-2 | Formula (2-13) | 0.1 | — | — | 70 | 75 | 136 |
| 2-3 | | 0.5 | — | — | 72 | 75 | 120 |
| 2-4 | | 1 | — | — | 74 | 77 | 113 |
| 2-5 | | 3 | — | — | 72 | 76 | 123 |
| 2-6 | | 5 | — | — | 70 | 74 | 140 |
| 2-7 | Formula (2-14) | 1 | — | — | 73 | 78 | 114 |
| 2-8 | Formula (2-15) | 1 | — | — | 74 | 75 | 116 |
| 2-9 | Formula (2-16) | 1 | — | — | 72 | 75 | 125 |
| 2-10 | Formula (2-17) | 1 | — | — | 72 | 75 | 119 |
| 2-11 | Formula (2-18) | 1 | — | — | 73 | 76 | 114 |
| 2-12 | Formula (2-19) | 1 | — | — | 72 | 76 | 118 |
| 2-13 | Formula (2-20) | 1 | — | — | 70 | 75 | 119 |
| 2-14 | Formula (2-21) | 1 | — | — | 72 | 77 | 125 |
| 2-15 | Formula (2-22) | 1 | — | — | 74 | 77 | 114 |
| 2-16 | Formula (2-23) | 1 | — | — | 72 | 76 | 130 |
| 1-16 | — | — | — | — | 69 | 74 | 151 |
| 1-17 | — | — | Formula (23-1) | 1 | 69 | 73 | 152 |

Also when the second sulfonyl compound was used (Table 2), the same result as that of when the first sulfonyl compound was used (Table 1) was obtained. That is, when the second sulfonyl compound was used (Experimental Examples 2-1 to 2-16), all of a low temperature cycle maintenance rate, a high temperature preservation maintenance rate and a high temperature volume change rate were improved, as compared with the case where the second sulfonyl compound was not used (Experimental Examples 1-16, 1-17).

Experimental Examples 3-1 to 3-16

As shown in Table 3, according to the same procedure as that of the Experimental Examples 1-1 to 1-17 except that a third sulfonyl compound was used in place of the first sulfonyl compound, secondary batteries were manufactured, and the cycle property, the preservation property and the swelling property of the secondary batteries were investigated. A kind of the third sulfonyl compound and the content (% by weight) of the third sulfonyl compound in the electrolytic solution are as shown in Table 3.

TABLE 3

| Experimental Example | Sulfonyl compound (Third sulfonyl compound) Kind | Content (% by weight) | Another compound Kind | Content (% by weight) | Low temperature cycle maintenance rate (%) | High temperature preservation maintenance rate (%) | High temperature volume change rate (%) |
|---|---|---|---|---|---|---|---|
| 3-1 | Formula (3-1) | 1 | — | — | 72 | 76 | 118 |
| 3-2 | Formula (3-13) | 0.1 | — | — | 70 | 75 | 136 |
| 3-3 |  | 0.5 | — | — | 71 | 76 | 121 |
| 3-4 |  | 1 | — | — | 74 | 78 | 115 |
| 3-5 |  | 3 | — | — | 71 | 75 | 126 |
| 3-6 |  | 5 | — | — | 70 | 75 | 145 |
| 3-7 | Formula (3-14) | 1 | — | — | 72 | 78 | 116 |
| 3-8 | Formula (3-15) | 1 | — | — | 73 | 75 | 118 |
| 3-9 | Formula (3-16) | 1 | — | — | 73 | 75 | 120 |
| 3-10 | Formula (3-17) | 1 | — | — | 72 | 75 | 126 |
| 3-11 | Formula (3-18) | 1 | — | — | 73 | 75 | 123 |
| 3-12 | Formula (3-19) | 1 | — | — | 73 | 75 | 126 |
| 3-13 | Formula (3-20) | 1 | — | — | 70 | 77 | 128 |
| 3-14 | Formula (3-21) | 1 | — | — | 72 | 76 | 125 |
| 3-15 | Formula (3-22) | 1 | — | — | 73 | 77 | 119 |
| 3-16 | Formula (3-23) | 1 | — | — | 72 | 76 | 131 |
| 1-16 | — | — | — | — | 69 | 74 | 151 |
| 1-17 | — | — | Formula (23-1) | 1 | 69 | 73 | 152 |

Also when the third sulfonyl compound was used (Table 3), the same result as that of the case where the first sulfonyl compound was used (Table 1) was obtained. That is, when the third sulfonyl compound was used (Experimental Examples 3-1 to 3-16), all of a low temperature cycle maintenance rate, a high temperature preservation maintenance rate and a high temperature volume change rate were improved, as compared with the case where the third sulfonyl compound was not used (Experimental Examples 1-16, 1-17).

Experimental Examples 4-1 to 4-6

As shown in Table 4, according to the same procedure as that of the Experimental Examples 1-3, 2-4, 3-4 except that an additive (dinitrile compound) was contained in the electrolytic solution, secondary batteries were manufactured, and the cycle property, the preservation property and the swelling property of the secondary batteries were investigated. In this case, succinonitrile and adiponitrile were used as the dinitrile compound, and the content of the dinitrile compound in the electrolytic solution was 0.5% by weight.

In addition, for comparison, the sulfonyl compound was not contained in the electrolytic solution by containing only the dinitrile compound in the electrolytic solution.

TABLE 4

| Experimental Example | Sulfonyl compound Kind | Content (% by weight) | Dinitrile compound Kind | Content (% by weight) | Low temperature cycle maintenance rate (%) | High temperature preservation maintenance rate (%) | High temperature volume change rate (%) |
|---|---|---|---|---|---|---|---|
| 4-1 | Formula (1-2) | 1 | Succinonitrile | 0.5 | 77 | 82 | 105 |
| 4-2 | Formula (2-13) | 1 | Succinonitrile | 0.5 | 76 | 79 | 108 |
| 4-3 | Formula (3-13) | 1 | Succinonitrile | 0.5 | 76 | 80 | 110 |
| 4-4 | Formula (1-2) | 1 | Adiponitrile | 0.5 | 76 | 82 | 104 |
| 1-3 | Formula (1-2) | 1 | — | — | 75 | 80 | 110 |
| 2-4 | Formula (2-13) | 1 | — | — | 74 | 77 | 113 |
| 3-4 | Formula (3-13) | 1 | — | — | 74 | 78 | 115 |
| 4-5 | — | — | Succinonitrile | 0.5 | 55 | 73 | 135 |
| 4-6 | — | — | Adiponitrile | 0.5 | 59 | 73 | 134 |
| 1-16 | — | — | — | — | 69 | 74 | 151 |

When the electrolytic solution contained the sulfonyl compound together with the nitrile compound (Experimental Examples 4-1 to 4-3), each of a low temperature cycle maintenance rate and a high temperature preservation maintenance rate was more increased, and a high temperature volume change rate was more decreased, as compared with the case where the electrolytic solution contained only the sulfonyl compound (Experimental Examples 1-3, 2-4, 3-4). In particular, when the electrolytic solution contained the dinitrile compound together with the sulfonyl compound (Experimental Examples 4-1, 4-4), an equivalent low temperature cycle maintenance rate, an equivalent high temperature preservation maintenance rate and an equivalent high temperature volume change rate were obtained, not depending on a kind of the dinitrile compound.

Furthermore, when the electrolytic solution contained the dinitrile compound (Experimental Examples 4-5, 4-6), a high temperature volume change rate was decreased, while each of a low temperature cycle maintenance rate and a high temperature preservation maintenance rate was decreased, as compared with the case where the electrolytic solution contained neither the sulfonyl compound nor the dinitrile compound (Experimental Example 1-16). However, when the electrolytic solution contained the dinitrile compound together with the sulfonyl compound (Experimental Examples 4-1 to 4-3), each of a low temperature cycle maintenance rate and a high temperature preservation maintenance rate was increased, and moreover, a high temperature volume change rate was more decreased, due to the synergistic action of the sulfonyl compound and the dinitrile compound, as compared with the case where the electrolytic solution contained neither the sulfonyl compound nor the dinitrile compound (Experimental Example 1-16).

From the results shown in Table 1 to Table 4, when the electrolytic solution contained the sulfonyl compound, all of the cycle property, the preservation property and the swelling property were improved. Accordingly, the excellent battery property was obtained in the secondary battery.

Hereinabove, the present technology has been illustrated while enumerating one embodiment and Examples, but the present technology is not limited to modes illustrated in one embodiment and Examples, and a variety of modifications are possible.

Specifically, the case where a battery structure of the secondary battery is the cylindrical type and the laminate film type has been illustrated, but a battery structure of the secondary battery of the present technology is not particularly limited. Specifically, a battery structure of the secondary battery may be another battery structure such as, for example, a square type and a coin type.

Furthermore, the case where the battery element has a winding structure has been illustrated, but a structure possessed by the battery element in the secondary battery of the present technology is not particularly limited. Specifically, the battery element may have, for example, another structure such as a laminate structure.

Furthermore, the secondary battery in which the capacity of the negative electrode is obtained by occlusion and release of lithium is obtained (lithium ion secondary battery) and the secondary battery in which the capacity of the negative electrode is obtained by precipitation and dissolution of lithium (lithium metal secondary battery) have been illustrated, but the principle of that the capacity of the negative electrode is obtained in the secondary battery of the present technology is not particularly limited. Specifically, for example, by making the capacity of the negative electrode material that can occlude and release lithium smaller than the capacity of the positive electrode, the secondary battery may be a secondary battery in which the capacity of the negative electrode is obtained by the sum of the capacity due to occlusion and release of lithium and the capacity due to precipitation and dissolution of lithium.

Furthermore, the case where lithium is used as the electrode reactant has been illustrated, but the electrode reactant is not limited to this. The electrode reactant may be, for example, another group 1 element in the long-form periodic table, such as sodium (Na) and potassium (K), may be a group 2 element in the long-form periodic table, such as magnesium (Mg) and calcium (Ca), or may be another light metal such as aluminum (Al). Furthermore, the electrode reactant may be an alloy containing any one or two or more kinds of the above-mentioned series of elements.

In addition, the effect described in the present description is just an example, and is not limited, and there may be another effect.

In addition, the present technology can also take the following constituent features.

(1) A secondary battery comprising:
a positive electrode,
a negative electrode, and
an electrolytic solution comprising at least one kind of sulfonyl compounds that are represented by each of the following formula (1), formula (2) and formula (3).

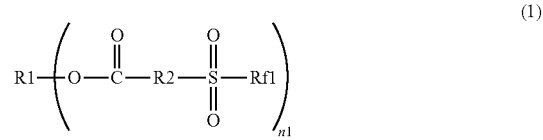

(R1 is any of an n1-valent hydrocarbon group, an n1-valent oxygen-containing hydrocarbon group, an n1-valent halogenated hydrocarbon group and an n1-valent halogenated oxygen-containing hydrocarbon group. R2 is any of a divalent hydrocarbon group and a divalent halogenated hydrocarbon group. Rf1 is any of a halogen group and a monovalent halogenated hydrocarbon group. n1 is an integer of 2 or more.)

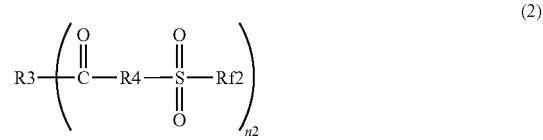

(R3 is any of an n2-valent hydrocarbon group, an n2-valent oxygen-containing hydrocarbon group, an n2-valent halogenated hydrocarbon group and an n2-valent halogenated oxygen-containing hydrocarbon group. R4 is any of a divalent hydrocarbon group and a divalent halogenated hydrocarbon group. Rf2 is any of a halogen group and a monovalent halogenated hydrocarbon group. n2 is an integer of 1 or more.

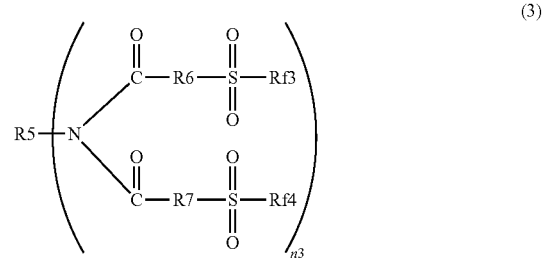

(R5 is any of an n3-valent hydrocarbon group, an n3-valent oxygen-containing hydrocarbon group, an n3-valent halogenated hydrocarbon group and an n3-valent halogenated oxygen-containing hydrocarbon group. Each of R6 and R7 is any of a divalent hydrocarbon group and a divalent halogenated hydrocarbon group. Each of Rf3 and Rf4 is any of a halogen group and a monovalent halogenated hydrocarbon group. n3 is an integer of 1 or more.)

(2) The secondary battery according to (1), wherein the n1-valent hydrocarbon group is a group in which n1 hydrogen groups are eliminated from a hydrocarbon, and the hydrocarbon is any of an alkane, an alkene, an alkyne, an alicyclic hydrocarbon, an aromatic hydrocarbon and a compound in which two or more kinds of them are mutually bound, the n1-valent oxygen-containing hydrocarbon group is a group in which one or two or more ether bonds (—O—) are introduced into the middle of the n1-valent hydrocarbon group, the n1-valent halogenated hydrocarbon group is a group in which at least one hydrogen group (—H) of the n1-valent hydrocarbon group is substituted with a halogen group, the n1-valent halogenated oxygen-containing hydrocarbon group is a group in which at least one hydrogen group of the n1-valent oxygen-containing hydrocarbon group is substituted with a halogen group, and the halogen group is at least one kind of a fluorine group (—F), a chlorine group (—Cl), a bromine group (—Br) and an iodine group (—I).

(3) The secondary battery according to (1) or (2), wherein the n2-valent hydrocarbon group is a group in which n2 hydrogen groups are eliminated from a hydrocarbon, and the hydrocarbon is any of an alkane, an alkene, an alkyne, an alicyclic hydrocarbon, an aromatic hydrocarbon and a compound in which two or more kinds of them are mutually bound, the n2-valent oxygen-containing hydrocarbon group is a group in which one or two or more ether bonds are introduced into the middle of the n2-valent hydrocarbon group, the n2-valent halogenated hydrocarbon group is a group in which at least one hydrogen group of the n2-valent hydrocarbon group is substituted with a halogen group, the n2-valent halogenated oxygen-containing hydrocarbon group is a group in which at least one hydrogen group of the n2-valent oxygen-containing hydrocarbon group is substituted with a halogen group, and the halogen group is at least one kind of a fluorine group, a chlorine group, a bromine group and an iodine group.

(4) The secondary battery according to any one of (1) to (3), wherein the n3-valent hydrocarbon group is a group in which n3 hydrogen groups are eliminated from a hydrocarbon, and the hydrocarbon is any of an alkane, an alkene, an alkyne, an alicyclic hydrocarbon, an aromatic hydrocarbon and a compound in which two or more kinds of them are mutually bound, the n3-valent oxygen-containing hydrocarbon group is a group in which one or two or more ether bonds are introduced into the middle of the n3-valent hydrocarbon group, the n3-valent halogenated hydrocarbon group is a group in which at least one hydrogen group of the n3-valent hydrocarbon group is substituted with a halogen group, the n3-valent halogenated oxygen-containing hydrocarbon group is a group in which at least one hydrogen group of the n3-valent oxygen-containing hydrocarbon group is substituted with a halogen group, and the halogen group is at least one kind of a fluorine group, a chlorine group, a bromine group and an iodine group.

(5) The secondary battery according to any one of (1) to (4), wherein the divalent hydrocarbon group is any of an alkylene group, an alkenylene group, an alkynylene group, a cycloalkylene group, an arylene group and a divalent group in which two or more kinds of them are mutually bound, the divalent halogenated hydrocarbon group is a group in which at least one hydrogen group of the divalent hydrocarbon group is substituted with a halogen group, and the halogen group is at least one kind of a fluorine group, a chlorine group, a bromine group and an iodine group.

(6) The secondary battery according to any one of (1) to (5), wherein the halogen group is at least one kind of a fluorine group, a chlorine group, a bromine group and an iodine group, the monovalent halogenated hydrocarbon group is a group in which at least one hydrogen group of a monovalent hydrocarbon group is substituted with the halogen group, and the monovalent hydrocarbon group is any of an alkyl group, an alkenyl group, an alkynyl group, a cycloalkyl group, an aryl group and a monovalent group in which two or more kinds of them are mutually bound.

(7) The secondary battery according to any one of (1) to (6), wherein the n1-valent hydrocarbon group is a group in which n1 hydrogen groups are eliminated from any of an alkane, an alkene and an alkyne, the n2-valent hydrocarbon group is a group in which n2 hydrogen groups are eliminated from any of an alkane, an alkene and an alkyne, the n3-valent hydrocarbon group is a group in which n3 hydrogen groups are eliminated from any of an alkane, an alkene and an alkyne, and the carbon number of any of the n1-valent hydrocarbon group, the n2-valent hydrocarbon group and the n3-valent hydrocarbon group is 1 or more and 12 or less.

(8) The secondary battery according to any one of (1) to (7), wherein the n2-valent hydrocarbon group is any of an alkylene group, an alkenylene group and an alkynylene group, the n2-valent halogenated hydrocarbon group is any of groups in which at least one hydrogen group of each of an alkylene group, an alkenylene group and an alkynylene group is substituted with a halogen group, and the carbon number of each of the divalent hydrocarbon group and the divalent halogenated hydrocarbon group is 1 or more and 4 or less.

(9) The secondary battery according to any one of (1) to (8), wherein the carbon number of the monovalent halogenated hydrocarbon group is 1 or more and 4 or less.

(10) The secondary battery according to any one of (1) to (9), wherein the monovalent halogenated hydrocarbon group is a perfluoroalkyl group.

(11) The secondary battery according to any one of (1) to (10), wherein the n1 is 4 or less, the n2 is 4 or less, and the n3 is 4 or less.

(12) The secondary battery according to any one of (1) to (11), wherein the n2 is 2 or more, and the n3 is 2 or more.

(13) The secondary battery according to any one of (1) to (12), wherein the sulfonyl compound shown in the formula (1) includes at least one of compounds that are represented by each of the following formula (4) and formula (5), the sulfonyl compound shown in the formula (2) includes at least one of compounds that are represented by each of the following formula (6) and formula (7), and the sulfonyl compound shown in the formula (3) includes at least one of compounds that are represented by each of the following formula (8) and formula (9).

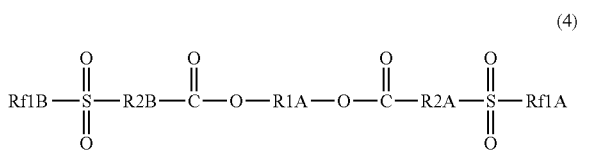

(4)

(R1A is any of a divalent hydrocarbon group, a divalent oxygen-containing hydrocarbon group, a divalent halogenated hydrocarbon group and a divalent halogenated oxygen-containing hydrocarbon group. Each of R2A and R2B is any of a divalent hydrocarbon group and a divalent halogenated hydrocarbon group. Each of Rf1A and Rf1B is any of a halogen group and a monovalent halogenated hydrocarbon group.)

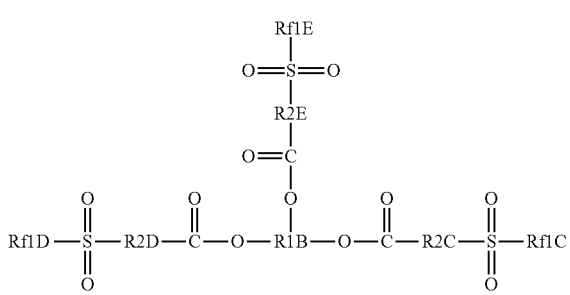

(5)

(R1B is any of a trivalent hydrocarbon group, a trivalent oxygen-containing hydrocarbon group, a trivalent halogenated hydrocarbon group and a trivalent halogenated oxygen-containing hydrocarbon group. Each of R2C, R2D and R2E is any of a divalent hydrocarbon group and a divalent halogenated hydrocarbon group. Each of Rf1C, Rf1D and Rf1E is any of a halogen group and a monovalent halogenated hydrocarbon group.)

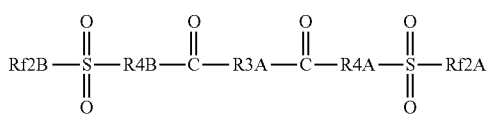

(6)

(R3A is any of a divalent hydrocarbon group, a divalent oxygen-containing hydrocarbon group, a divalent halogenated hydrocarbon group and a divalent halogenated oxygen-containing hydrocarbon group. Each of R4A and R4B is any of a divalent hydrocarbon group and a divalent halogenated hydrocarbon group. Each of Rf2A and Rf2B is any of a halogen group and a monovalent halogenated hydrocarbon group.)

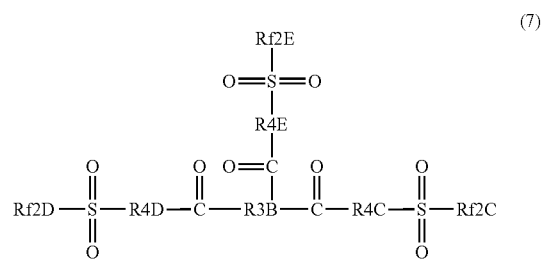

(7)

(R3B is any of a trivalent hydrocarbon group, a trivalent oxygen-containing hydrocarbon group, a trivalent halogenated hydrocarbon group and a trivalent halogenated oxygen-containing hydrocarbon group. Each of R4C, R4D and R4E is any of a divalent hydrocarbon group and a divalent halogenated hydrocarbon group. Each of Rf2C, Rf2D and Rf2E is any of a halogen group and a monovalent halogenated hydrocarbon group.)

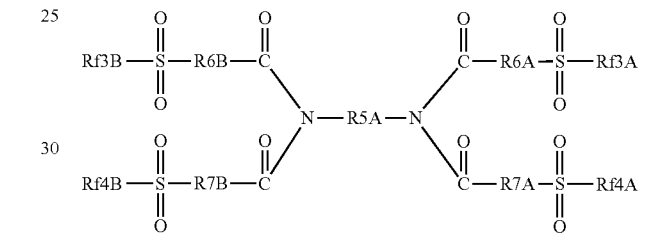

(8)

(R5A is any of a divalent hydrocarbon group, a divalent oxygen-containing hydrocarbon group, a divalent halogenated hydrocarbon group and a divalent halogenated oxygen-containing hydrocarbon group. Each of R6A, R6B, R7A and R7B is any of a divalent hydrocarbon group and a divalent halogenated hydrocarbon group. Each of Rf3A, Rf3B, Rf4A and Rf4B is any of a halogen group and a monovalent halogenated hydrocarbon group.)

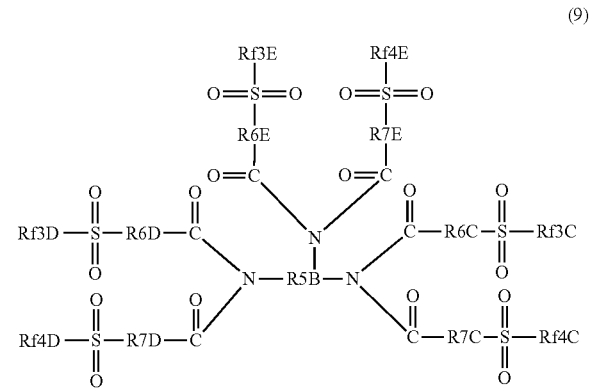

(9)

(R5B is any of a trivalent hydrocarbon group, a trivalent oxygen-containing hydrocarbon group, a trivalent halogenated hydrocarbon group and a trivalent halogenated oxygen-containing hydrocarbon group. Each of R6C, R6D, R6E, R7C, R7D and R7E is any of a divalent hydrocarbon group and a divalent halogenated hydrocarbon group. Each of Rf3C, Rf3D, Rf3E, Rf4C, Rf4D and Rf4E is any of a halogen group and a monovalent halogenated hydrocarbon group.)

(14) The secondary battery according to any one of (1) to (13), wherein the electrolytic solution further comprises at least one kind of dinitrile compounds represented by the following formula (16).

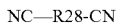

(R28 is any of a divalent hydrocarbon group, a divalent halogenated hydrocarbon group, a divalent oxygen-containing group, a divalent nitrogen-containing group, a divalent sulfur-containing group, a divalent phosphorus-containing group and a divalent group in which two or more kinds of them are bound.)

(15) The secondary battery according to any one of (1) to (14), wherein the content of the sulfonyl group in the electrolytic solution is 0.01% by weight or more and 5% by weight or less.

(16) The secondary battery according to any one of (1) to (15), wherein the secondary battery is a lithium ion secondary battery.

(17) An electrolytic solution for a secondary battery, comprising:
at least one kind of sulfonyl compounds that are represented by each of the following formula (1), formula (2) and formula (3).

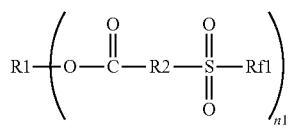

(R1 is any of an n1-valent hydrocarbon group, an n1-valent oxygen-containing hydrocarbon group, an n1-valent halogenated hydrocarbon group and an n1-valent halogenated oxygen-containing hydrocarbon group. R2 is any of a divalent hydrocarbon group and a divalent halogenated hydrocarbon group. Rf1 is any of a halogen group and a monovalent halogenated hydrocarbon group. n1 is an integer of 2 or more.)

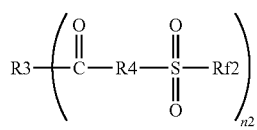

(R3 is any of an n2-valent hydrocarbon group, an n2-valent oxygen-containing hydrocarbon group, an n2-valent halogenated hydrocarbon group and an n2-valent halogenated oxygen-containing hydrocarbon group. R4 is any of a divalent hydrocarbon group and a divalent halogenated hydrocarbon group. Rf2 is any of a halogen group and a monovalent halogenated hydrocarbon group. n2 is an integer of 1 or more.

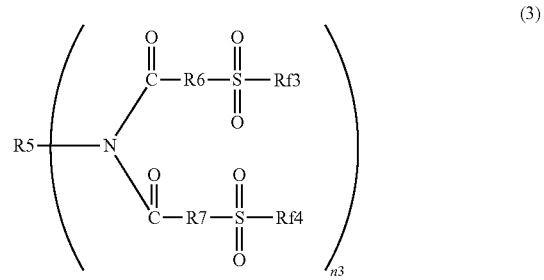

(R5 is any of an n3-valent hydrocarbon group, an n3-valent oxygen-containing hydrocarbon group, an n3-valent halogenated hydrocarbon group and an n3-valent halogenated oxygen-containing hydrocarbon group. Each of R6 and R7 is any of a divalent hydrocarbon group and a divalent halogenated hydrocarbon group. Each of Rf3 and Rf4 is any of a halogen group and a monovalent halogenated hydrocarbon group. n3 is an integer of 1 or more.)

(18) A battery pack comprising:
a secondary battery as defined in any one of (1) to (16),
a control part controlling operation of the secondary battery, and
a switch part switching operation of the secondary battery in response to an instruction of the control part.

(19) An electrically driven vehicle comprising:
a secondary battery as defined in any one of (1) to (16),
a conversion part converting the electric power supplied from the secondary battery into a driving force,
a driving part that performs driving depending on the driving force, and
a control part controlling operation of the secondary battery.

(20) An electric power storage system comprising:
a secondary battery as defined in any one of (1) to (16),
one or two or more pieces of electric equipment to which the electric power is supplied from the secondary battery, and
a control part controlling electric power supply to the electric equipment from the secondary battery.

(21) An electric tool comprising:
a secondary battery as defined in any one of (1) to (16), and
a movable part to which the electric power is supplied from the secondary battery.

(22) Electronic equipment comprising, as an electric power supply source, a secondary battery as defined in any one of (1) to (16).

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:
1. A secondary battery comprising:
a positive electrode,
a negative electrode, and
an electrolytic solution including at least one kind of sulfonyl compounds that are represented by chemical formula (1), chemical formula (2) and chemical formula (3):

[Chemical formula 1]

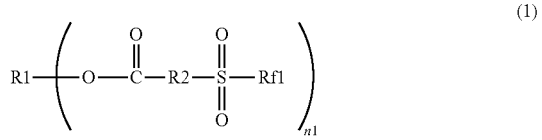
(1)

wherein R1 represents one of an n1-valent hydrocarbon group, an n1-valent oxygen-containing hydrocarbon group, an n1-valent halogenated hydrocarbon group and an n1-valent halogenated oxygen-containing hydrocarbon group, R2 represents one of a divalent hydrocarbon group and a divalent halogenated hydrocarbon group, Rf1 represents one of a halogen group and a monovalent halogenated hydrocarbon group, and n1 is an integer of 2 or more,

[Chemical formula 2]

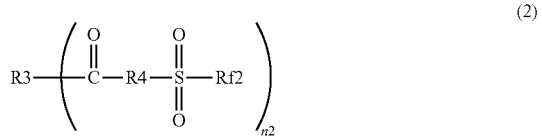
(2)

wherein R3 represents one of an n2-valent hydrocarbon group, an n2-valent oxygen-containing hydrocarbon group, an n2-valent halogenated hydrocarbon group and an n2-valent halogenated oxygen-containing hydrocarbon group, R4 represents one of a divalent hydrocarbon group and a divalent halogenated hydrocarbon group, Rf2 represents one of a halogen group and a monovalent halogenated hydrocarbon group, and n2 is an integer of 1 or more,

[Chemical formula 3]

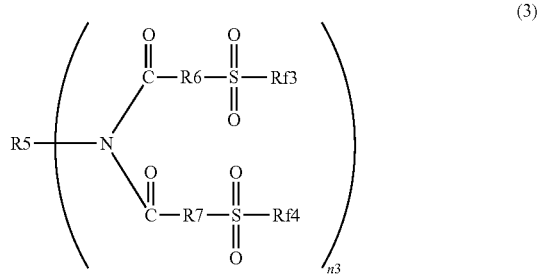
(3)

wherein R5 represents one of an n3-valent hydrocarbon group, an n3-valent oxygen-containing hydrocarbon group, an n3-valent halogenated hydrocarbon group and an n3-valent halogenated oxygen-containing hydrocarbon group, each of R6 and R7 represents one of a divalent hydrocarbon group and a divalent halogenated hydrocarbon group, each of Rf3 and Rf4 represents one of a halogen group and a monovalent halogenated hydrocarbon group, and n3 is an integer of 1 or more, and wherein the n2-valent hydrocarbon group includes a group in which n2 hydrogen groups are eliminated from a hydrocarbon, and the hydrocarbon is one of an alkane, an alkene, an alkyne, an alicyclic hydrocarbon, an aromatic hydrocarbon and combinations thereof, the n2-valent oxygen-containing hydrocarbon group includes a group in which one or two or more ether bounds are introduced into a middle of the n2-valent hydrocarbon group, the n2-valent halogenated hydrocarbon group includes a group in which at least one hydrogen group of the n2-valent hydrocarbon group is substituted with a halogen group, the n2-valent halogenated oxygen-containing hydrocarbon group includes a group in which at least one hydrogen group of the n2-valent oxygen-containing hydrocarbon group is substituted with a halogen group, and the halogen group includes at least one kind of a fluorine group, a chlorine group, a bromine group and an iodine group.

2. The secondary battery according to claim 1, wherein
the n1-valent hydrocarbon group includes a group in which n1 hydrogen groups are eliminated from a hydrocarbon, and the hydrocarbon is one of an alkane, an alkene, an alkyne, an alicyclic hydrocarbon, an aromatic hydrocarbon and combinations thereof, the n1-valent oxygen-containing hydrocarbon group includes a group in which one or two or more ether bounds (—O—) are introduced into a middle of the n1-valent hydrocarbon group, the n1-valent halogenated hydrocarbon group includes a group in which at least one hydrogen group (—H) of the n1-valent hydrocarbon group is substituted with a halogen group, the n1-valent halogenated oxygen-containing hydrocarbon group includes a group in which at least one hydrogen group of the n1-valent oxygen-containing hydrocarbon group is substituted with a halogen group, and the halogen group includes at least one kind of a fluorine group (—F), a chlorine group (—Cl), a bromine group (—Br) and an iodine group (—I).

3. The secondary battery according to claim 1, wherein
the n3-valent hydrocarbon group includes a group in which n3 hydrogen groups are eliminated from a hydrocarbon, and the hydrocarbon is one of an alkane, an alkene, an alkyne, an alicyclic hydrocarbon, an aromatic hydrocarbon and combinations thereof, the n3-valent oxygen-containing hydrocarbon group includes a group in which one or two or more ether bonds are introduced into a middle of the n3-valent hydrocarbon group, the n3-valent halogenated hydrocarbon group includes a group in which at least one hydrogen group of the n3-valent hydrocarbon group is substituted with a halogen group, the n3-valent halogenated oxygen-containing hydrocarbon group includes a group in which at least one hydrogen group of the n3-valent oxygen-containing hydrocarbon group is substituted with a halogen group, and the halogen group includes at least one kind of a fluorine group, a chlorine group, a bromine group and an iodine group.

4. The secondary battery according to claim 1, wherein
the divalent hydrocarbon group of Chemical formula 1, Chemical formula 2, and Chemical formula 3 includes one of an alkylene group, an alkenylene group, an alkynylene group, a cycloalkylene group, an arylene and a divalent group in which two or more kinds of them are mutually bound, the divalent halogenated hydrocarbon group of Chemical formula 1, Chemical formula 2, and Chemical formula 3 includes a group in which at least one hydrogen group of the divalent hydrocarbon group is substituted with a halogen group, and the halogen group of Chemical formula 1, Chemical formula 2, and Chemical formula 3 includes at least one kind of a fluorine group, a chlorine group, a bromine group and an iodine group.

5. The secondary battery according to claim 1, wherein the halogen group of Chemical formula 1, Chemical formula 2, and Chemical formula 3 includes at least one kind of a fluorine group, a chlorine group, a bromine group and an iodine group, the monovalent halogenated hydrocarbon group of Chemical formula 1, Chemical formula 2, and Chemical formula 3 includes a group in which at least one hydrogen group of a monovalent hydrocarbon group is substituted with the halogen group, and the monovalent hydrocarbon group includes one of an alkyl group, an alkenyl group, an alkynyl group, a cycloalkyl group, an aryl group and a monovalent group in which two or more kinds of them are mutually bound.

6. The secondary battery according to claim 1, wherein the n1-valent hydrocarbon group includes a group in which n1 hydrogen groups are eliminated from one of an alkane, an alkene and an alkyne, the n3-valent hydrocarbon group includes a group in which n3 hydrogen groups are eliminated from one of an alkane, an alkene and an alkyne, and a carbon number of each of the n1-valent hydrocarbon group, the n2-valent hydrocarbon group and the n3-valent hydrocarbon group is 1 or more and 12 or less.

7. The secondary battery according to claim 1, wherein the divalent hydrocarbon group of Chemical formula 1, Chemical formula 2, and Chemical formula 3 includes one of an alkylene group, an alkenylene group and an alkynylene group, the divalent halogenated hydrocarbon group of Chemical formula 1, Chemical formula 2, and Chemical formula 3 includes one of groups in which at least one hydrogen group of each of an alkylene group, an alkenylene group and alkynylene is substituted with a halogen group, and a carbon number of each of the divalent hydrocarbon group and the divalent halogenated hydrocarbon group is 1 or more and 4 or less.

8. The secondary battery according to claim 1, wherein a carbon number of the monovalent halogenated hydrocarbon group of Chemical formula 1, Chemical formula 2, and Chemical formula 3 is 1 or more and 4 or less.

9. The secondary battery according to claim 1, wherein the monovalent halogenated hydrocarbon group of Chemical formula 1, Chemical formula 2, and Chemical formula 3 includes a perfluoroalkyl group.

10. The secondary battery according to claim 1, wherein
the n1 is 4 or less,
the n2 is 4 or less, and
the n3 is 4 or less.

11. The secondary battery according to claim 1, wherein a content of the sulfonyl compound in the electrolytic solution is from 0.01% by weight to 5% by weight.

12. The secondary battery according to claim 1, wherein the secondary battery includes a lithium ion secondary battery.

13. A battery pack comprising:
the secondary battery according to claim 1,
a controller configured to control operation of the secondary battery, and
a switch configured to switch operation of the secondary battery in response to an instruction of the controller.

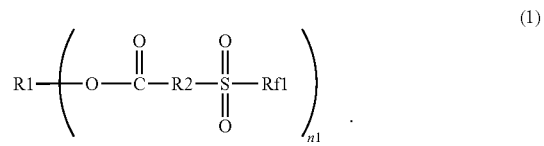

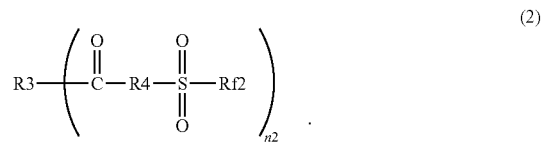

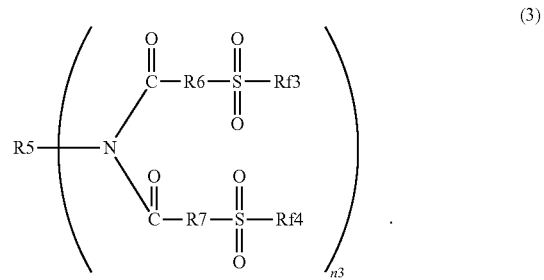

14. An electrically driven vehicle comprising:
the secondary battery according to claim 1,
a converter configured to convert an electric power supplied from the secondary battery into a driving force,
a driver configured to perform driving depending on the driving force, and
a controller configured to control operation of the secondary battery.

15. Electronic equipment comprising the secondary battery according to claim 1 as an electric power supply source.

16. A secondary battery comprising:
a positive electrode,
a negative electrode, and
an electrolytic solution including at least one kind of sulfonyl compounds that are represented by chemical formula (1), chemical formula (2) and chemical formula (3):

[Chemical formula 1]

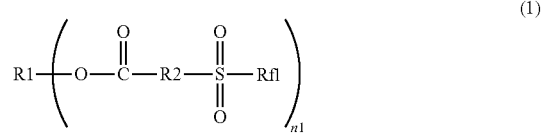

wherein R1 represents one of an n1-valent hydrocarbon group, an n1-valent oxygen-containing hydrocarbon group, an n1-valent halogenated hydrocarbon group and an n1-valent halogenated oxygen-containing hydrocarbon group, R2 represents one of a divalent hydrocarbon group and a divalent halogenated hydrocarbon group, Rf1 represents one of a halogen group and a monovalent halogenated hydrocarbon group, and n1 is an integer of 2 or more,

[Chemical formula 2]

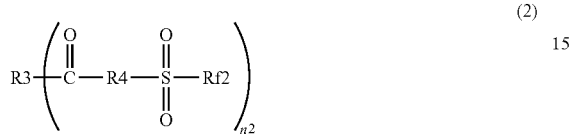

(2)

wherein R3 represents one of an n2-valent hydrocarbon group, an n2-valent oxygen-containing hydrocarbon group, an n2-valent halogenated hydrocarbon group and an n2-valent halogenated oxygen-containing hydrocarbon group, R4 represents one of a divalent hydrocarbon group and a divalent halogenated hydrocarbon group, Rf2 represents one of a halogen group and a monovalent halogenated hydrocarbon group, and n2 is an integer of 1 or more,

[Chemical formula 3]

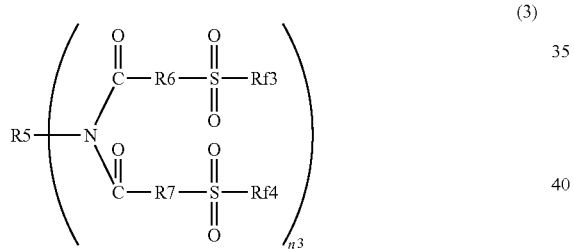

(3)

wherein R5 represents one of an n3-valent hydrocarbon group, an n3-valent oxygen-containing hydrocarbon group, an n3-valent halogenated hydrocarbon group and an n3-valent halogenated oxygen-containing hydrocarbon group, each of R6 and R7 represents one of a divalent hydrocarbon group and a divalent halogenated hydrocarbon group, each of Rf3 and Rf4 represents one of a halogen group and a monovalent halogenated hydrocarbon group, and n3 is an integer of 1 or more, and wherein the n2 is 2 or more, and the n3 is 2 or more.

17. A battery pack comprising:
the secondary battery according to claim 16,
a controller configured to control operation of the secondary battery, and
a switch configured to switch operation of the secondary battery in response to an instruction of the controller.

18. An electrically driven vehicle comprising:
the secondary battery according to claim 16,
a converter configured to convert an electric power supplied from the secondary battery into a driving force,
a driver configured to perform driving depending on the driving force, and a controller configured to control operation of the secondary battery.

19. Electronic equipment comprising the secondary battery according to claim 16 as an electric power supply source.

20. A secondary battery comprising:
a positive electrode,
a negative electrode, and
an electrolytic solution including at least one kind of sulfonyl compounds that are represented by chemical formula (1), chemical formula (2) and chemical formula (3):

[Chemical formula 1]

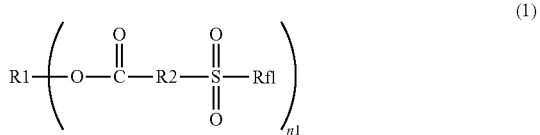

(1)

wherein R1 represents one of an n1-valent hydrocarbon group, an n1-valent oxygen-containing hydrocarbon group, an n1-valent halogenated hydrocarbon group and an n1-valent halogenated oxygen-containing hydrocarbon group, R2 represents one of a divalent hydrocarbon group and a divalent halogenated hydrocarbon group, Rf1 represents one of a halogen group and a monovalent halogenated hydrocarbon group, and n1 is an integer of 2 or more,

[Chemical formula 2]

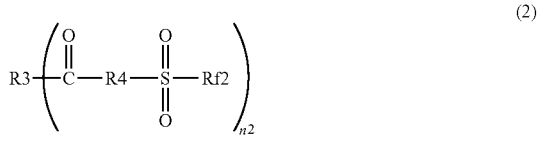

(2)

wherein R3 represents one of an n2-valent hydrocarbon group, an n2-valent oxygen-containing hydrocarbon group, an n2-valent halogenated hydrocarbon group and an n2-valent halogenated oxygen-containing hydrocarbon group, R4 represents one of a divalent hydrocarbon group and a divalent halogenated hydrocarbon group, Rf2 represents one of a halogen group and a monovalent halogenated hydrocarbon group, and n2 is an integer of 1 or more,

[Chemical formula 3]

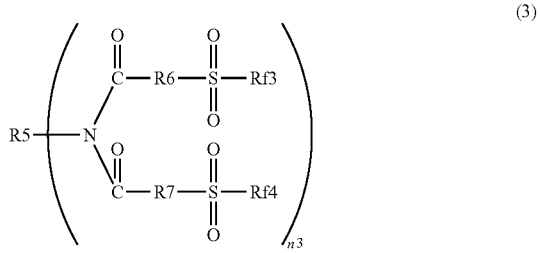

(3)

wherein R5 represents one of an n3-valent hydrocarbon group, an n3-valent oxygen-containing hydrocarbon group, an n3-valent halogenated hydrocarbon group and an n3-valent halogenated oxygen-containing hydrocarbon group, each of R6 and R7 represents one of a divalent hydrocarbon group and a divalent halogenated hydrocarbon group, each of Rf3 and Rf4 represents one of a halogen group and a monovalent halogenated hydrocarbon group, and n3 is an integer of 1 or more, and wherein the sulfonyl compound shown in the chemical formula (1) includes at least one of compounds that are represented by each of a chemical formula (4) and chemical formula (5), the sulfonyl compound shown in the chemical formula (2) includes at least one of compounds that are represented by each of a chemical formula (6) and chemical formula (7), and the sulfonyl compound shown in the chemical formula (3) includes at least one of compounds that are represented by each of a chemical formula (8) and chemical formula (9),

[Chemical formula 4]

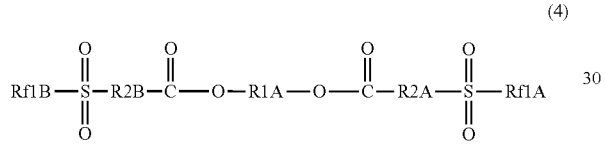

(4)

wherein R1A represents one of a divalent hydrocarbon group, a divalent oxygen-containing hydrocarbon group, a divalent halogenated hydrocarbon group and a divalent halogenated oxygen-containing hydrocarbon group, each of R2A and R2B represents one of a divalent hydrocarbon group and a divalent halogenated hydrocarbon group, each of Rf1A and Rf1B represents one of a halogen group and a monovalent halogenated hydrocarbon group,

[Chemical formula 5]

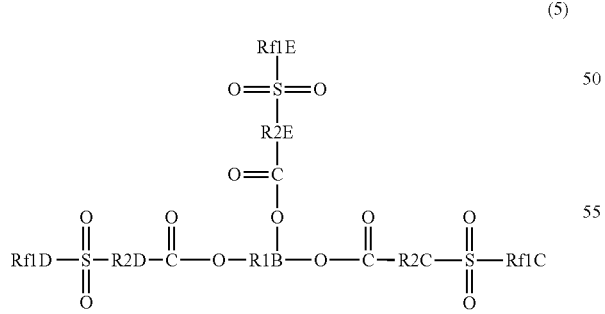

(5)

wherein R1B represents one of a trivalent hydrocarbon group, a trivalent oxygen-containing hydrocarbon group, a trivalent halogenated hydrocarbon group and a trivalent halogenated oxygen-containing hydrocarbon group, each of R2C, R2D and R2E represents one of a divalent hydrocarbon group and a divalent halogenated hydrocarbon group, each of Rf1C, Rf1D and Rf1E represents one of a halogen group and a monovalent halogenated hydrocarbon group,

[Chemical formula 6]

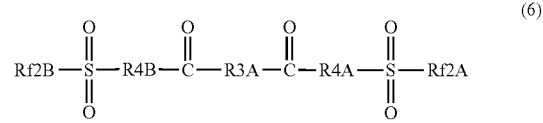

(6)

wherein R3A represents one of a divalent hydrocarbon group, a divalent oxygen-containing hydrocarbon group, a divalent halogenated hydrocarbon group and a divalent halogenated oxygen-containing hydrocarbon group, Each of R4A and R4B represents one of a divalent hydrocarbon group and a divalent halogenated hydrocarbon group, Each of Rf2A and Rf2B represents one of a halogen group and a monovalent halogenated hydrocarbon group,

[Chemical formula 7]

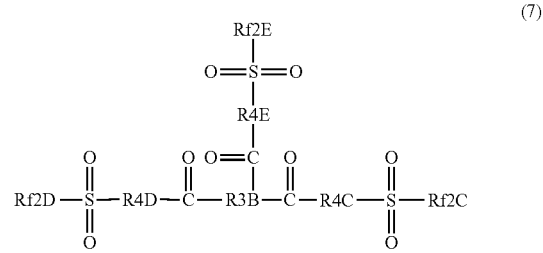

(7)

wherein R3B represents one of a trivalent hydrocarbon group, a trivalent oxygen-containing hydrocarbon group, a trivalent halogenated hydrocarbon group and a trivalent halogenated oxygen-containing hydrocarbon group, Each of R4C, R4D and R4E represents of a divalent hydrocarbon group and a divalent halogenated hydrocarbon group, Each of Rf2C, Rf2D and Rf2E represents of a halogen group and a monovalent halogenated hydrocarbon group,

[Chemical formula 8]

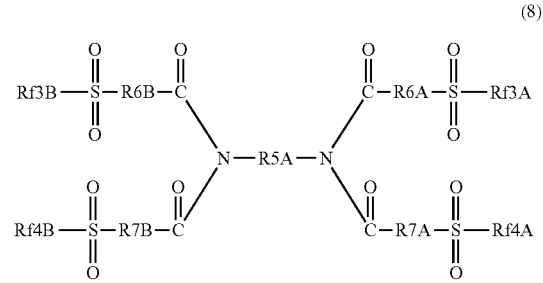

(8)

wherein R5A represents one of a divalent hydrocarbon group, a divalent oxygen-containing hydrocarbon group, a divalent halogenated hydrocarbon group and a divalent halogenated oxygen-containing hydrocarbon group, each of R6A, R6B, R7A and R7B represents one of a divalent hydrocarbon group and a divalent halogenated hydrocarbon group, each of Rf3A, Rf3B, Rf4A and Rf4B represents one of a halogen group and a monovalent halogenated hydrocarbon group, and

[Chemical formula 9]

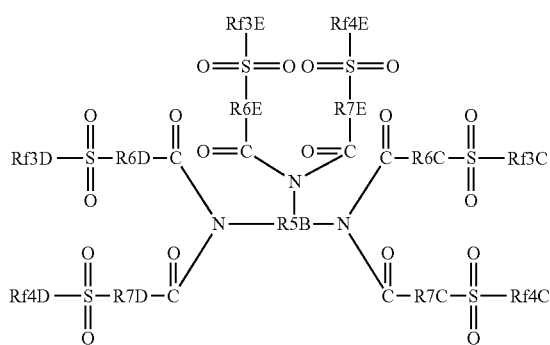

(9)

wherein R5B represents one of a trivalent hydrocarbon group, a trivalent oxygen-containing hydrocarbon group, a trivalent halogenated hydrocarbon group and a trivalent halogenated oxygen-containing hydrocarbon group, each of R6C, R6D, R6E, R7C, R7D and R7E represents one of a divalent hydrocarbon group and a divalent halogenated hydrocarbon group, each of Rf3C, Rf3D, Rf3E, Rf4C, Rf4D and Rf4E represents one of a halogen group and a monovalent halogenated hydrocarbon group.

21. A battery pack comprising:
the secondary battery according to claim 20,
a controller configured to control operation of the secondary battery, and
a switch configured to switch operation of the secondary battery in response to an instruction of the controller.

22. An electrically driven vehicle comprising:
the secondary battery according to claim 20,
a converter configured to convert an electric power supplied from the secondary battery into a driving force,
a driver configured to perform driving depending on the driving force, and
a controller configured to control operation of the secondary battery.

23. Electronic equipment comprising the secondary battery according to claim 20 as an electric power supply source.

24. A secondary battery comprising:
a positive electrode,
a negative electrode, and
an electrolytic solution including at least one kind of sulfonyl compounds that are represented by chemical formula (1), chemical formula (2) and chemical formula (3):

[Chemical formula 1]

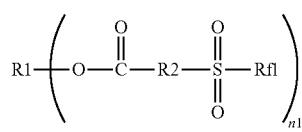

(1)

wherein R1 represents one of an n1-valent hydrocarbon group, an n1-valent oxygen-containing hydrocarbon group, an n1-valent halogenated hydrocarbon group and an n1-valent halogenated oxygen-containing hydrocarbon group, R2 represents one of a divalent hydrocarbon group and a divalent halogenated hydrocarbon group, Rf1 represents one of a halogen group and a monovalent halogenated hydrocarbon group, and n1 is an integer of 2 or more,

[Chemical formula 2]

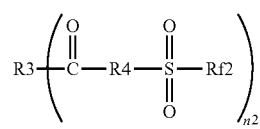

(2)

wherein R3 represents one of an n2-valent hydrocarbon group, an n2-valent oxygen-containing hydrocarbon group, an n2-valent halogenated hydrocarbon group and an n2-valent halogenated oxygen-containing hydrocarbon group, R4 represents one of a divalent hydrocarbon group and a divalent halogenated hydrocarbon group, Rf2 represents one of a halogen group and a monovalent halogenated hydrocarbon group, and n2 is an integer of 1 or more,

[Chemical formula 3]

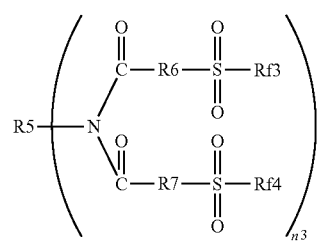

(3)

wherein R5 represents one of an n3-valent hydrocarbon group, an n3-valent oxygen-containing hydrocarbon group, an n3-valent halogenated hydrocarbon group and an n3-valent halogenated oxygen-containing hydrocarbon group, each of R6 and R7 represents one of a divalent hydrocarbon group and a divalent halogenated hydrocarbon group, each of Rf3 and Rf4 represents one of a halogen group and a monovalent halogenated hydrocarbon group, and n3 is an integer of 1 or more, and
wherein the electrolytic solution further comprises at least one kind of dinitrile compounds represented by a chemical formula (16);

NC-R28-CN (16)

wherein R28 represents one of a divalent hydrocarbon group, a divalent halogenated hydrocarbon group, a divalent oxygen-containing group, a divalent nitrogen-containing group, a divalent sulfur-containing group, a divalent phosphorus-containing group and a divalent group in which two or more kinds of them are bound.

25. A battery pack comprising:
the secondary battery according to claim 24,
a controller configured to control operation of the secondary battery, and a switch configured to switch operation of the secondary battery in response to an instruction of the controller.

26. An electrically driven vehicle comprising:
the secondary battery according to claim 24,
a converter configured to convert an electric power supplied from the secondary battery into a driving force,
a driver configured to perform driving depending on the driving force, and
a controller configured to control operation of the secondary battery.

27. Electronic equipment comprising the secondary battery according to claim 24 as an electric power supply source.

28. An electrolytic solution for a secondary battery, comprising:
at least one kind of sulfonyl compounds that are represented by each of a chemical formula (1), chemical formula (2) and chemical formula (3):

[Chemical formula 1]

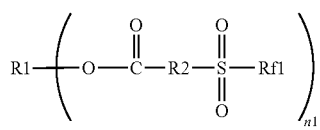
(1)

wherein R1 represents one an n1-valent hydrocarbon group, an n1-valent oxygen-containing hydrocarbon group, an n1-valent halogenated hydrocarbon group and an n1-valent halogenated oxygen-containing hydrocarbon group, R2 represents one of a divalent hydrocarbon group and a divalent halogenated hydrocarbon group, Rf1 represents one of a halogen group and a monovalent halogenated hydrocarbon group, and n1 is an integer of 2 or more,

[Chemical formula 2]

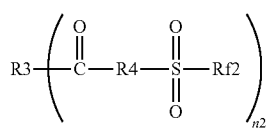
(2)

wherein R3 represents one of an n2-valent hydrocarbon group, an n2-valent oxygen-containing hydrocarbon group, an n2-valent halogenated hydrocarbon group and an n2-valent halogenated oxygen-containing hydrocarbon group, R4 represents one of a divalent hydrocarbon group and a divalent halogenated hydrocarbon group, Rf2 represents one of a halogen group and a monovalent halogenated hydrocarbon group, and n2 is an integer of 1 or more,

[Chemical formula 3]

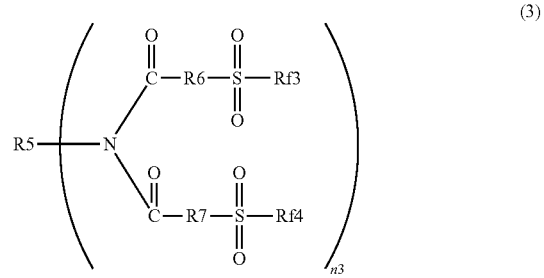
(3)

wherein R5 represents one of an n3-valent hydrocarbon group, an n3-valent oxygen-containing hydrocarbon group, an n3-valent halogenated hydrocarbon group and an n3-valent halogenated oxygen-containing hydrocarbon group, each of R6 and R7 represents one of a divalent hydrocarbon group and a divalent halogenated hydrocarbon group, each of Rf3 and Rf4 represents one of a halogen group and a monovalent halogenated hydrocarbon group, and n3 is an integer of 1 or more, and
wherein the n2-valent hydrocarbon group includes a group in which n2 hydrogen groups are eliminated from a hydrocarbon, and the hydrocarbon is one of an alkane, an alkene, an alkyne, an alicyclic hydrocarbon, an aromatic hydrocarbon and combinations thereof,
the n2-valent oxygen-containing hydrocarbon group includes a group in which one or two or more ether bounds are introduced into a middle of the n2-valent hydrocarbon group,
the n2-valent halogenated hydrocarbon group includes a group in which at least one hydrogen group of the n2-valent hydrocarbon group is substituted with a halogen group,
the n2-valent halogenated oxygen-containing hydrocarbon group includes a group in which at least one hydrogen group of the n2-valent oxygen-containing hydrocarbon group is substituted with a halogen group, and
the halogen group includes at least one kind of a fluorine group, a chlorine group, a bromine group and an iodine group.

29. An electrolytic solution for a secondary battery, comprising:
at least one kind of sulfonyl compounds that are represented by each of a chemical formula (1), chemical formula (2) and chemical formula (3):

[Chemical formula 1]

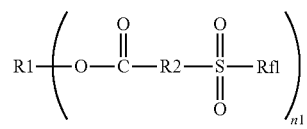
(1)

wherein R1 represents one an n1-valent hydrocarbon group, an n1-valent oxygen-containing hydrocarbon group, an n1-valent halogenated hydrocarbon group and an n1-valent halogenated oxygen-containing hydrocarbon group, R2 represents one of a divalent hydrocarbon group and a divalent halogenated hydrocarbon group, Rf1 represents one of a halogen group and a monovalent halogenated hydrocarbon group, and n1 is an integer of 2 or more,

[Chemical formula 2]

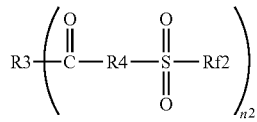
(2)

wherein R3 represents one of an n2-valent hydrocarbon group, an n2-valent oxygen-containing hydrocarbon group, an n2-valent halogenated hydrocarbon group and an n2-valent halogenated oxygen-containing hydrocarbon group, R4 represents one of a divalent hydrocarbon group and a divalent halogenated hydrocarbon group, Rf2 represents one of a halogen group and a monovalent halogenated hydrocarbon group, and n2 is an integer of 1 or more,

[Chemical formula 3]

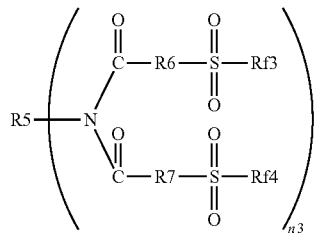
(3)

wherein R5 represents one of an n3-valent hydrocarbon group, an n3-valent oxygen-containing hydrocarbon group, an n3-valent halogenated hydrocarbon group and an n3-valent halogenated oxygen-containing hydrocarbon group, each of R6 and R7 represents one of a divalent hydrocarbon group and a divalent halogenated hydrocarbon group, each of Rf3 and Rf4 represents one of a halogen group and a monovalent halogenated hydrocarbon group, and n3 is an integer of 1 or more, and wherein the n2 is 2 or more, and the n3 is 2 or more.

30. An electrolytic solution for a secondary battery, comprising:
at least one kind of sulfonyl compounds that are represented by each of a chemical formula (1), chemical formula (2) and chemical formula (3):

[Chemical formula 1]

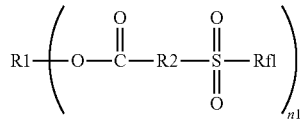
(1)

wherein R1 represents one an n1-valent hydrocarbon group, an n1-valent oxygen-containing hydrocarbon group, an n1-valent halogenated hydrocarbon group and an n1-valent halogenated oxygen-containing hydrocarbon group, R2 represents one of a divalent hydrocarbon group and a divalent halogenated hydrocarbon group, Rf1 represents one of a halogen group and a monovalent halogenated hydrocarbon group, and n1 is an integer of 2 or more,

[Chemical formula 2]

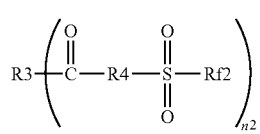
(2)

wherein R3 represents one of an n2-valent hydrocarbon group, an n2-valent oxygen-containing hydrocarbon group, an n2-valent halogenated hydrocarbon group and an n2-valent halogenated oxygen-containing hydrocarbon group, R4 represents one of a divalent hydrocarbon group and a divalent halogenated hydrocarbon group, Rf2 represents one of a halogen group and a monovalent halogenated hydrocarbon group, and n2 is an integer of 1 or more,

[Chemical formula 3]

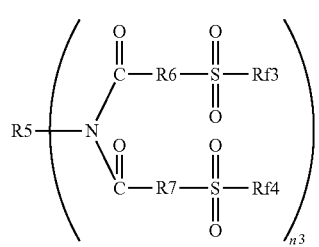
(3)

wherein R5 represents one of an n3-valent hydrocarbon group, an n3-valent oxygen-containing hydrocarbon group, an n3-valent halogenated hydrocarbon group and an n3-valent halogenated oxygen-containing hydrocarbon group, each of R6 and R7 represents one of a divalent hydrocarbon group and a divalent halogenated hydrocarbon group, each of Rf3 and Rf4 represents one of a halogen group and a monovalent halogenated hydrocarbon group, and n3 is an integer of 1 or more, wherein the sulfonyl compound shown in the chemical formula (1) includes at least one of compounds that are represented by each of a chemical formula (4) and chemical formula (5), the sulfonyl compound shown in the chemical formula (2) includes at least one of compounds that are represented by each of a chemical formula (6) and chemical formula (7), and the sulfonyl compound shown in the chemical formula (3) includes at least one of compounds that are represented by each of a chemical formula (8) and chemical formula (9),

[Chemical formula 4]

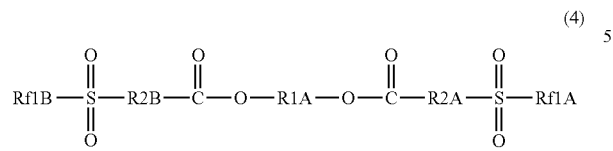

(4)

wherein R1A represents one of a divalent hydrocarbon group, a divalent oxygen-containing hydrocarbon group, a divalent halogenated hydrocarbon group and a divalent halogenated oxygen-containing hydrocarbon group, each of R2A and R2B represents one of a divalent hydrocarbon group and a divalent halogenated hydrocarbon group, each of Rf1A and Rf1B represents one of a halogen group and a monovalent halogenated hydrocarbon group,

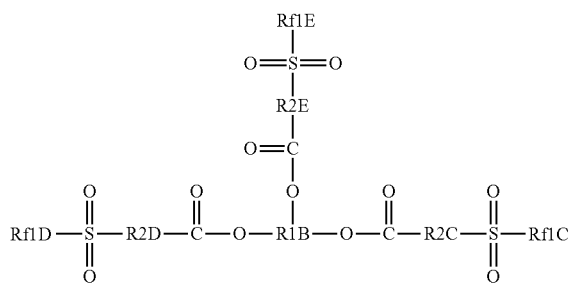

(5)

wherein R1B represents one of a trivalent hydrocarbon group, a trivalent oxygen-containing hydrocarbon group, a trivalent halogenated hydrocarbon group and a trivalent halogenated oxygen-containing hydrocarbon group, each of R2C, R2D and R2E represents one of a divalent hydrocarbon group and a divalent halogenated hydrocarbon group, each of Rf1C, Rf1D and Rf1E represents one of a halogen group and a monovalent halogenated hydrocarbon group,

[Chemical formula 6]

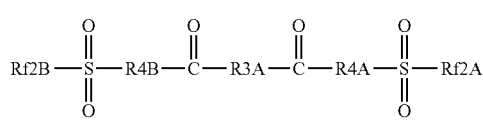

(6)

wherein R3A represents one of a divalent hydrocarbon group, a divalent oxygen-containing hydrocarbon group, a divalent halogenated hydrocarbon group and a divalent halogenated oxygen-containing hydrocarbon group, Each of R4A and R4B represents one of a divalent hydrocarbon group and a divalent halogenated hydrocarbon group, Each of Rf2A and Rf2B represents one of a halogen group and a monovalent halogenated hydrocarbon group,

[Chemical formula 7]

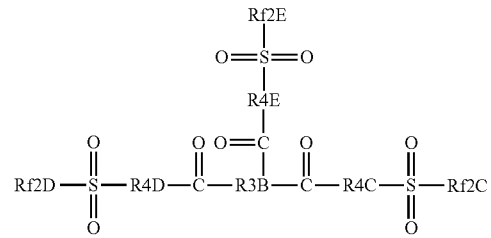

(7)

wherein R3B represents one of a trivalent hydrocarbon group, a trivalent oxygen-containing hydrocarbon group, a trivalent halogenated hydrocarbon group and a trivalent halogenated oxygen-containing hydrocarbon group, Each of R4C, R4D and R4E represents of a divalent hydrocarbon group and a divalent halogenated hydrocarbon group, Each of Rf2C, Rf2D and Rf2E represents of a halogen group and a monovalent halogenated hydrocarbon group,

[Chemical formula 8]

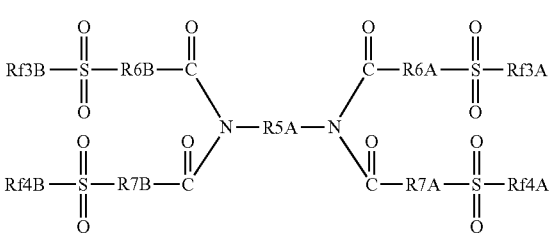

(8)

wherein R5A represents one of a divalent hydrocarbon group, a divalent oxygen-containing hydrocarbon group, a divalent halogenated hydrocarbon group and a divalent halogenated oxygen-containing hydrocarbon group, each of R6A, R6B, R7A and R7B represents one of a divalent hydrocarbon group and a divalent halogenated hydrocarbon group, each of Rf3A, Rf3B, Rf4A and Rf4B represents one of a halogen group and a monovalent halogenated hydrocarbon group, and

[Chemical formula 9]

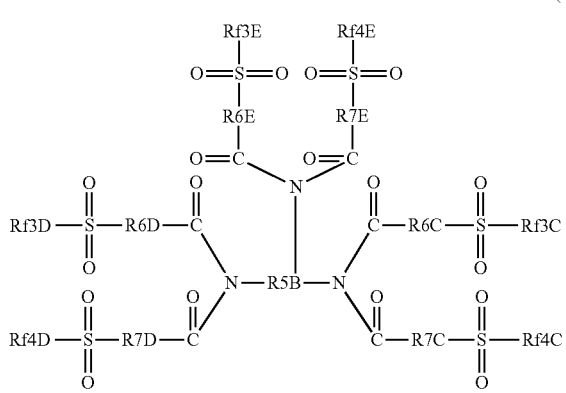

(9)

wherein R5B represents one of a trivalent hydrocarbon group, a trivalent oxygen-containing hydrocarbon group, a trivalent halogenated hydrocarbon group and a trivalent halogenated oxygen-containing hydrocarbon group, each of R6C, R6D, R6E, R7C, R7D and R7E represents one of a divalent hydrocarbon group and a divalent halogenated hydrocarbon group, each of Rf3C, Rf3D, Rf3E, Rf4C, Rf4D and Rf4E represents one of a halogen group and a monovalent halogenated hydrocarbon group.

31. An electrolytic solution for a secondary battery, comprising:

at least one kind of sulfonyl compounds that are represented by each of a chemical formula (1), chemical formula (2) and chemical formula (3):

[Chemical formula 1]

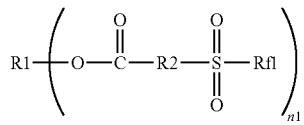
(1)

wherein R1 represents one an n1-valent hydrocarbon group, an n1-valent oxygen-containing hydrocarbon group, an n1-valent halogenated hydrocarbon group and an n1-valent halogenated oxygen-containing hydrocarbon group, R2 represents one of a divalent hydrocarbon group and a divalent halogenated hydrocarbon group, Rf1 represents one of a halogen group and a monovalent halogenated hydrocarbon group, and n1 is an integer of 2 or more,

[Chemical formula 2]

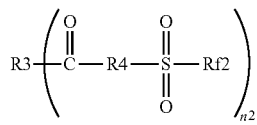
(2)

wherein R3 represents one of an n2-valent hydrocarbon group, an n2-valent oxygen-containing hydrocarbon group, an n2-valent halogenated hydrocarbon group and an n2-valent halogenated oxygen-containing hydrocarbon group, R4 represents one of a divalent hydrocarbon group and a divalent halogenated hydrocarbon group, Rf2 represents one of a halogen group and a monovalent halogenated hydrocarbon group, and n2 is an integer of 1 or more,

[Chemical formula 3]

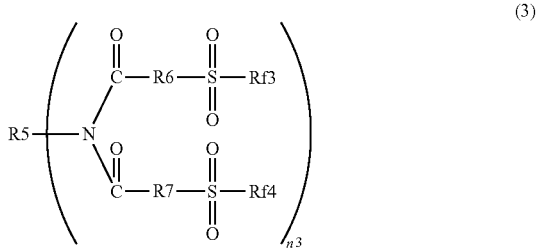
(3)

wherein R5 represents one of an n3-valent hydrocarbon group, an n3-valent oxygen-containing hydrocarbon group, an n3-valent halogenated hydrocarbon group and an n3-valent halogenated oxygen-containing hydrocarbon group, each of R6 and R7 represents one of a divalent hydrocarbon group and a divalent halogenated hydrocarbon group, each of Rf3 and Rf4 represents one of a halogen group and a monovalent halogenated hydrocarbon group, and n3 is an integer of 1 or more, and wherein the electrolytic solution further comprises at least one kind of dinitrile compounds represented by a chemical formula (16):

NC-R28-CN (16)

wherein R28 represents one of a divalent hydrocarbon group, a divalent halogenated hydrocarbon group, a divalent oxygen-containing group, a divalent nitrogen-containing group, a divalent sulfur-containing group, a divalent phosphorus-containing group and a divalent group in which two or more kinds of them are bound.

* * * * *